(12) United States Patent
Galler et al.

(10) Patent No.: US 12,030,942 B2
(45) Date of Patent: Jul. 9, 2024

(54) ANTI-PD-1 ANTIBODIES AND COMPOSITIONS

(71) Applicant: Les Laboratoires Servier, Suresnes (FR)

(72) Inventors: Gunther Galler, Jyllinge (DK); Monika Gad, Alleroed (DK); Klaus Koefoed, Copenhagen (DK); Ivan D. Horak, West Orange, NJ (US); Thomas Bouquin, Alleroed (DK); Michael Kragh, Copenhagen (DK); Mikkel Pedersen, Alleroed (DK)

(73) Assignee: LES LABORATOIRES SERVIER, Suresnes (FR)

(*) Notice: Subject to any disclaimer, the term of this patent is extended or adjusted under 35 U.S.C. 154(b) by 561 days.

(21) Appl. No.: 17/324,508

(22) Filed: May 19, 2021

(65) Prior Publication Data

US 2021/0284734 A1    Sep. 16, 2021

Related U.S. Application Data

(62) Division of application No. 15/765,337, filed as application No. PCT/EP2016/073421 on Sep. 30, 2016, now Pat. No. 11,034,765.

(60) Provisional application No. 62/236,341, filed on Oct. 2, 2015.

(51) Int. Cl.
  *C07K 16/28* (2006.01)
  *A61K 45/06* (2006.01)
  *A61P 35/00* (2006.01)
  *A61K 39/00* (2006.01)

(52) U.S. Cl.
  CPC .......... *C07K 16/2818* (2013.01); *A61K 45/06* (2013.01); *A61P 35/00* (2018.01); *A61K 2039/505* (2013.01)

(58) Field of Classification Search
  CPC ............ C07K 16/2818; C07K 2317/23; C07K 2317/24; C07K 2317/33; C07K 2317/34; C07K 2317/76; C07K 2317/92; A61K 45/06; A61K 2039/505; A61P 35/00
  See application file for complete search history.

(56) References Cited

U.S. PATENT DOCUMENTS

| | | |
|---|---|---|
| 8,354,509 B2 | 1/2013 | Carven et al. |
| 8,927,697 B2 | 1/2015 | Davis et al. |
| 11,034,765 B2 | 6/2021 | Galler et al. |
| 11,359,018 B2 | 6/2022 | Lantto et al. |
| 2011/0229461 A1 | 9/2011 | Tyson et al. |
| 2012/0039906 A1* | 2/2012 | Olive ............... A61P 37/04 435/336 |
| 2013/0309250 A1* | 11/2013 | Cogswell ............ A61P 35/04 530/388.2 |
| 2014/0328833 A1 | 11/2014 | Korman et al. |
| 2015/0203579 A1 | 7/2015 | Papadopoulos et al. |
| 2015/0210769 A1 | 7/2015 | Freeman et al. |
| 2020/0407444 A1 | 12/2020 | Lindsted et al. |
| 2022/0380470 A1 | 12/2022 | Lindsted et al. |

FOREIGN PATENT DOCUMENTS

| | | |
|---|---|---|
| EP | 3026062 A1 | 6/2016 |
| EP | 3081576 A1 | 10/2016 |
| WO | WO 2006/029879 A1 | 3/2006 |
| WO | WO 2006/121168 A1 | 11/2006 |
| WO | WO 2008/019817 A1 | 2/2008 |
| WO | WO 2008/156712 A1 | 12/2008 |
| WO | WO 2010/029434 A1 | 3/2010 |
| WO | WO 2010/029435 A1 | 3/2010 |
| WO | WO 2011/110621 A1 | 9/2011 |
| WO | WO 2011/159877 A1 | 12/2011 |
| WO | WO 2012/135408 A1 | 10/2012 |
| WO | WO 2015/035606 A1 | 3/2015 |
| WO | WO 2015/042246 A1 | 3/2015 |
| WO | WO 2015/048312 A1 | 4/2015 |
| WO | WO 2015/112800 A1 | 7/2015 |
| WO | WO 2015/112900 A1 | 7/2015 |
| WO | WO 2015/175340 A1 | 11/2015 |
| WO | WO 2016/014688 A2 | 1/2016 |
| WO | WO 2016/092419 A1 | 6/2016 |
| WO | WO 2016/106159 A1 | 6/2016 |
| WO | WO 2017/055547 A1 | 4/2017 |
| WO | WO 2017/198741 A1 | 11/2017 |

OTHER PUBLICATIONS

Anonymous, "Anti-LAG-3 or Urelumab Alone and in Combination with Nivolumab in Treating Patients with Recurrent Glioblastoma—Full Text View," ClinicalTrials.gov (2016).
Anonymous, "NCT02608268: Phase I-Ib/II Open-label Multicenter Study of the Safety and Efficacy of MBG453 [TIM-3] as Single Agent and in Combination with PDR001 [PD-1]in Adult Patients with Advanced Malignancies," ClinicalTrials.gov (2017).
Anonymous: "Naturally optimized human antibodies," 1-16 (2016). Retrieved from the Internet: URL: http://content.stockpr.eom/omniab/db/2 52/746/file/OmniAb.pdf [retrieved on Jan. 9, 2018].
Benjamini et al., "Immunology: A Short Course," 2nd edition, p. 40 only (1991).
Cheng et al., "Structure and interactions of the human programmed cell death 1 receptor," J Biol Chem 288(17):11771-85 (2013).
Colman, "Effects of amino acid sequence changes on antibody-antigen interactions," Res Immunol. 145(1):33-6 (1994).
Du et al., "TIM-3 as a Target for Cancer Immunotherapy and Mechanisms of Action," Int J Mol Sci. 18(3):645 (2017).

(Continued)

*Primary Examiner* — Nelson B Moseley, II

(74) *Attorney, Agent, or Firm* — Steptoe LLP; Z. Ying Li; Wyan-Ching M. Lee

(57) ABSTRACT

This invention relates to anti-PD-1 antibodies and methods of using them in treating diseases and conditions related to PD-1 activity, e.g., cancer.

18 Claims, 20 Drawing Sheets

Specification includes a Sequence Listing.

(56) References Cited

OTHER PUBLICATIONS

Ferrara et al., "Recombinant renewable polyclonal antibodies," MAbs. 7(1):32-41 (2015).
Fenwick et al., "Identification of novel antagonistic anti-PD-1 antibodies that are non-blocking of the PD-1 / PD-L1 interaction," Journal of Clinical Oncology 34:15_suppl (2016).
Friedlaender et al., "New emerging targets in cancer immunotherapy: the role of TIM3," Esmo Open. 4(Suppl 3): e000497 (2019).
Hu et al., "Preparation and characterization of a novel monoclonal antibody against human PD-1," Current Immunology, 30(1):24-29 (2010) (with English abstract).
Jin et al., "Cooperation of Tim-3 and PD-1 in CD8 T-cell exhaustion during chronic viral infection," Proc Natl Acad Sci U S A. 107(33):14733-8 (2010).
Jing et al., "Combined immune checkpoint protein blockade and low dose whole body irradiation as immunotherapy for myeloma," J Immunother. Cancer 3(1):2 (2015).
Jun et al., "Generation of antagonistic anti-TIM-3 and anti-LAG-3 monoclonal antibodies for potential novel immunotherapy combinations," AACR annual meeting 2014. (Oct. 1, 2014).
Kehry, "Targeting PD-1, TIM-3 and LAG-3 in combination for improved Immunotherapy Combinations," Journal for Immunotherapy of Cancer, 1 page (2015). [Retrieved from Internet—URL: https://www.tesarobio.com/application/files/3014/7552/4272/AACRApr2015.pdf].
Koyama et al., "Adaptive resistance to therapeutic PD-1 blockade is associated with upregulation of alternative immune checkpoints," Nat Commun. 7:10501 (2016).
Lee et al., "Structural basis of checkpoint blockade by monoclonal antibodies in cancer immunotherapy," Nature Communications 7:13354 (2016).
Leventakos et al., "Advances in the treatment of non-small cell lung cancer: focus on nivolumab, pembrolizumab, and atezolizumab," BioDrugs 30:397-405 (2016).
Lin et al., "Improved affinity of a chicken single-chain antibody to avian infectious bronchitis virus by site-directed mutagenesis of complementarity-determining region H3," African Journal of Biotechnology 10(79):18294-18302 (2011).
Liu et al., "Glycosylation-independent binding of monoclonal antibody toripalimab to FG loop of PD-1 for tumor immune checkpoint therapy," MAbs. 11(4): 681-690 (2019).
Liu et al., "N-glycosylation of PD-1 promotes binding of camrelizumab," EMBO Rep. 21(12): e51444 (2020).
Liu et al., "PD-1 N58-glycosylation-dependent binding of monoclonal antibody cemiplimab for immune checkpoint therapy," Front Immunol. 13:826045 (2022).
Mariuzza et al, "Structural basis of antigen-antibody recognition," Ann Rev Biophys Biophys Chem. 16:139-159 (1987).
McCarthy et al., "Altering the fine specificity of an anti-Legionella single chain antibody by a single amino acid insertion," J Immunol. Methods, 251(1-2):137-149 (2001).
Moon, "Abstract 1641: Dual antibody blockade of TIM3 and PD1 on NYES01 redirected human T cells leads to augmented control of lung cancer tumors," Cancer Research 77: 1641(2017).
Na et al., "Structural basis for blocking PD-1-mediated immune suppression by therapeutic antibody pembrolizumab," Cell Res. 27(1): 147-150 (2017).
Pan et al., "Blocking neuropilin-1 function has an additive effect with anti-VEGF to inhibit tumor growth," Cancer Cell 11(1):53-67 (2007).
Rayner et al., "The solution structures of two human IgG1 antibodies show conformational stability and accommodate their C1q and FcγR ligands," J Biol Chem 290(13):8420-38 (2015).
Rudikoff et al., "Single amino acid substitution altering antigen-binding specificity." Proc Natl Acad Sci. USA. 79(6): 1979-1983 (1982).
Sakuishi et al., "Targeting Tim-3 and PD-1 pathways to reverse T cell exhaustion and restore anti-tumor immunity," J Exp Med. 207(10):2187-94 (2010).
Scapin et al., "Structure of full-length human anti-PDI therapeutic IgG4 antibody pembrolizumab," Nat Struct Mol Biol. 22(12):953-8 (2015).
Storz, "Intellectual property issues of immune checkpoint inhibitors," MAbs. 8(1):10-26 (2016).
Vincent et al., "Current strategies in antibody engineering: Fc engineering and pH-dependent antigen binding, bispecific antibodies and antibody drug conjugates," Biotechnol J. 7:1444-1450 (2012).
Wang et al., "In vitro characterization of the anti-PD-1 antibody nivolumab, BMS-936558, and in vivo toxicology in non-human primates," Cancer Immunol Res. 2(9):846-56 (2014).
WHO, International Nonproprietary Names for Pharmaceutical Substances (INN), WHO Drug Information, 31(1) List 77:74-75 (2017).
WHO, International Nonproprietary Names for Pharmaceutical Substances (INN), WHO Drug Information, 33(1) List 81:124-125 (2019).
WHO, International Nonproprietary Names for Pharmaceutical Substances (INN), WHO Drug Information, 33(1) List 81:57-58 (2019).
Woo et al., "Immune inhibitory molecules LAG-3 and PD-1 synergistically regulate T-cell function to promote tumoral immune escape," Cancer Res. 72(4):917-27 (2012).
Zak et al., "Structure of the complex of human programmed death 1, PD-1, and its ligand PD-L1," Structure 23(12):2341-2348 (2015).
U.S. Appl. No. 16/500,918, filed Oct. 4, 2019, Lindsted et al.
U.S. Appl. No. 17/834,554, filed Jun. 7, 2022, Lindsted et al.

* cited by examiner

ANTI-PD-1 ANTIBODIES AND COMPOSITIONS

CROSS-REFERENCE TO RELATED APPLICATIONS

This application is a divisional application of U.S. patent application Ser. No. 15/765,337, filed on Apr. 2, 2018, which is a national stage application under 35 U.S.C. § 371 of International Patent Application PCT/EP2016/073421, filed on Sep. 30, 2016, which claims priority from U.S. Patent Application 62/236,341, filed on Oct. 2, 2015. The disclosures of those applications are incorporated by reference herein in their entirety.

SEQUENCE LISTING

The instant application contains a Sequence Listing which has been submitted electronically in ASCII format and is hereby incorporated by reference in its entirety. Said ASCII copy, created on Sep. 28, 2016, is named 022675_W0052_SL.txt and is 65,000 bytes in size.

BACKGROUND OF THE INVENTION

PD-1, also known as Programmed Cell Death Protein 1 and CD279, is a 268 amino acid cell surface receptor that belongs to the immunoglobulin superfamily. PD-1 is a member of the CD28 family of T cell regulators and is expressed on T cells, B cells and macrophages. It binds ligands PD-L1 (also known as B7 homolog) and PD-L2 (also known as B7-DC).

PD-1 is a type I membrane protein whose structure includes an extracellular IgV domain, a transmembrane region and an intracellular tail containing two phosphorylation sites. Known as an immune checkpoint protein, PD-1 functions as an inducible immune modulatory receptor, playing a role in, e.g., negative regulation of T cell responses to antigen stimulation.

PD-L1 is the predominant ligand for PD-1. Binding of PD-L1 to PD-1 inhibits T cell activity, reducing cytokine production and suppressing T cell proliferation. Cancer cells that express PD-L1 are able to exploit this mechanism to inactivate the anti-tumor activity of T cells via binding of PD-L1 to the PD-1 receptor.

In view of its immune response regulatory properties, PD-1 has been investigated as a potential target for immunotherapy, including treatment of cancer and autoimmune diseases. Two anti-PD-1 antibodies, pembrolizumab and nivolumab, have been approved in the United States and Europe for treating certain cancers.

In view of the critical role of PD-1 as an immune modulator, there is a need for new and improved immune therapies that target PD-1 to treat cancers and certain disorders of the immune system.

SUMMARY OF THE INVENTION

The present invention is directed to novel recombinant antibodies targeting PD-1, as well as pharmaceutical compositions comprising one or more of these antibodies, and use of the antibodies and pharmaceutical compositions for enhancing immunity in a patient, and for treatment of cancers originating from tissues such as skin, lung, intestine, ovary, brain, prostate, kidney, soft tissues, the hematopoietic system, head & neck, liver, bladder, breast, stomach, uterus and pancreas. Compared to currently available treatments for such cancers, including antibody treatments, it is contemplated that the antibodies of the invention may provide a superior clinical response either alone or in combination with another cancer therapeutic, such as an antibody targeting another immune checkpoint protein.

In one embodiment, the present invention provides an anti-PD-1 antibody or an antigen-binding portion thereof, wherein the antibody competes for binding to human PD-1 with, or binds to the same epitope of human PD-1 as, any one of antibodies 12819.15384, 12748.15381, 12748.16124, 12865.15377, 12892.15378, 12796.15376, 12777.15382, 12760.15375 and 13112.15380.

In some embodiments, the anti-PD-1 antibody comprises H-CDR1-3 comprising the H-CDR1-3 sequences, respectively, of antibody 12819.15384, 12748.15381, 12748.16124, 12865.15377, 12892.15378, 12796.15376, 12777.15382, 12760.15375, or 13112.15380.

In some embodiments, the anti-PD-1 antibody has a heavy chain variable domain ($V_H$) that is at least 90% (e.g., at least 92%, at least 95%, at least 98%, or at least 99%) identical in amino acid sequence to the $V_H$ domain of antibody 12819.15384, 12748.15381, 12748.16124, 12865.15377, 12892.15378, 12796.15376, 12777.15382, 12760.15375, or 13112.15380.

In some embodiments, the anti-PD-1 antibody has a $V_H$ that comprises the $V_H$ amino acid sequence of antibody 12819.15384, 12748.15381, 12748.16124, 12865.15377, 12892.15378, 12796.15376, 12777.15382, 12760.15375, or 13112.15380.

In some embodiments, the anti-PD-1 antibody has a heavy chain (HC) that comprises the $V_H$ amino acid sequence of antibody 12819.15384, 12748.15381, 12748.16124, 12865.15377, 12892.15378, 12796.15376, 12777.15382, 12760.15375, or 13112.15380 and the heavy chain constant region amino acid sequence of SEQ ID NO: 67.

In some embodiments, the anti-PD-1 antibody comprises L-CDR1-3 comprising the L-CDR1-3 sequences, respectively, of antibody 12819.15384, 12748.15381, 12748.16124, 12865.15377, 12892.15378, 12796.15376, 12777.15382, 12760.15375, or 13112.15380.

In some embodiments, the anti-PD-1 antibody has a light chain variable domain ($V_L$) that is at least 90% (e.g., at least 92%, at least 95%, at least 98%, or at least 99%) identical in amino acid sequence to the $V_L$ domain of antibody 12819.15384, 12748.15381, 12748.16124, 12865.15377, 12892.15378, 12796.15376, 12777.15382, 12760.15375, or 13112.15380.

In some embodiments, the anti-PD-1 antibody has a $V_L$ that comprises the $V_L$ amino acid sequence of antibody 12819.15384, 12748.15381, 12748.16124, 12865.15377, 12892.15378, 12796.15376, 12777.15382, 12760.15375, or 13112.15380.

In some embodiments, the anti-PD-1 antibody has a light chain (LC) that comprises the $V_L$ amino acid sequence of antibody 12819.15384, 12748.15381, 12748.16124, 12865.15377, 12892.15378, 12796.15376, 12777.15382, 12760.15375, or 13112.15380 and the light chain constant region amino acid sequence of SEQ ID NO: 68.

In some embodiments, the anti-PD-1 antibody comprises any of the above-described heavy chain sequences and any of the above light chain sequences.

In some embodiments, the anti-PD-1 antibody comprises the H-CDR3 and L-CDR3 amino acid sequences of antibody 12819.15384, 12748.15381, 12748.16124, 12865.15377, 12892.15378, 12796.15376, 12777.15382, 12760.15375, or 13112.15380.

In some embodiments, the anti-PD-1 antibody comprises the H-CDR1-3 and L-CDR1-3 amino acid sequences of antibody 12819.15384, 12748.15381, 12748.16124, 12865.15377, 12892.15378, 12796.15376, 12777.15382, 12760.15375, or 13112.15380.

In some embodiments, the anti-PD-1 antibody has a $V_H$ and a $V_L$ that are at least 90% (e.g., at least 92%, at least 95%, at least 98%, or at least 99%) identical in amino acid sequence to the $V_H$ and $V_L$, respectively, of antibody 12819.15384, 12748.15381, 12748.16124, 12865.15377, 12892.15378, 12796.15376, 12777.15382, 12760.15375, or 13112.15380.

In some embodiments, the anti-PD-1 antibody has a $V_H$ and $V_L$ that comprise or consist of the $V_H$ and $V_L$ amino acid sequences, respectively, of antibody 12819.15384, 12748.15381, 12748.16124, 12865.15377, 12892.15378, 12796.15376, 12777.15382, 12760.15375, or 13112.15380.

In some embodiments, the anti-PD-1 antibody has an HC and an LC that comprise or consist of the HC and LC amino acid sequences, respectively, of antibody 12819.15384, 12748.15381, 12748.16124, 12865.15377, 12892.15378, 12796.15376, 12777.15382, 12760.15375, or 13112.15380.

In some embodiments, the anti-PD-1 antibody has (1) an HC that comprises the $V_H$ amino acid sequence of an antibody selected from the group consisting of antibodies 12819.15384, 12748.15381, 12748.16124, 12865.15377, 12892.15378, 12796.15376, 12777.15382, 12760.15375, and 13112.15380, and the heavy chain constant region amino acid sequence of SEQ ID NO: 67; and (2) an LC that comprises the $V_L$ amino acid sequence of that selected antibody and the light chain constant region amino acid sequence of SEQ ID NO: 68.

In some embodiments, the anti-PD-1 antibody or antigen-binding portion of the invention comprises the H-CDR1-3 and L-CDR1-3 amino acid sequences of:
  a) SEQ ID NOs: 18, 19, 20, 21, 22, and 23, respectively;
  b) SEQ ID NOs: 24, 25, 26, 27, 28, and 29, respectively;
  c) SEQ ID NOs: 30, 31, 32, 33, 34, and 35, respectively;
  d) SEQ ID NOs: 36, 37, 38, 39, 40, and 41, respectively;
  e) SEQ ID NOs: 42, 43, 44, 45, 46, and 47, respectively;
  f) SEQ ID NOs: 48, 49, 50, 51, 52, and 53, respectively;
  g) SEQ ID NOs: 54, 55, 56, 57, 58, and 59, respectively; or
  h) SEQ ID NOs: 60, 61, 62, 63, 64, and 65, respectively.

In some embodiments, the anti-PD-1 antibody or antigen-binding portion of the invention comprises a heavy chain variable domain and a light chain variable domain having the amino acid sequences of:
  a) SEQ ID NOs: 2 and 3, respectively;
  b) SEQ ID NOs: 4 and 5, respectively;
  c) SEQ ID NOs: 4 and 66, respectively;
  d) SEQ ID NOs: 6 and 7, respectively;
  e) SEQ ID NOs: 8 and 9, respectively;
  f) SEQ ID NOs: 10 and 11, respectively;
  g) SEQ ID NOs: 12 and 13, respectively;
  h) SEQ ID NOs: 14 and 15, respectively; or
  i) SEQ ID NOs: 16 and 17, respectively.

In some embodiments, the anti-PD-1 antibody of the invention comprises:
  a) an HC comprising the amino acid sequences of SEQ ID NOs: 2 and 67 and an LC comprising the amino acid sequences of SEQ ID NOs: 3 and 68;
  b) an HC comprising the amino acid sequences of SEQ ID NOs: 4 and 67 and an LC comprising the amino acid sequences of SEQ ID NOs: 5 and 68;
  c) an HC comprising the amino acid sequences of SEQ ID NOs: 4 and 67 and an LC comprising the amino acid sequences of SEQ ID NOs: 66 and 68;
  d) an HC comprising the amino acid sequences of SEQ ID NOs: 6 and 67 and an LC comprising the amino acid sequences of SEQ ID NOs: 7 and 68;
  e) an HC comprising the amino acid sequences of SEQ ID NOs: 8 and 67 and an LC comprising the amino acid sequences of SEQ ID NOs: 9 and 68;
  f) an HC comprising the amino acid sequences of SEQ ID NOs: 10 and 67 and an LC comprising the amino acid sequences of SEQ ID NOs: 11 and 68;
  g) an HC comprising the amino acid sequences of SEQ ID NOs: 12 and 67 and an LC comprising the amino acid sequences of SEQ ID NOs: 13 and 68;
  h) an HC comprising the amino acid sequences of SEQ ID NOs: 14 and 67 and an LC comprising the amino acid sequences of SEQ ID NOs: 15 and 68; or
  i) an HC comprising the amino acid sequences of SEQ ID NOs: 16 and 67 and an LC comprising the amino acid sequences of SEQ ID NOs: 17 and 68.

In some embodiments, the antibody or antigen-binding portion of the invention comprises H-CDR1-3 and L-CDR1-3 comprising the amino acid sequences of SEQ ID NOs: 18-20 and SEQ ID NOs: 21-23, respectively. In certain embodiments, the anti-PD-1 antibody comprises a $V_H$ comprising the amino acid sequence of SEQ ID NO: 2 and a $V_L$ comprising the amino acid sequence of SEQ ID NO: 3. In particular embodiments, the anti-PD-1 antibody comprises a heavy chain comprising the amino acid sequences of SEQ ID NOs: 2 and 67 and a light chain comprising the amino acid sequences of SEQ ID NOs: 3 and 68.

The invention also provides an anti-PD-1 antibody or an antigen-binding portion thereof that binds to an epitope of PD-1 comprising amino acid residue K131 (e.g., 12819 and 12865 antibodies such as those listed in Tables 1, 4-9, and 11-14). In some embodiments, the epitope further comprises amino acid residues P130 and A132, and may additionally comprise amino acid residues V64 and L128 (e.g., a 12819 antibody). In some embodiments, the epitope further comprises amino acid residue E136 (e.g., a 12865 antibody).

The invention also provides an anti-PD-1 antibody or an antigen-binding portion thereof that binds to an epitope of PD-1 comprising amino acid residues V44 and T145 of SEQ ID NO: 1 (e.g., a 13112 antibody such as those listed in Tables 1, 4-7, 9, and 11-14).

In particular embodiments, the antibody or portion binds to an epitope of PD-1 comprising amino acid residues V64, L128, P130, K131, and A132 of SEQ ID NO: 1 (e.g., a 12819 antibody), amino acid residues K131 and E136 of SEQ ID NO: 1 (e.g., a 12865 antibody), or amino acid residues V44 and T145 of SEQ ID NO: 1 (e.g., a 13112 antibody).

The invention also provides a monoclonal antibody or an antigen-binding portion thereof that binds to an epitope of PD-1 comprising amino acid residues 69-90 and 122-140 of SEQ ID NO: 1 (e.g., a 12819 or 12865 antibody). In certain embodiments, the monoclonal antibody or antigen-binding portion binds to an epitope of PD-1 comprising amino acid residues 56-64, 69-90, and 122-140 of SEQ ID NO: 1 (e.g., a 12819 antibody). In certain embodiments, the antibody or portion binds to residues 69-75 (or a fragment thereof) of SEQ ID NO: 1 (e.g., a 12819 or 12865 antibody). In certain embodiments, the antibody or portion binds to residues 136-140 (or a fragment thereof) of SEQ ID NO: 1 (e.g., a 12819 or 12865 antibody). In some embodiments, the antibody or portion binds to residues 69-75 (or a fragment thereof) and residues 136-140 (or a fragment thereof) of SEQ ID NO: 1 (e.g., a 12819 or 12865 antibody).

In some embodiments, the anti-PD-1 antibody or antigen-binding portion of the invention has at least one of the following properties:
a) binds to human PD-1 with a $K_D$ of 750 pM or less;
b) binds to cynomolgus PD-1 with a $K_D$ of 7 nM or less; binds to mouse PD-1 with a $K_D$ of 1 nM or less;
d) does not bind to rat PD-1,
e) increases IL-2 secretion in an SEB whole blood assay;
f) increases IFN-γ secretion in a one-way mixed lymphocyte reaction assay;
g) inhibits the interaction of PD-1 with PD-L1 by at least 60% at a concentration of 10 µg/ml in a flow cytometric competition assay;
h) blocks binding of PD-L1 and PD-L2 to PD-1 by at least 90% at a concentration of 10 µg/ml as determined by Bio-Layer Interferometry analysis; and
i) inhibits tumor growth in vivo.

Examples of such an antibody include, without limitation, a 12819 antibody (having properties a-i); 12748, 12892, and 12777 antibodies (having at least properties a, b, and e-h); 12865 and 12796 antibodies (having at least properties a, b, e, f, and h), and 12760 and 13112 antibodies (having at least properties a, b, e, and f). In some embodiments, the anti-PD-1 antibody or antigen-binding portion of the invention has all of said properties. In some embodiments, the anti-PD-1 antibody or antigen-binding portion has at least properties a, b, and e-h. In some embodiments, the anti-PD-1 antibody or antigen-binding portion has at least properties a, b, e, f, and h. In some embodiments, the anti-PD-1 antibody or antigen-binding portion has at least properties a, b, e, and f.

Unless otherwise indicated, 12819, 12748, 12865, 12892, 12796, 12777, 12760 and 13112 each refers to a group of antibodies that have the same six CDRs and that share the first five digits in their ten-digit numerical designations. For example, 12748 includes antibody variants 12748.15381 and 12748.16124, which have the same six CDRs (as shown in Table 2). Each group of antibodies is expected to share the same or substantially the same biological properties.

In some embodiments, the anti-PD-1 antibody or antigen-binding portion of the invention does not compete for binding to PD-1 with pembrolizumab or nivolumab. In some embodiments, the anti-PD-1 antibody or antigen-binding portion of the invention does not bind to the same epitope as pembrolizumab or nivolumab; for example, the antibody or portion of the invention binds to one or more residues on PD-1 that are not bound by pembrolizumab or nivolumab.

In another aspect, the present invention provides pharmaceutical compositions comprising at least one anti-PD-1 antibody or antigen-binding portion thereof as described herein and a pharmaceutically acceptable excipient.

The present invention further provides isolated nucleic acid molecules comprising a nucleotide sequence that encodes the heavy chain or an antigen-binding portion thereof, a nucleotide sequence that encodes the light chain or an antigen-binding portion thereof, or both, of an anti-PD-1 antibody as described herein.

The present invention also provides vectors comprising such an isolated nucleic acid molecule, wherein said vector further comprises an expression control sequence.

The present invention also provide host cells comprising a nucleotide sequence that encodes the heavy chain or antigen-binding portion thereof, a nucleotide sequence that encodes the light chain or an antigen-binding portion thereof, or both, of an anti-PD-1 antibody as described herein.

The present invention also provides a method for producing an antibody or antigen-binding portion thereof as described herein, comprising providing a host cell that comprises a nucleotide sequence that encodes the heavy chain or an antigen-binding portion thereof and a nucleotide sequence that encodes the light chain or an antigen-binding portion thereof of an anti-PD-1 antibody as described herein, cultivating said host cell under conditions suitable for expression of the antibody or portion, and isolating the resulting antibody or portion.

The present invention also provides a bispecific binding molecule having the binding specificity of an anti-PD-1 antibody described herein and the binding specificity of another anti-PD-1 antibody (e.g., another anti-PD-1 antibody described herein) or an antibody that targets a different protein, such as another immune checkpoint protein, a cancer antigen, or another cell surface molecule whose activity mediates a disease condition such as cancer.

The present invention also provides a method for enhancing immunity in a patient (e.g., a human patient) in need thereof, comprising administering to said patient an anti-PD-1 antibody or an antigen-binding portion thereof, a pharmaceutical composition, or a bispecific binding molecule as described herein.

The present invention further provides a method for treating cancer in a patient (e.g., a human patient), comprising administering to said patient an anti-PD-1 antibody or an antigen-binding portion thereof, a pharmaceutical composition, or a bispecific binding molecule as described herein. In some embodiments, the cancer originates in a tissue selected from the group consisting of skin, lung, intestine, ovary, brain, prostate, kidney, soft tissues, hematopoietic system, head & neck, liver, bladder, breast, stomach, uterus and pancreas. The cancer may be, e.g., advanced or metastatic melanoma, non-small cell lung cancer, head and neck squamous cell cancer, renal cell carcinoma, or Hodgkin's lymphoma. In some embodiments, the method further comprises administering a chemotherapeutic agent, an anti-neoplastic agent, an anti-angiogenic agent, a tyrosine kinase inhibitor, or a PD-1 pathway inhibitor.

The present invention further provides antibodies or antigen-binding portions of the present invention for use in the aforementioned treatments, and the use of the antibodies or antigen-binding portions of the present invention for the manufacture of medicaments for the aforementioned treatments, i.e., treatment of a human in need thereof to enhance his/her immune system, and treatment of a human with cancer, such as one of the aforementioned cancers.

DETAILED DESCRIPTION OF THE INVENTION

Figure 1:
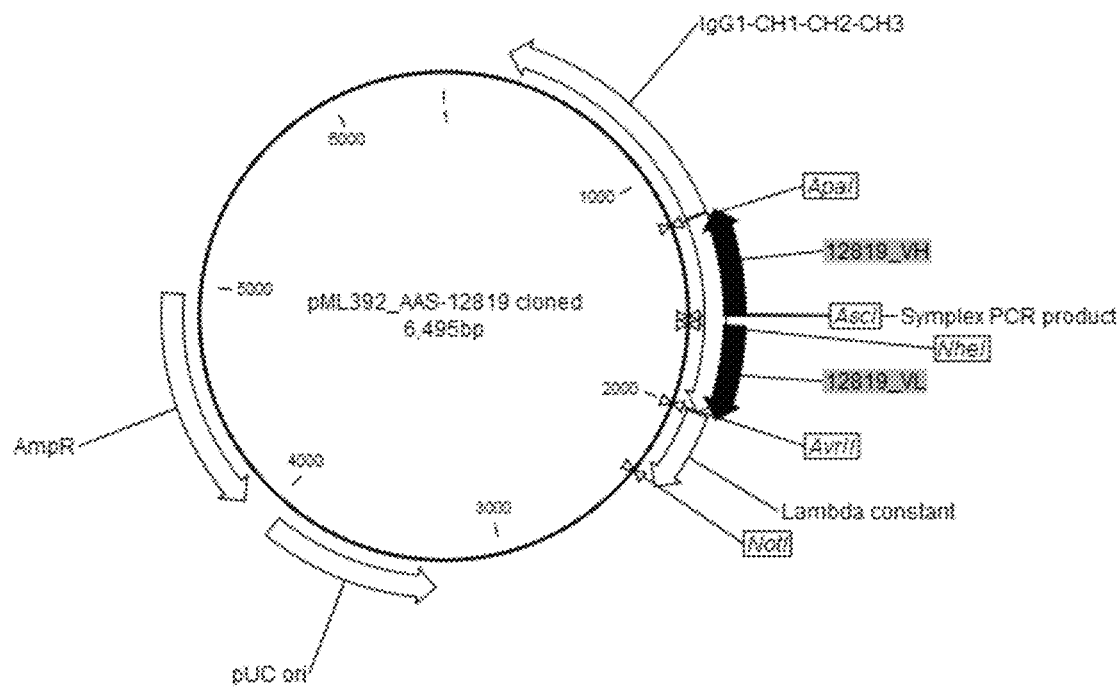
FIG. 1 shows a PCR product containing the $V_H$ and $V_L$ regions of the anti-PD-1 antibody AAS-12819 (shown in black) cloned in-frame with the corresponding human heavy chain IgG1-CH1-CH2-CH3 and human light chain lambda constant fragments, respectively. Restriction sites for this cloning are ApaI and AvrII. Restriction sites AscI and NheI are shown between the $V_H$ and $V_L$ 5'-ends. The plasmid origin of replication is depicted as pUC on and the gene conferring ampicillin-resistance is depicted as AmpR.

The present invention provides new anti-human PD-1 antibodies that can be used to enhance the immune system in a human patient, such as a cancer patient. Unless otherwise stated, as used herein, "PD-1" refers to human PD-1. A human PD-1 polypeptide sequence is available under Uniprot Accession No. Q15116 (PDCD1_HUMAN), shown here as SEQ ID NO: 1.

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain ($V_H$) and a heavy chain constant region (CH). Each light chain is composed of a light chain variable domain ($V_L$) and a light chain constant region (CL). The $V_H$ and $V_L$ domains can be subdivided further into regions of hypervariability, termed "complementarity determining regions" (CDRs), interspersed with regions that are more conserved, termed "framework regions" (FRs). Each $V_H$ and $V_L$ is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acid numbers in the heavy or light chain may be in accordance with IMGT® definitions (Lefranc et al., *Dev Comp Immunol* 27(1):55-77 (2003)); or the definitions of Kabat, *Sequences of Proteins of Immunological Interest* (National Institutes of Health, Bethesda, MD (1987 and 1991)); Chothia & Lesk, *J. Mol. Biol.* 196:901-917 (1987); or Chothia et al., *Nature* 342:878-883 (1989).

The term "recombinant antibody" refers to an antibody that is expressed from a cell or cell line comprising the nucleotide sequence(s) that encode the antibody, wherein said nucleotide sequence(s) are not naturally associated with the cell.

The term "isolated protein", "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

As used herein, the term "germline" refers to the nucleotide and amino acid sequences of antibody genes and gene segments as they are passed from parents to offspring via germ cells. Germline sequences are distinguished from the nucleotide sequences encoding antibodies in mature B cells, which have been altered by recombination and hypermutation events during the course of B cell maturation. An antibody that "utilizes" a particular germline sequence has a nucleotide or amino acid sequence that aligns with that germline nucleotide sequence or with the amino acid sequence that it specifies more closely than with any other germline nucleotide or amino acid sequence.

The term "affinity" refers to a measure of the attraction between an antigen and an antibody. The intrinsic attractiveness of the antibody for the antigen is typically expressed as the binding affinity equilibrium constant (K D) of a particular antibody-antigen interaction. An antibody is said to specifically bind to an antigen when the $K_D$ is 1 mM, preferably 100 nM. A $K_D$ binding affinity constant can be measured, e.g., by surface plasmon resonance (BIAcore™) or Bio-Layer Interferometry, for example using the ProteOn™ XPR36 SPR system from Bio-Rad or the Octet™ system.

The term "$k_{off}$" refers to the dissociation rate constant of a particular antibody-antigen interaction. A $k_{off}$ dissociation rate constant can be measured by Bio-Layer Interferometry, for example using the Octet™ system.

The term "epitope" as used herein refers to a portion (determinant) of an antigen that specifically binds to an antibody or a related molecule such as a bispecific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest or a relevant portion thereof (e.g., the ECD of PD-1), then screening for binding to the epitope.

One can determine whether an antibody binds to the same epitope as or competes for binding with an anti-PD-1 antibody of the invention by using methods known in the art, including, without limitation, competition assays, epitope binning, and alanine scanning. In some embodiments, the test antibody and an anti-PD-1 antibody of the invention bind to at least one common residue (e.g., at least two, three, four, or five common residues) on PD-1. In further embodiments, the contact residues on PD-1 are completely identical between the test antibody and the anti-PD-1 antibody of the invention. In one embodiment, one allows the anti-PD-1 antibody of the invention to bind to PD-1 under saturating conditions and then measures the ability of the test antibody to bind to PD-1. If the test antibody is able to bind to PD-1 at the same time as the reference anti-PD-1 antibody, then the test antibody binds to a different epitope than the reference anti-PD-1 antibody. However, if the test antibody is not able to bind to PD-1 at the same time, then the test antibody binds to the same epitope, an overlapping epitope, or an epitope that is in close proximity to the epitope bound by the anti-PD-1 antibody of the invention. This experiment can be performed using ELISA, RIA, BIACORE™, Bio-Layer Interferometry or flow cytometry. To test whether an anti-PD-1 antibody cross-competes with another anti-PD-1 antibody, one may use the competition method described above in two directions, i.e., determining if the known antibody blocks the test antibody and vice versa. Such cross-competition experiments may be performed, e.g., using an IBIS MX96 SPR instrument or the Octet™ system.

The term "chimeric antibody" refers in its broadest sense to an antibody that contains one or more regions from one antibody and one or more regions from one or more other antibodies, typically an antibody that is partially of human origin and partially of non-human origin, i.e., derived in part from a non-human animal, for example a mouse, rat or other rodent, or an avian such as a chicken. Chimeric antibodies are preferred over non-human antibodies in order to reduce the risk of a human anti-antibody response, e.g., a human anti-mouse antibody response in the case of a murine antibody. An example of a typical chimeric antibody is one in which the variable domain sequences are murine while the constant region sequences are human. In the case of a chimeric antibody, the non-human parts may be subjected to further alteration in order to humanize the antibody. The chimeric antibodies described herein have chicken variable domain sequences and human constant region sequences.

The term "humanize" refers to the fact that where an antibody is wholly or partially of non-human origin (for example, a murine or chicken antibody obtained from immunization of mice or chickens, respectively, with an antigen of interest, or a chimeric antibody based on such a murine or chicken antibody), it is possible to replace certain amino acids, in particular in the framework regions and constant regions of the heavy and light chains, in order to avoid or minimize an immune response in humans. Although it is not possible to precisely predict the immunogenicity and thereby the human anti-antibody response of a particular antibody, non-human antibodies tend to be more immunogenic in humans than human antibodies. Chimeric antibodies, where the foreign (e.g., rodent or avian) constant regions have been replaced with sequences of human origin, have been shown to be generally less immunogenic than antibodies of fully foreign origin, and the trend in therapeutic antibodies is towards humanized or fully human antibodies. Chimeric antibodies or other antibodies of non-human origin thus can be humanized to reduce the risk of a human anti-antibody response.

For chimeric antibodies, humanization typically involves modification of the framework regions of the variable domain sequences. Amino acid residues that are part of complementarity determining regions (CDRs) most often will not be altered in connection with humanization, although in certain cases it may be desirable to alter individual CDR amino acid residues, for example to remove a glycosylation site, a deamidation site, an aspartate isomerization site or an undesired cysteine or methionine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, preferably by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues.

Numerous methods for humanization of an antibody sequence are known in the art; see, e.g., the review by Almagro & Fransson, Front Biosci. 13:1619-1633 (2008). One commonly used method is CDR grafting, which for, e.g., a murine-derived chimeric antibody involves identification of human germline gene counterparts to the murine variable domain genes and grafting of the murine CDR sequences into this framework. The specificity of an antibody's interaction with a target antigen resides primarily in the amino acid residues located in the six CDRs of the heavy and light chain. The amino acid sequences within CDRs are therefore much more variable between individual antibodies than sequences outside of CDRs. Because CDR sequences are responsible for most antibody-antigen interactions, it is possible to express recombinant antibodies that mimic the properties of a specific naturally occurring antibody, or more generally any specific antibody with a given amino acid sequence, e.g., by constructing expression vectors that express CDR sequences from the specific antibody grafted into framework sequences from a different antibody. As a result, it is possible to "humanize" a non-human antibody and still substantially maintain the binding specificity and affinity of the original antibody. CDR grafting may be based on the Kabat CDR definitions, although a more recent publication (Magdelaine-Beuzelin et al., *Crit Rev. Oncol Hematol.* 64:210-225 (2007)) has suggested that the IMGT® definition (the international ImMunoGeneTics information system®, www.imgt.org) may improve the result of the humanization (see Lefranc et al., *Dev. Comp Immunol.* 27:55-77 (2003)).

In some cases, CDR grafting may reduce the binding specificity and affinity, and thus the biological activity, of a CDR-grafted non-human antibody as compared to the parent antibody from which the CDRs are obtained. Back mutations (sometimes referred to as "framework repair") may be introduced at selected positions of the CDR-grafted antibody, typically in the framework regions, in order to reestablish the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered.

An alternative humanization technique to CDR grafting and back mutation is resurfacing, in which non-surface exposed residues of non-human origin are retained, while surface residues are altered to human residues.

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., *Proc Natl Acad Sci USA*, 94:412-417 (1997), and the stepwise in vitro affinity maturation method of Wu et al., *Proc Natl Acad Sci USA* 95:6037-6042 (1998).

The term "antigen-binding portion" of an antibody (or simply "antibody portion"), as used herein, refers to one or more portions or fragments of an antibody that retain the ability to specifically bind to an antigen (e.g., human PD-1, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the $V_L$, $V_H$, $C_L$ and $C_H1$ domains (for example, the 12819.17149 and 12865.17150 Fab fragments described below); (ii) a F(ab') 2 fragment: a bivalent fragment comprising two Fab fragments linked by a disulfide bridge at the hinge region; (iii) an Fd fragment consisting of the $V_H$ and $C_H1$ domains; (iv) a Fv fragment consisting of the $V_L$ and $V_H$ domains of a single arm of an antibody, (v) a dAb fragment, which consists of a $V_H$ domain; and (vi) an isolated complementarity determining region (CDR) capable of specifically binding to an antigen. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ domains pair to form monovalent molecules (known as single chain Fv (scFv)). Also within the invention are antigen-binding molecules comprising a $V_H$ and/or a $V_L$. In the case of a $V_H$, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab') 2 fragments, can be prepared from whole antibodies using conventional techniques, such as papain or pepsin digestion of whole antibodies. Moreover, antibodies, antibody portions and immunoadhesion molecules can be obtained using standard recombinant DNA techniques, e.g., as described herein.

The class (isotype) and subclass of anti-PD-1 antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant regions of the heavy and/or light chains of the antibodies, comparing their amino acid sequences to the known amino acid sequences of various classes and subclasses of immunoglobulins, and determining the class and subclass of the antibodies.

When referring to particular amino acid residues in a given position of an antibody sequence, an indication of, e.g., "35S" refers to the position and residue, i.e., in this case indicating that a serine residue (S) is present in position 35 of the sequence. Similarly, an indication of, e.g., "13Q+35S" refers to the two residues in the respective positions.

Unless otherwise indicated, all antibody amino acid residue numbers referred to in this disclosure are those under the IMGT® numbering scheme.

Anti-PD-1 Antibodies

The present invention provides antibodies directed against PD-1, and antigen-binding portions thereof. The antibodies may be chimeric, with variable domains derived from chickens, and human constant regions, or may be humanized. The antibodies disclosed herein are in particular humanized antibodies.

The $V_H$ and $V_L$ amino acid sequences (SEQ ID NOs: 2 to 17) of eight selected humanized anti-PD-1 antibodies of the invention are shown further below in Table 4 (Example 4). For reference, the SEQ ID NOs. are provided below in Table 1.

The anti-PD-1 antibodies disclosed herein may be referred to by either a 5-digit number, e.g., "12819," or by a 10-digit number, e.g., "12819.15384." As used herein, the 5-digit number refers to all antibodies having the heavy and light chain CDR1-3 sequences shown for that number in Table 2, whereas the use of a 10-digit number refers to a particular humanized variant. For example, 12819.15384 is a particular humanized variant having the CDR sequences of a 12819 antibody as shown in Table 2. The 5-digit number encompasses, for example, antibodies that are identical to the 10-digit variants shown below in Table 1 except for some changes in the FRs (e.g., lacking residues SY at the N-terminus of the mature light chain, or having residues SS in lieu of SY). These modifications do not change the functional (e.g., antigen-binding) properties of the antibodies.

TABLE 1

SEQ ID NOs for the amino acid sequences of the heavy and light chain variable domains of humanized anti-PD-1 antibodies

| Antibody | $V_H$ | $V_L$ |
|---|---|---|
| 12819.15384 | 2 | 3 |
| 12748.15381 | 4 | 5 |
| 12748.16124 | 4 | 66 |
| 12865.15377 | 6 | 7 |
| 12892.15378 | 8 | 9 |
| 12796.15376 | 10 | 11 |
| 12777.15382 | 12 | 13 |
| 12760.15375 | 14 | 15 |
| 13112.15380 | 16 | 17 |

Table 2 below provides the SEQ ID NOs for the heavy and light chain CDR amino acid sequences of the antibodies.

TABLE 2

SEQ ID NOs for the CDR amino acid sequences of anti-PD-1 antibodies

| Antibody | H-CDR1 | H-CDR2 | H-CDR3 | L-CDR1 | L-CDR2 | L-CDR3 |
|---|---|---|---|---|---|---|
| 12819 | 18 | 19 | 20 | 21 | 22 | 23 |
| 12748 | 24 | 25 | 26 | 27 | 28 | 29 |
| 12865 | 30 | 31 | 32 | 33 | 34 | 35 |
| 12892 | 36 | 37 | 38 | 39 | 40 | 41 |
| 12796 | 42 | 43 | 44 | 45 | 46 | 47 |
| 12777 | 48 | 49 | 50 | 51 | 52 | 53 |
| 12760 | 54 | 55 | 56 | 57 | 58 | 59 |
| 13112 | 60 | 61 | 62 | 63 | 64 | 65 |

In some embodiments, the anti-PD-1 antibody is selected from the group consisting of:
a) an antibody whose H-CDR1-3 comprise the amino acid sequences of SEQ ID NOs: 18-20, respectively;
b) an antibody whose heavy chain variable domain ($V_H$) is at least 90% identical in sequence to the amino acid sequence of SEQ ID NO: 2;
c) an antibody whose $V_H$ comprises the amino acid sequence of SEQ ID NO: 2; d) an antibody whose heavy chain (HC) comprises the amino acid sequences of SEQ ID NOs: 2 and 67;
e) an antibody whose L-CDR1-3 comprise the amino acid sequences of SEQ ID NOs: 21-23, respectively;
f) an antibody whose light chain variable domain ($V_L$) is at least 90% identical in sequence to the amino acid sequence of SEQ ID NO: 3;
g) an antibody whose $V_L$ comprises the amino acid sequence of SEQ ID NO: 3;
h) an antibody whose light chain (LC) comprises the amino acid sequences of SEQ ID NOs: 3 and 68;
i) an antibody whose H-CDR1-3 and L-CDR1-3 comprise the amino acid sequences of SEQ ID NOs: 18-23, respectively;
j) an antibody whose $V_H$ is at least 90% identical in sequence to the amino acid sequence of SEQ ID NO: 2 and whose $V_L$ is at least 90% identical in sequence to the amino acid sequence of SEQ ID NO: 3;
k) an antibody whose $V_H$ comprises the amino acid sequence of SEQ ID NO: 2 and whose $V_L$ comprises the amino acid sequence of SEQ ID NO: 3; and
l) an antibody whose HC comprises the amino acid sequences of SEQ ID NOs: 2 and 67 and whose LC comprises the amino acid sequences of SEQ ID NOs: 3 and 68.

In some embodiments, the anti-PD-1 antibody is selected from the group consisting of:
a) an antibody whose H-CDR1-3 comprise the amino acid sequences of SEQ ID NOs: 24-26, respectively;
b) an antibody whose heavy chain variable domain ($V_H$) is at least 90% identical in sequence to the amino acid sequence of SEQ ID NO: 4;
c) an antibody whose $V_H$ comprises the amino acid sequence of SEQ ID NO: 4;
d) an antibody whose heavy chain (HC) comprises the amino acid sequences of SEQ ID NOs: 4 and 67;
e) an antibody whose L-CDR1-3 comprise the amino acid sequences of SEQ ID NOs: 27-29, respectively;
f) an antibody whose light chain variable domain ($V_L$) is at least 90% identical in sequence to the amino acid sequence of SEQ ID NO: 5 or 66;
g) an antibody whose $V_L$ comprises the amino acid sequence of SEQ ID NO: 5 or 66;
h) an antibody whose light chain (LC) comprises the amino acid sequences of SEQ ID NO: 5 or 66 and the amino acid sequence of SEQ ID NO: 68;
i) an antibody whose H-CDR1-3 and L-CDR1-3 comprise the amino acid sequences of SEQ ID NOs: 24-29, respectively;
j) an antibody whose $V_H$ is at least 90% identical in sequence to the amino acid sequence of SEQ ID NO: 4 and whose $V_L$ is at least 90% identical in sequence to the amino acid sequence of SEQ ID NO: 5 or 66;
k) an antibody whose $V_H$ comprises the amino acid sequence of SEQ ID NO: 4 and whose $V_L$ comprises the amino acid sequence of SEQ ID NO: 5 or 66; and
l) an antibody whose HC comprises the amino acid sequences of SEQ ID NOs: 4 and 67 and whose LC comprises the amino acid sequences of SEQ ID NO: 5 or 66 and SEQ ID NO: 68.

In some embodiments, the anti-PD-1 antibody is selected from the group consisting of:
a) an antibody whose H-CDR1-3 comprise the amino acid sequences of SEQ ID NOs: 30-32, respectively;
b) an antibody whose heavy chain variable domain ($V_H$) is at least 90% identical in sequence to the amino acid sequence of SEQ ID NO: 6;
c) an antibody whose $V_H$ comprises the amino acid sequence of SEQ ID NO: 6;
d) an antibody whose heavy chain (HC) comprises the amino acid sequences of SEQ ID NOs: 6 and 67;
e) an antibody whose L-CDR1-3 comprise the amino acid sequences of SEQ ID NOs: 33-35, respectively;
f) an antibody whose light chain variable domain ($V_L$) is at least 90% identical in sequence to the amino acid sequence of SEQ ID NO: 7;
g) an antibody whose $V_L$ comprises the amino acid sequence of SEQ ID NO: 7; h) an antibody whose light chain (LC) comprises the amino acid sequences of SEQ ID NO: 7 and 68;

i) an antibody whose H-CDR1-3 and L-CDR1-3 comprise the amino acid sequences of SEQ ID NOs: 30-35, respectively;
j) an antibody whose $V_H$ is at least 90% identical in sequence to the amino acid sequence of SEQ ID NO: 6 and whose $V_L$ is at least 90% identical in sequence to the amino acid sequence of SEQ ID NO: 7;
k) an antibody whose $V_H$ comprises the amino acid sequence of SEQ ID NO: 6 and whose $V_L$ comprises the amino acid sequence of SEQ ID NO: 7; and
l) an antibody whose HC comprises the amino acid sequences of SEQ ID NOs: 6 and 67 and whose LC comprises the amino acid sequences of SEQ ID NOs: 7 and 68.

In some embodiments, the anti-PD-1 antibody is selected from the group consisting of:
a) an antibody whose H-CDR1-3 comprise the amino acid sequences of SEQ ID NOs: 36-38, respectively;
b) an antibody whose heavy chain variable domain ($V_H$) is at least 90% identical in sequence to the amino acid sequence of SEQ ID NO: 8;
c) an antibody whose $V_H$ comprises the amino acid sequence of SEQ ID NO: 8;
d) an antibody whose heavy chain (HC) comprises the amino acid sequences of SEQ ID NOs: 8 and 67;
e) an antibody whose L-CDR1-3 comprise the amino acid sequences of SEQ ID NOs: 39-41, respectively;
f) an antibody whose light chain variable domain ($V_L$) is at least 90% identical in sequence to the amino acid sequence of SEQ ID NO: 9;
g) an antibody whose $V_L$ comprises the amino acid sequence of SEQ ID NO: 9;
h) an antibody whose light chain (LC) comprises the amino acid sequences of SEQ ID NOs: 9 and 68;
i) an antibody whose H-CDR1-3 and L-CDR1-3 comprise the amino acid sequences of SEQ ID NOs: 36-41, respectively;
j) an antibody whose $V_H$ is at least 90% identical in sequence to the amino acid sequence of SEQ ID NO: 8 and whose $V_L$ is at least 90% identical in sequence to the amino acid sequence of SEQ ID NO: 9;
k) an antibody whose $V_H$ comprises the amino acid sequence of SEQ ID NO: 8 and whose $V_L$ comprises the amino acid sequence of SEQ ID NO: 9; and
l) an antibody whose HC comprises the amino acid sequences of SEQ ID NOs: 8 and 67 and whose LC comprises the amino acid sequences of SEQ ID NOs: 9 and 68.

In some embodiments, the anti-PD-1 antibody is selected from the group consisting of:
a) an antibody whose H-CDR1-3 comprise the amino acid sequences of SEQ ID NOs:42-44, respectively;
b) an antibody whose heavy chain variable domain ($V_H$) is at least 90% identical in sequence to the amino acid sequence of SEQ ID NO: 10;
c) an antibody whose $V_H$ comprises the amino acid sequence of SEQ ID NO: 10;
d) an antibody whose heavy chain (HC) comprises the amino acid sequences of SEQ ID NOs: 10 and 67;
e) an antibody whose L-CDR1-3 comprise the amino acid sequences of SEQ ID NOs: 45-47, respectively;
f) an antibody whose light chain variable domain ($V_L$) is at least 90% identical in sequence to the amino acid sequence of SEQ ID NO: 11;
g) an antibody whose $V_L$ comprises the amino acid sequence of SEQ ID NO: 11;
h) an antibody whose light chain (LC) comprises the amino acid sequences of SEQ ID NOs: 11 and 68;
i) an antibody whose H-CDR1-3 and L-CDR1-3 comprise the amino acid sequences of SEQ ID NOs: 42-47, respectively;
j) an antibody whose $V_H$ is at least 90% identical in sequence to the amino acid sequence of SEQ ID NO: 10 and whose $V_L$ is at least 90% identical in sequence to the amino acid sequence of SEQ ID NO: 11;
k) an antibody whose $V_H$ comprises the amino acid sequence of SEQ ID NO: 10 and whose $V_L$ comprises the amino acid sequence of SEQ ID NO: 11; and
l) an antibody whose HC comprises the amino acid sequences of SEQ ID NOs: 10 and 67 and whose LC comprises the amino acid sequences of SEQ ID NOs: 11 and 68.

In some embodiments, the anti-PD-1 antibody is selected from the group consisting of:
a) an antibody whose H-CDR1-3 comprise the amino acid sequences of SEQ ID NOs: 48-50, respectively;
b) an antibody whose heavy chain variable domain ($V_H$) is at least 90% identical in sequence to the amino acid sequence of SEQ ID NO: 12;
c) an antibody whose $V_H$ comprises the amino acid sequence of SEQ ID NO: 12;
d) an antibody whose heavy chain (HC) comprises the amino acid sequences of SEQ ID NOs: 12 and 67;
e) an antibody whose L-CDR1-3 comprise the amino acid sequences of SEQ ID NOs: 51-53, respectively;
f) an antibody whose light chain variable domain ($V_L$) is at least 90% identical in sequence to the amino acid sequence of SEQ ID NO: 13;
g) an antibody whose $V_L$ comprises the amino acid sequence of SEQ ID NO: 13;
h) an antibody whose light chain (LC) comprises the amino acid sequences of SEQ ID NOs: 13 and 68;
i) an antibody whose H-CDR1-3 and L-CDR1-3 comprise the amino acid sequences of SEQ ID NOs: 48-53, respectively;
j) an antibody whose $V_H$ is at least 90% identical in sequence to the amino acid sequence of SEQ ID NO: 12 and whose $V_L$ is at least 90% identical in sequence to the amino acid sequence of SEQ ID NO: 13;
k) an antibody whose $V_H$ comprises the amino acid sequence of SEQ ID NO: 12 and whose $V_L$ comprises the amino acid sequence of SEQ ID NO: 13; and
l) an antibody whose HC comprises the amino acid sequences of SEQ ID NOs: 12 and 67 and whose LC comprises the amino acid sequences of SEQ ID NOs: 13 and 68.

In some embodiments, the anti-PD-1 antibody is selected from the group consisting of:
a) an antibody whose H-CDR1-3 comprise the amino acid sequences of SEQ ID NOs: 54-56, respectively;
b) an antibody whose heavy chain variable domain ($V_H$) is at least 90% identical in sequence to the amino acid sequence of SEQ ID NO: 14;
c) an antibody whose $V_H$ comprises the amino acid sequence of SEQ ID NO: 14;
d) an antibody whose heavy chain (HC) comprises the amino acid sequences of SEQ ID NOs: 14 and 67;
e) an antibody whose L-CDR1-3 comprise the amino acid sequences of SEQ ID NOs: 57-59, respectively;
f) an antibody whose light chain variable domain ($V_L$) is at least 90% identical in sequence to the amino acid sequence of SEQ ID NO: 15;

g) an antibody whose $V_L$ comprises the amino acid sequence of SEQ ID NO: 15;
h) an antibody whose light chain (LC) comprises the amino acid sequences of SEQ ID NOs: 15 and 68;
i) an antibody whose H-CDR1-3 and L-CDR1-3 comprise the amino acid sequences of SEQ ID NOs: 54-59, respectively;
j) an antibody whose $V_H$ is at least 90% identical in sequence to the amino acid sequence of SEQ ID NO: 14 and whose $V_L$ is at least 90% identical in sequence to the amino acid sequence of SEQ ID NO: 15;
k) an antibody whose $V_H$ comprises the amino acid sequence of SEQ ID NO: 14 and whose $V_L$ comprises the amino acid sequence of SEQ ID NO: 15; and
l) an antibody whose HC comprises the amino acid sequences of SEQ ID NOs: 14 and 67 and whose LC comprises the amino acid sequences of SEQ ID NOs: 15 and 68.

In some embodiments, the anti-PD-1 antibody is selected from the group consisting of:
a) an antibody whose H-CDR1-3 comprise the amino acid sequences of SEQ ID NOs: 60-62, respectively;
b) an antibody whose heavy chain variable domain ($V_H$) is at least 90% identical in sequence to the amino acid sequence of SEQ ID NO: 16;
c) an antibody whose $V_H$ comprises the amino acid sequence of SEQ ID NO: 16;
d) an antibody whose heavy chain (HC) comprises the amino acid sequences of SEQ ID NOs: 16 and 67;
e) an antibody whose L-CDR1-3 comprise the amino acid sequences of SEQ ID NOs: 63-65, respectively;
f) an antibody whose light chain variable domain ($V_L$) is at least 90% identical in sequence to the amino acid sequence of SEQ ID NO: 17;
g) an antibody whose $V_L$ comprises the amino acid sequence of SEQ ID NO: 17;
h) an antibody whose light chain (LC) comprises the amino acid sequences of SEQ ID NOs: 17 and 68;
i) an antibody whose H-CDR1-3 and L-CDR1-3 comprise the amino acid sequences of SEQ ID NOs: 60-65, respectively;
j) an antibody whose $V_H$ is at least 90% identical in sequence to the amino acid sequence of SEQ ID NO: 16 and whose $V_L$ is at least 90% identical in sequence to the amino acid sequence of SEQ ID NO: 17;
k) an antibody whose $V_H$ comprises the amino acid sequence of SEQ ID NO: 16 and whose $V_L$ comprises the amino acid sequence of SEQ ID NO: 17;
l) an antibody whose HC comprises the amino acid sequences of SEQ ID NOs: 16 and 67 and whose LC comprises the amino acid sequences of SEQ ID NOs: 17 and 68.

In some embodiments, the anti-PD-1 antibody or an antigen-binding portion thereof comprises the H-CDR1-3 and L-CDR1-3 amino acid sequences of a 12819 antibody (e.g., antibody 12819.15384).

In some embodiments, the anti-PD-1 antibody or an antigen-binding portion thereof comprises the H-CDR1-3 and L-CDR1-3 amino acid sequences of a 12748 antibody (e.g., antibody 12748.15381 or antibody 12748.16124).

In some embodiments, the anti-PD-1 antibody or an antigen-binding portion thereof comprises the H-CDR1-3 and L-CDR1-3 amino acid sequences of a 12865 antibody (e.g., antibody 12865.15377).

In some embodiments, the anti-PD-1 antibody or an antigen-binding portion thereof comprises the H-CDR1-3 and L-CDR1-3 amino acid sequences of a 12892 antibody (e.g., antibody 12892.15378).

In some embodiments, the anti-PD-1 antibody or an antigen-binding portion thereof comprises the H-CDR1-3 and L-CDR1-3 amino acid sequences of a 12796 antibody (e.g., antibody 12796.15376).

In some embodiments, the anti-PD-1 antibody or an antigen-binding portion thereof comprises the H-CDR1-3 and L-CDR1-3 amino acid sequences of a 12777 antibody (e.g., antibody 12777.15382).

In some embodiments, the anti-PD-1 antibody or an antigen-binding portion thereof comprises the H-CDR1-3 and L-CDR1-3 amino acid sequences of a 12760 antibody (e.g., antibody 12760.15375).

In some embodiments, the anti-PD-1 antibody or an antigen-binding portion thereof comprises the H-CDR1-3 and L-CDR1-3 amino acid sequences of a 13112 antibody (e.g., antibody 13112.15380).

In another embodiment, the anti-PD-1 antibody or an antigen-binding portion thereof has a $V_H$ and a $V_L$ that are at least 90% (e.g., at least 91%, 92%, 93%, 94%, 95%, 96%, 97%, 98%, or 99%) identical in amino acid sequence to the $V_H$ and $V_L$, respectively, of any one of antibodies 12819.15384, 12748.15381, 12748.16124, 12865.15377, 12892.15378, 12796.15376, 12777.15382, 12760.15375, and 13112.15380.

In some embodiments, the anti-PD-1 antibody or an antigen-binding portion thereof has a $V_H$ and a $V_L$ that comprise the $V_H$ and $V_L$ amino acid sequences, respectively, of any one of antibodies 12819.15384, 12748.15381, 12748.16124, 12865.15377, 12892.15378, 12796.15376, 12777.15382, 12760.15375, and 13112.15380

In some embodiments, the anti-PD-1 antibody or an antigen-binding portion thereof comprises the H-CDR1-3 and L-CDR1-3 amino acid sequences of:
a) SEQ ID NOs: 18, 19, 20, 21, 22, and 23, respectively;
b) SEQ ID NOs: 24, 25, 26, 27, 28, and 29, respectively;
c) SEQ ID NOs: 30, 31, 32, 33, 34, and 35, respectively;
d) SEQ ID NOs: 36, 37, 38, 39, 40, and 41, respectively;
e) SEQ ID NOs: 42, 43, 44, 45, 46, and 47, respectively;
f) SEQ ID NOs: 48, 49, 50, 51, 52, and 53, respectively;
g) SEQ ID NOs: 54, 55, 56, 57, 58, and 59, respectively; or
h) SEQ ID NOs: 60, 61, 62, 63, 64, and 65, respectively.

In some embodiments, the anti-PD-1 antibody or an antigen-binding portion thereof comprises a $V_H$ that is 80%, 85%, 90%, 91%, 92%, 93%, 94%, 95%, 96%, 97%, 98%, or 99% identical, and a $V_L$ that is 80%, 85%, 90%, 91%, 92%, 93%, 94%, 95%, 96%, 97%, 98%, or 99% identical, to the amino acid sequences of:
a) SEQ ID NOs: 2 and 3, respectively;
b) SEQ ID NOs: 4 and 5, respectively;
c) SEQ ID NOs: 4 and 66, respectively;
d) SEQ ID NOs: 6 and 7, respectively;
e) SEQ ID NOs: 8 and 9, respectively;
f) SEQ ID NOs: 10 and 11, respectively;
g) SEQ ID NOs: 12 and 13, respectively;
h) SEQ ID NOs: 14 and 15, respectively; or
i) SEQ ID NOs: 16 and 17, respectively.

In some embodiments, the anti-PD-1 antibody or an antigen-binding portion thereof comprises a $V_H$ and a $V_L$ that are the amino acid sequences of:
a) SEQ ID NOs: 2 and 3, respectively;
b) SEQ ID NOs: 4 and 5, respectively;
c) SEQ ID NOs: 4 and 66, respectively;
d) SEQ ID NOs: 6 and 7, respectively;
e) SEQ ID NOs: 8 and 9, respectively;

f) SEQ ID NOs: 10 and 11, respectively;
g) SEQ ID NOs: 12 and 13, respectively;
h) SEQ ID NOs: 14 and 15, respectively; or
i) SEQ ID NOs: 16 and 17, respectively.

In some embodiments, the anti-PD-1 antibody comprises:
a) an HC comprising the amino acid sequences of SEQ ID NOs: 2 and 67 and an LC comprising the amino acid sequences of SEQ ID NOs: 3 and 68;
b) an HC comprising the amino acid sequences of SEQ ID NOs: 4 and 67 and an LC comprising the amino acid sequences of SEQ ID NOs: 5 and 68;
c) an HC comprising the amino acid sequences of SEQ ID NOs: 4 and 67 and an LC comprising the amino acid sequences of SEQ ID NOs: 66 and 68;
d) an HC comprising the amino acid sequences of SEQ ID NOs: 6 and 67 and an LC comprising the amino acid sequences of SEQ ID NOs: 7 and 68;
e) an HC comprising the amino acid sequences of SEQ ID NOs: 8 and 67 and an LC comprising the amino acid sequences of SEQ ID NOs: 9 and 68;
f) an HC comprising the amino acid sequences of SEQ ID NOs: 10 and 67 and an LC comprising the amino acid sequences of SEQ ID NOs: 11 and 68;
g) an HC comprising the amino acid sequences of SEQ ID NOs: 12 and 67 and an LC comprising the amino acid sequences of SEQ ID NOs: 13 and 68;
h) an HC comprising the amino acid sequences of SEQ ID NOs: 14 and 67 and an LC comprising the amino acid sequences of SEQ ID NOs: 15 and 68; or
i) an HC comprising the amino acid sequences of SEQ ID NOs: 16 and 67 and an LC comprising the amino acid sequences of SEQ ID NOs: 17 and 68.

In some embodiments, the anti-PD-1 antibody comprises:
a) an HC consisting of the amino acid sequences of SEQ ID NOs: 2 and 67 and an LC consisting of the amino acid sequences of SEQ ID NOs: 3 and 68;
b) an HC consisting of the amino acid sequences of SEQ ID NOs: 4 and 67 and an LC consisting of the amino acid sequences of SEQ ID NOs: 5 and 68;
c) an HC consisting of the amino acid sequences of SEQ ID NOs: 4 and 67 and an LC consisting of the amino acid sequences of SEQ ID NOs: 66 and 68;
d) an HC consisting of the amino acid sequences of SEQ ID NOs: 6 and 67 and an LC consisting of the amino acid sequences of SEQ ID NOs: 7 and 68;
e) an HC consisting of the amino acid sequences of SEQ ID NOs: 8 and 67 and an LC consisting of the amino acid sequences of SEQ ID NOs: 9 and 68;
f) an HC consisting of the amino acid sequences of SEQ ID NOs: 10 and 67 and an LC consisting of the amino acid sequences of SEQ ID NOs: 11 and 68;
g) an HC consisting of the amino acid sequences of SEQ ID NOs: 12 and 67 and an LC consisting of the amino acid sequences of SEQ ID NOs: 13 and 68;
h) an HC consisting of the amino acid sequences of SEQ ID NOs: 14 and 67 and an LC consisting of the amino acid sequences of SEQ ID NOs: 15 and 68; or
i) an HC consisting of the amino acid sequences of SEQ ID NOs: 16 and 67 and an LC consisting of the amino acid sequences of SEQ ID NOs: 17 and 68.

In some embodiments, any of the anti-PD-1 antibodies or antigen-binding portions described herein may have at least one of the following properties:
a) binds to human PD-1 with a $K_D$ of 750 pM or less;
b) binds to cynomolgus PD-1 with a $K_D$ of 7 nM or less;
c) binds to mouse PD-1 with a $K_D$ of 1 nM or less;
d) does not bind to rat PD-1,
e) increases IL-2 secretion in an SEB whole blood assay;
f) increases IFN-γ secretion in a one-way mixed lymphocyte reaction assay;
g) inhibits the interaction of PD-1 with PD-L1 by at least 60% at a concentration of 10 μg/ml in a flow cytometric competition assay;
h) blocks binding of PD-L1 and PD-L2 to PD-1 by at least 90% at a concentration of 10 μg/ml as determined by Bio-Layer Interferometry analysis; and
i) inhibits tumor growth in vivo.

In some embodiments, any of the anti-PD-1 antibodies or antigen-binding portions described herein may bind to human PD-1 with a $K_D$ of at least 900, at least 850, at least 800, at least 750, at least 700, at least 650, at least 600, at least 550, at least 500, at least 450, at least 400, at least 350, at least 300, at least 250, at least 200, at least 150, at least 100, at least 50, at least 40, at least 30, or at least 20 pM. In certain embodiments, the $K_D$ is determined using surface plasmon resonance. In particular embodiments, the anti-PD-1 antibodies or antigen-binding portions bind to human PD-1 with a higher affinity than nivolumab, pembrolizumab, or both.

In some embodiments, any of the anti-PD-1 antibodies or antigen-binding portions described herein may bind to cynomolgus PD-1 (SEQ ID NO: 89) with a $K_D$ of at least 9000, at least 8000, at least 7000, at least 6000, at least 5000, at least 4000, at least 3000, at least 2500, at least 2000, at least 1500, at least 1000, at least 900, at least 800, at least 700, at least 600, at least 500, at least 400, at least 300, at least 200, at least 100, at least 75, at least 50, at least 25, at least 20, at least 15, at least 10, or at least 5 pM. In certain embodiments, the $K_D$ is determined using surface plasmon resonance.

In some embodiments, any of the anti-PD-1 antibodies or antigen-binding portions described herein may bind to mouse PD-1 (SEQ ID NO: 91) with a $K_D$ of at least 1000, at least 950, at least 900, or at least 850 pM. In certain embodiments, the $K_D$ is determined using surface plasmon resonance.

In some embodiments, any of the anti-PD-1 antibodies or antigen-binding portions described herein may inhibit the interaction of PD-1 with PD-L1 by at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% at a concentration of 10 μg/ml in a flow cytometric competition assay. In certain embodiments, the anti-PD-1 antibodies or antigen-binding portions may inhibit the interaction of PD-1 with PD-L1 by at least 83%.

In some embodiments, any of the anti-PD-1 antibodies or antigen-binding portions described herein may block binding of PD-L1 and PD-L2 to PD-1 by at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100% at a concentration of 10 μg/ml as determined by Bio-Layer Interferometry analysis. In certain embodiments, the anti-PD-1 antibodies or antigen-binding portions block binding of PD-L1 and PD-L2 to PD-1 by at least 90%.

In some embodiments, any of the anti-PD-1 antibodies or antigen-binding portions described herein may compete or cross-compete for binding to PD-1 with 12865, 12892, and 12777 antibodies (e.g., antibodies 12865.15377, 12892.15378, and 12777.15382). In some embodiments, any of the anti-PD-1 antibodies or antigen-binding portions described herein may compete or cross-compete for binding to PD-1 with a 12819 antibody (e.g., antibody 12819.15384). In some embodiments, any of the anti-PD-1 antibodies or antigen-binding portions described herein may compete or cross-compete for binding to PD-1 with 12760 and 13112 antibodies (e.g., antibodies 12760.15375 and 13112.15380).

In some embodiments, an anti-PD-1 antibody of the invention, or an antigen-binding portion thereof, binds to an epitope of PD-1 that includes at least one (e.g., at least one, at least two, at least three, at least four, or at least five) of the following residues of SEQ ID NO: 1: V44, V64, L128, P130, K131, A132, E136, and T145. In certain embodiments, the antibody or antigen-binding portion binds to an epitope of PD-1 that includes residues V64, L128, P130, K131, and A132 of SEQ ID NO: 1 (such as a 12819 antibody, e.g., antibody 12819.15384). In certain embodiments, the antibody or antigen-binding portion binds to an epitope of PD-1 that includes residues K131 and E136 of SEQ ID NO: 1 (such as a 12865 antibody, e.g., antibody 12865.15377). In certain embodiments, the antibody or antigen-binding portion binds to an epitope of PD-1 that includes residues V44 and T145 of SEQ ID NO: 1 (such as a 13112 antibody, e.g., antibody 13112.15380).

In some embodiments, an anti-PD-1 antibody of the invention, or an antigen-binding portion thereof, binds to an epitope of PD-1 that comprises residues 56-64, 69-90, and/or 122-140 of SEQ ID NO: 1. In certain embodiments, the antibody or antigen-binding portion binds to an epitope of PD-1 that comprises residues 69-90 and 122-140 of SEQ ID NO: 1 (such as 12819 and 12865 antibodies, e.g., antibodies 12819.15384 and 12865.15377). In certain embodiments, the antibody or antigen-binding portion binds to an epitope of PD-1 that comprises residues 56-64, 69-90, and 122-140 of SEQ ID NO: 1 (e.g., a 12819 antibody). In certain embodiments, the antibody or antigen-binding portion binds to an epitope of PD-1 that comprises residues 69-90 and 122-140 of SEQ ID NO: 1 (e.g., a 12865 antibody). In some embodiments, the antibody or portion binds to residues 69-75 (or a fragment thereof, such as a one, two, three, four, five, or six residue fragment), of SEQ ID NO: 1 (such as 12819 and 12865 antibodies, e.g., antibodies 12819.15384 and 12865.15377). In some embodiments, the antibody or portion binds to residues 136-140 (or a fragment thereof, such as a one, two, three, or four residue fragment) of SEQ ID NO: 1 (such as 12819 and 12865 antibodies, e.g., antibodies 12819.15384 and 12865.15377). In some embodiments, the antibody or portion binds to residues 69-75 (or a fragment thereof) and residues 136-140 (or a fragment thereof) of SEQ ID NO: 1, (such as 12819 and 12865 antibodies, e.g., antibodies 12819.15384 and 12865.15377). An epitope with any combination of the above residues is also contemplated.

In some embodiments, an amino acid sequence comprising a PD-1 epitope as described herein can be used as an immunogen (e.g., administered to an animal or as an antigen for screening antibody libraries) to generate or identify anti-PD-1 antibodies or antigen-binding portions thereof that bind to said epitope.

The class of an anti-PD-1 antibody obtained by the methods described herein may be changed or switched with another class or subclass. In one aspect of the invention, a nucleic acid molecule encoding $V_L$ or $V_H$ is isolated using methods well-known in the art such that it does not include nucleic acid sequences encoding $C_L$ or $C_H$. The nucleic acid molecules encoding $V_L$ or $V_H$ then are operatively linked to a nucleic acid sequence encoding a $C_L$ or $C_H$, respectively, from a different class of immunoglobulin molecule. This may be achieved using a vector or nucleic acid molecule that comprises a $C_L$ or $C_H$ chain, as described above. For example, an anti-PD-1 antibody that was originally IgM may be class switched to IgG. Further, the class switching may be used to convert one IgG subclass to another, e.g., from $IgG_1$ to $IgG_2$. A κ light chain constant region can be changed to a λ light chain constant region. A preferred method for producing an antibody of the invention with a desired Ig isotype comprises the steps of isolating a nucleic acid molecule encoding the heavy chain of an anti-PD-1 antibody and a nucleic acid molecule encoding the light chain of an anti-PD-1 antibody, obtaining the variable domain of the heavy chain, ligating the variable domain of the heavy chain with the constant region of a heavy chain of the desired isotype, expressing the light chain and the ligated heavy chain in a cell, and collecting the anti-PD-1 antibody with the desired isotype.

The anti-PD-1 antibody of the invention can be an IgG, an IgM, an IgE, an IgA, or an IgD molecule, but is typically of the IgG isotype, e.g., of IgG subclass $IgG_1$, $IgG_{2a}$ or $IgG_{2b}$, $IgG_3$ or $IgG_4$. In one embodiment, the antibody is an $IgG_1$. In another embodiment, the antibody is an $IgG_4$.

In one embodiment, the anti-PD-1 antibody may comprise at least one mutation in the Fc region. A number of different Fc mutations are known, where these mutations provide altered effector function. For example, in many cases it will be desirable to reduce or eliminate effector function, e.g., where ligand/receptor interactions are undesired or in the case of antibody-drug conjugates.

In one embodiment, the anti-PD-1 antibody comprises at least one mutation in the Fc region that reduces effector function. Fc region amino acid positions that may be advantageous to mutate in order to reduce effector function include one or more of positions 228, 233, 234 and 235, where amino acid positions are numbered according to the IMGT® numbering scheme.

In one embodiment, one or both of the amino acid residues at positions 234 and 235 may be mutated, for example from Leu to Ala (L234A/L235A). These mutations reduce effector function of the Fc region of $IgG_1$ antibodies. Additionally or alternatively, the amino acid residue at position 228 may be mutated, for example to Pro. In another embodiment, the amino acid residue at position 233 may be mutated, e.g., to Pro, the amino acid residue at position 234 may be mutated, e.g., to Val, and/or the amino acid residue at position 235 may be mutated, e.g., to Ala. The amino acid positions are numbered according to the IMGT® numbering scheme.

In another embodiment, where the antibody is of the $IgG_4$ subclass, it may comprise the mutation S228P, i.e., having a proline in position 228, where the amino acid position is numbered according to the IMGT® numbering scheme. This mutation is known to reduce undesired Fab arm exchange.

In certain embodiments, an antibody or antigen-binding portion thereof of the invention may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al., Human Antibodies and Hybridomas 6:93-101 (1995)) and use of a cysteine residue, a marker peptide and a C-terminal polyhistidine tag to make bivalent and biotinylated scFv molecules (Kipriyanov et al., *Mol. Immunol.* 31:1047-1058 (1994)). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

In another embodiment, a fusion antibody or immunoadhesin may be made that comprises all or a portion of an anti-PD-1 antibody of the invention linked to another polypeptide. In certain embodiments, only the variable domains of the anti-PD-1 antibody are linked to the polypeptide. In certain embodiments, the $V_H$ domain of an anti-PD-1 antibody is linked to a first polypeptide, while the $V_L$ domain of an anti-PD-1 antibody is linked to a second polypeptide that associates with the first polypeptide in a manner such that the $V_H$ and $V_L$ domains can interact with one another to form an antigen-binding site. In another preferred embodiment, the $V_H$ domain is separated from the $V_L$ domain by a linker such that the $V_H$ and $V_L$ domains can interact with one another (e.g., single-chain antibodies). The $V_H$-linker-$V_L$ antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody (scFv), the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ domains joined by the flexible linker. See, e.g., Bird et al., *Science* 242:423-426 (1988); Huston et al., *Proc. Natl. Acad. Sci. USA* 85:5879-5883 (1988); and McCafferty et al., *Nature* 348:552-554 (1990). The single chain antibody may be monovalent, if only a single $V_H$ and $V_L$ are used; bivalent, if two $V_H$ and $V_L$ are used; or polyvalent, if more than two $V_H$ and $V_L$ are used. Bispecific or polyvalent antibodies may be generated that bind specifically to human PD-1 and to another molecule, for instance.

In other embodiments, other modified antibodies may be prepared using anti-PD-1 antibody-encoding nucleic acid molecules. For instance, "kappa bodies" (Ill et al., *Protein Eng.* 10:949-57 (1997)), "minibodies" (Martin et al., *EMBO J.* 13:5303-9 (1994)), "diabodies" (Holliger et al., *Proc. Natl. Acad. Sci. USA* 90:6444-6448 (1993)), or "Janusins" (Traunecker et al., EMBO J. 10:3655-3659 (1991) and Traunecker et al., *Int. J. Cancer* (Suppl.) 7:51-52 (1992)) may be prepared using standard molecular biological techniques following the teachings of the specification.

An anti-PD-1 antibody or antigen-binding portion of the invention can be derivatized or linked to another molecule (e.g., another peptide or protein). In general, the antibodies or portions thereof are derivatized such that PD-1 binding is not affected adversely by the derivatization or labeling. Accordingly, the antibodies and antibody portions of the invention are intended to include both intact and modified forms of the human anti-PD-1 antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available, e.g., from Pierce Chemical Company, Rockford, Il.

An anti-PD-1 antibody can also be derivatized with a chemical group such as polyethylene glycol (PEG), a methyl or ethyl group, or a carbohydrate group. These groups may be useful to improve the biological characteristics of the antibody, e.g., to increase serum half-life.

An antibody according to the present invention may also be labeled. As used herein, the terms "label" or "labeled" refer to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In certain embodiments, the antibodies of the invention may be present in a neutral form (including zwitter ionic forms) or as a positively or negatively-charged species. In some embodiments, the antibodies may be complexed with a counterion to form a pharmaceutically acceptable salt.

The term "pharmaceutically acceptable salt" refers to a complex comprising one or more antibodies and one or more counterions, wherein the counterions are derived from pharmaceutically acceptable inorganic and organic acids and bases.

Bispecific Binding Molecules

In a further aspect, the invention provides a bispecific binding molecule having the binding specificity of an anti-PD-1 antibody described herein and the binding specificity of another anti-PD-1 antibody (e.g., another anti-PD-1 antibody described herein) or an antibody that targets a different protein, such as another immune checkpoint protein, a cancer antigen, or another cell surface molecule whose activity mediates a disease condition such as cancer. Such bispecific binding molecules are known in the art, and examples of different types of bispecific binding molecules are given elsewhere herein.

Nucleic Acid Molecules and Vectors

The present invention also provides nucleic acid molecules and sequences encoding anti-PD-1 antibodies or antigen-binding portions thereof described herein. In some embodiments, different nucleic acid molecules encode the heavy chain and light chain amino acid sequences of the anti-PD-1 antibody or an antigen-binding portion thereof. In other embodiments, the same nucleic acid molecule encodes the heavy chain and light chain amino acid sequences of the anti-PD-1 antibody or an antigen-binding portion thereof.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single and double stranded forms.

The invention also provides nucleotide sequences that are at least 70%, 75%, 80%, 85%, 90%, 95%, 97%, 98% or 99% identical to one or more nucleotide sequences recited herein, e.g., to a nucleotide sequence selected from the group consisting of SEQ ID NOs: 69-88. The term "percent sequence identity" in the context of nucleic acid sequences refers to the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wisconsin. FASTA, which includes, e.g., the programs FASTA2 and FASTA3, provides alignments and percent sequence identity of the regions of the best overlap between the query and search sequences (see, e.g., Pearson, *Methods Enzymol.* 183:63-98 (1990); Pearson, *Methods Mol. Biol.* 132:185-219 (2000); Pearson, *Methods Enzymol.* 266:227-258 (1996); and Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In one aspect, the invention provides a nucleic acid molecule comprising a nucleotide sequence selected from the group consisting of SEQ ID NOs: 69-88.

In any of the above embodiments, the nucleic acid molecules may be isolated.

In a further aspect, the present invention provides a vector suitable for expressing one of the chains of an antibody or antigen-binding portion thereof as described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The invention provides vectors comprising nucleic acid molecules that encode the heavy chain of an anti-PD-1 antibody of the invention or an antigen-binding portion thereof, the light chain of an anti-PD-1 antibody of the invention or an antigen-binding portion thereof, or both the heavy and light chains of an anti-PD-1 antibody of the invention or an antigen-binding portion thereof. The invention further provides vectors comprising nucleic acid molecules encoding fusion proteins, modified antibodies, antibody fragments, and probes thereof.

A nucleic acid molecule encoding the heavy and/or light chain of an anti-PD-1 antibody or antigen-binding portion thereof of the invention can be isolated from any source that produces such an antibody or portion. In various embodiments, the nucleic acid molecules are isolated from B cells that express an anti-PD-1 antibody isolated from an animal immunized with a human PD-1 antigen, or from an immortalized cell produced from such a B cell. Methods of isolating nucleic acids encoding an antibody are well-known in the art. mRNA may be isolated and used to produce cDNA for use in polymerase chain reaction (PCR) or cDNA cloning of antibody genes. In certain embodiments, a nucleic acid molecule of the invention can be synthesized rather than isolated.

In some embodiments, a nucleic acid molecule of the invention can comprise a nucleotide sequence encoding a $V_H$ domain from an anti-PD-1 antibody or antigen-binding portion of the invention joined in-frame to a nucleotide sequence encoding a heavy chain constant region from any source. Similarly, a nucleic acid molecule of the invention can comprise a nucleotide sequence encoding a $V_L$ domain from an anti-PD-1 antibody or antigen-binding portion of the invention joined in-frame to a nucleotide sequence encoding a light chain constant region from any source.

In a further aspect of the invention, nucleic acid molecules encoding the variable domain of the heavy ($V_H$) and/or light ($V_L$) chains may be "converted" to full-length antibody genes. In one embodiment, nucleic acid molecules encoding the $V_H$ or $V_L$ domains are converted to full-length antibody genes by insertion into an expression vector already encoding heavy chain constant ($C_H$) or light chain constant ($C_L$) domains, respectively, such that the $V_H$ segment is operatively linked to the $C_H$ segment(s) within the vector, and/or the $V_L$ segment is operatively linked to the $C_L$ segment within the vector. In another embodiment, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleic acid molecules encoding the full-length heavy and/or light chains may then be expressed from a cell into which they have been introduced and the anti-PD-1 antibody isolated.

The nucleic acid molecules may be used to recombinantly express large quantities of anti-PD-1 antibodies. The nucleic acid molecules also may be used to produce chimeric antibodies, bispecific antibodies, single chain antibodies, immunoadhesins, diabodies, mutated antibodies and antibody derivatives, as described herein.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-PD-1 antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of the anti-PD-1 antibodies or antigen-binding portions thereof of the invention as described herein.

In another embodiment, the nucleic acid molecules and vectors may be used to make mutated anti-PD-1 antibodies. The antibodies may be mutated in the variable domains of the heavy and/or light chains, e.g., to alter a binding property of the antibody. For example, a mutation may be made in one or more of the CDRs to increase or decrease the $K_D$ of the anti-PD-1 antibody, to increase or decrease k off, or to alter the binding specificity of the antibody. In another embodiment, one or more mutations are made at an amino acid residue that is known to be changed compared to the germline in a monoclonal antibody of the invention. The mutations may be made in a CDR or framework region of a variable domain, or in a constant region. In a preferred embodiment, the mutations are made in a variable domain. In some embodiments, one or more mutations are made at an amino acid residue that is known to be changed compared to the germline in a CDR or framework region of a variable domain of an antibody or antigen-binding portion thereof of the invention.

In another embodiment, the framework region(s) are mutated so that the resulting framework region(s) have the amino acid sequence of the corresponding germline gene. A mutation may be made in a framework region or constant region to increase the half-life of the anti-PD-1 antibody. See, e.g., PCT Publication WO 00/09560. A mutation in a framework region or constant region also can be made to alter the immunogenicity of the antibody, and/or to provide a site for covalent or non-covalent binding to another molecule. According to the invention, a single antibody may have mutations in any one or more of the CDRs or framework regions of the variable domain or in the constant region.

In some embodiments, the anti-PD-1 antibodies of the invention or antigen-binding portions thereof are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody coding sequence may be ligated into a vector such that transcriptional and translational control sequences within the vector serve their intended function of regulating the transcription and translation of the antibody coding sequence. The expression vector and expression control sequences may be chosen to be compatible with the expression host cell used. The antibody light chain coding sequence and the antibody heavy chain coding sequence can be inserted into separate vectors, and may be operatively linked to the same or different expression control sequences (e.g., promoters). In one embodiment, both coding sequences are inserted into the same expression vector, and may be operatively linked to the same expression control sequences (e.g., a common promoter), to separate identical expression control sequences (e.g., promoters), or to different expression control sequences (e.g., promoters). The antibody coding sequences may be inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. The HC- and LC-encoding genes in such vectors may contain intron sequences that will result in enhanced overall antibody protein yields by stabilizing the related mRNA. The intron sequences are flanked by splice donor and splice acceptor sites, which determine where RNA splicing will occur. Location of intron sequences can be either in variable or constant regions of the antibody chains, or in both variable and constant regions when multiple introns are used. Polyadenylation and transcription termination may occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention may carry regulatory sequences that control the expression of the antibody chain genes in a host cell. It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants, are known in the art. See, e.g., U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr-host cells with methotrexate selection/amplification), the neo gene (for G418 selection), and the glutamate synthetase gene.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

Host Cells and Methods of Antibody and Antibody Composition Production

An additional aspect of the invention relates to methods for producing the antibody compositions and antibodies and antigen-binding portions thereof of the invention. One embodiment of this aspect of the invention relates to a method for producing an antibody as defined herein, comprising providing a recombinant host cell capable of expressing the antibody, cultivating said host cell under conditions suitable for expression of the antibody, and isolating the resulting antibody. Antibodies produced by such expression in such recombinant host cells are referred to herein as "recombinant antibodies". The invention also provides progeny cells of such host cells, and antibodies produced by same.

The term "recombinant host cell" (or simply "host cell"), as used herein, means a cell into which a recombinant expression vector has been introduced. The invention provides host cells that may comprise, e.g., a vector according to the invention described above. The invention also provides host cells that comprise, e.g., a nucleotide sequence encoding the heavy chain or an antigen-binding portion thereof, a nucleotide sequence encoding the light chain or an antigen-binding portion thereof, or both, of an anti-PD-1 antibody or antigen-binding portion thereof of the invention. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding anti-PD-1 antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected by determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention or antigen-binding portions thereof from production cell lines can be enhanced using a number of known techniques. For example, the glutamine synthetase gene expression system (the GS system) is a common approach for enhancing expression under certain conditions. The GS system is discussed in whole or part in connection with EP Patents 0 216 846, 0 256 055, 0 323 997 and 0 338 841.

It is likely that antibodies expressed by different cell lines or in transgenic animals will have different glycosylation patterns from each other. However, all antibodies encoded by the nucleic acid molecules provided herein, or comprising the amino acid sequences provided herein are part of the instant invention, regardless of the glycosylation state of the antibodies, and more generally, regardless of the presence or absence of post-translational modification(s).

Pharmaceutical Compositions

Another aspect of the invention is a pharmaceutical composition comprising as an active ingredient (or as the sole active ingredient) an anti-PD-1 antibody or antigen-binding portion thereof or anti-PD-1 antibody composition of the invention. The pharmaceutical composition may comprise any anti-PD-1 antibody composition or antibody or antigen-binding portion thereof as described herein. In some embodiments, the compositions are intended for amelioration, prevention, and/or treatment of a PD-1-related disorder (e.g., a disorder characterized by overexpression or overactivity of PD-1) and/or cancer. In some embodiments, the compositions are intended for activation of the immune system. In certain embodiments, the compositions are intended for amelioration, prevention, and/or treatment of cancer originating in tissues such as skin, lung, intestine, ovary, brain, prostate, kidney, soft tissues, the hematopoietic system, head & neck, liver, bladder, breast, stomach, uterus and pancreas.

Generally, the antibodies of the invention or antigen-binding portions thereof are suitable to be administered as a formulation in association with one or more pharmaceutically acceptable excipient(s), e.g., as described below.

Pharmaceutical compositions of the invention will comprise one or more anti-PD-1 antibodies or binding portions of the invention, e.g., one or two anti-PD-1 antibodies or binding portions. In one embodiment, the composition comprises a single anti-PD-1 antibody of the invention or binding portion thereof.

In another embodiment, the pharmaceutical composition may comprise at least one anti-PD-1 antibody or antigen-binding portion thereof, e.g., one anti-PD-1 antibody or portion, and one or more additional antibodies that target one or more relevant cell surface receptors, e.g., one or more cancer-relevant receptors.

The term "excipient" is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in *Remington's Pharmaceutical Sciences*, 19th Edition (Mack Publishing Company, 1995). Pharmaceutical compositions are preferably manufactured under GMP (good manufacturing practices) conditions.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the antibodies and antigen-binding portions of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, and intrasynovial injection or infusions; and kidney dialytic infusion techniques. Regional perfusion is also contemplated. Preferred embodiments include the intravenous and the subcutaneous routes.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-PD-1 antibody or antigen-binding portion thereof or anti-PD-1 antibody composition in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin, and/or by using modified-release coatings (e.g., slow-release coatings).

The antibodies of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurised container, pump, spray, atomiser (preferably an atomiser using electrohydrodynamics to produce a fine mist), or nebuliser, with or without the use of a suitable propellant, or as nasal drops.

The pressurised container, pump, spray, atomizer, or nebuliser generally contains a solution or suspension of an antibody of the invention comprising, for example, a suitable agent for dispersing, solubilising, or extending release of the active, a propellant(s) as solvent.

Prior to use in a dry powder or suspension formulation, the drug product is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound of the invention, a suitable powder base and a performance modifier.

A suitable solution formulation for use in an atomiser using electrohydrodynamics to produce a fine mist may contain a suitable dose of the antibody of the invention per actuation and the actuation volume may for example vary from 1 µL to 100 µL.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

The antibodies and antibody portions of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Therapeutic Uses of Antibodies and Compositions of the Invention

In one aspect, the anti-PD-1 antibodies and antigen-binding portions thereof, anti-PD-1 compositions, and bi-specific binding molecules of the invention are used to enhance or activate the immune system in a human in need thereof. In some embodiments, the patient has a condition characterized by overexpression or overactivity of PD-1. In some embodiments, the patient is immune-suppressed. In certain embodiments, the antibody or antigen-binding portion thereof, composition, or bi-specific binding molecule pharmaceutical composition is for use in the treatment of cancer, e.g., cancers that originate in tissues such as skin, lung, intestine, ovary, brain, prostate, kidney, soft tissues, hematopoietic system, head & neck, liver, bladder, breast, stomach, uterus and pancreas, and any cancers or other conditions which rely on PD-1 activity or in which the patient expresses or overexpresses PD-L1, PD-L2, or both. Cancers treated by the anti-PD-1 antibodies, antigen-binding portions thereof, anti-PD-1 antibody compositions, and/or bi-specific binding molecules of the invention may include, e.g., melanoma (such as advanced melanoma, or unresectable or metastatic melanoma), non-small cell lung cancer, bladder cancer, head and neck squamous cell carcinoma, ovarian cancer, colorectal cancer, Hodgkin's lymphoma, and renal cell carcinoma (RCC).

In some embodiments, cancers treated by the anti-PD-1 antibodies, antigen-binding portions, anti-PD-1 compositions, and/or bi-specific binding molecules of the invention may include, e.g., melanoma (e.g., advanced or metastatic melanoma), non-small cell lung cancer, head and neck squamous cell cancer, renal cell carcinoma, Hodgkin's lymphoma, non-Hodgkin's lymphoma, glioblastoma, glioma, squamous cell lung cancer, small-cell lung cancer, hepatocellular carcinoma, bladder cancer, upper urinary tract cancer, esophageal cancer, gastroesophageal junction cancer, gastric cancer, liver cancer, colon cancer, colorectal carcinoma, multiple myeloma, sarcomas, acute myeloid leukemia, chronic myeloid leukemia, myelodysplastic syndrome, nasopharyngeal cancer, chronic lymphocytic leukemia, acute lymphoblastic leukemia, small lymphocytic lymphoma, ovarian cancer, gastrointestinal cancer, primary peritoneal cancer, fallopian tube cancer, urothelial cancer, HTLV-associated T-cell leukemia/lymphoma, prostate cancer, genitourinary cancer, meningioma, adrenocortical cancer, gliosarcoma, fibrosarcoma, kidney cancer, breast cancer, pancreatic cancer, endometrial cancer, skin basal cell cancer, cancer of the appendix, biliary tract cancer, salivary gland cancer, advanced Merkel cell cancer, diffuse large B cell lymphoma, follicular lymphoma, mesothelioma, and solid tumors.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

"Therapeutically effective amount" refers to the amount of the therapeutic agent being administered that will relieve to some extent one or more of the symptoms of the disorder being treated. A therapeutically effective amount of an anti-cancer therapeutic may result in tumor shrinkage, increased survival, elimination of cancer cells, decreased disease progression, reversal of metastasis, or other clinical endpoints desired by healthcare professionals.

The antibody compositions or antibodies or antigen-binding portions thereof of the invention may be administered alone or in combination with one or more other drugs or antibodies (or as any combination thereof). The pharmaceutical compositions, methods and uses of the invention thus also encompass embodiments of combinations (co-administration) with other active agents, as detailed below.

As used herein, the terms "co-administration", "co-administered" and "in combination with," referring to the antibody compositions and antibodies and antigen-binding portions thereof of the invention with one or more other therapeutic agents, is intended to mean, and does refer to and include the following:
  simultaneous administration of such combination of antibody composition/antibody/antigen-binding portion of the invention and therapeutic agent(s) to a patient in need of treatment, when such components are formulated together into a single dosage form which releases said components at substantially the same time to said patient,
  substantially simultaneous administration of such combination of antibody composition/antibody/antigen-binding portion of the invention and therapeutic agent(s) to a patient in need of treatment, when such components are formulated apart from each other into separate dosage forms which are taken at substantially the same time by said patient, whereupon said components are released at substantially the same time to said patient,
  sequential administration of such combination of antibody composition/antibody/antigen-binding portion of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and
  sequential administration of such combination of antibody composition/antibody/antigen-binding portion of the invention and therapeutic agent(s) to a patient in need of treatment, when such components are formulated together into a single dosage form which releases said components in a controlled manner whereupon they are concurrently, consecutively, and/or overlappingly released at the same and/or different times to said patient,
where each part may be administered by either the same or a different route.

The antibody compositions and antibodies and antigen-binding portions thereof of the invention may be administered without additional therapeutic treatments, i.e., as a stand-alone therapy. Alternatively, treatment with the antibody compositions and antibodies and antigen-binding portions thereof of the invention may include at least one additional therapeutic treatment (combination therapy). In some embodiments, the antibody composition or antibody or antigen-binding portion thereof may be co-administered or formulated with another medication/drug for the treatment of cancer. The additional therapeutic treatment may comprise, e.g., a chemotherapeutic, anti-neoplastic, or anti-angiogenic agent, a different anti-cancer antibody, and/or radiation therapy.

By combining the antibody compositions, antibodies, or antigen-binding portions of the invention with agents known to induce terminal differentiation of cancer cells, the effect may be improved further. Such compounds may, for example, be selected from the group consisting of retinoic acid, trans-retinoic acids, cis-retinoic acids, phenylbutyrate, nerve growth factor, dimethyl sulfoxide, active form vitamin D3, peroxisome proliferator-activated receptor gamma, 12-O-tetradecanoylphorbol 13-acetate, hexamethylene-bis-acetamide, transforming growth factor-beta, butyric acid, cyclic AMP, and vesnarinone. In some embodiments, the compound is selected from the group consisting of retinoic acid, phenylbutyrate, all-trans-retinoic acid and active form vitamin D.

Pharmaceutical articles comprising an anti-PD-1 antibody composition or anti-PD-1 antibody or antigen-binding portion thereof of the invention and at least one other agent (e.g., a chemotherapeutic, anti-neoplastic, or anti-angiogenic agent) may be used as a combination treatment for simultaneous, separate or successive administration in cancer therapy. The other agent may by any agent suitable for treatment of the particular cancer in question, for example, an agent selected from the group consisting of alkylating agents, e.g., platinum derivatives such as cisplatin, carboplatin and/or oxaliplatin; plant alkoids, e.g., paclitaxel, docetaxel and/or irinotecan; antitumor antibiotics, e.g., doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; and/or antimetabolites, e.g., fluorouracil and/or other fluoropyrimidines.

An anti-PD-1 antibody or antigen-binding portion thereof or anti-PD-1 antibody composition of the invention may also be used in combination with other anti-cancer therapies such as vaccines, cytokines, enzyme inhibitors and T cell therapies. In the case of a vaccine, it may, e.g., be a protein, peptide or DNA vaccine containing one or more antigens which are relevant for the cancer being treated, or a vaccine comprising dendritic cells along with an antigen. Suitable cytokines include, for example, IL-2, IFN-gamma and GM-CSF. An example of a type of enzyme inhibitor that has anti-cancer activity is an indoleamine-2,3-dioxygenase (IDO) inhibitor, for example 1-methyl-D-tryptophan (1-D-MT). Adoptive T cell therapy refers to various immunotherapy techniques that involve expanding or engineering patients' own T cells to recognize and attack their tumors.

It is also contemplated that an anti-PD-1 antibody or antigen-binding portion thereof or anti-PD-1 antibody composition of the invention may be used in adjunctive therapy in connection with tyrosine kinase inhibitors. These are synthetic, mainly quinazoline-derived, low molecular weight molecules that interact with the intracellular tyrosine kinase domain of receptors and inhibiting ligand-induced receptor phosphorylation by competing for the intracellular Mg-ATP binding site.

In some embodiments, the antibody composition or antibody or antigen-binding portion thereof may be used in combination with another medication/drug that mediates immune system activation, including, but not limited to, an agent that mediates the expression or activity of A2AR, BLTA, B7-H3, B7-H4, CTLA-4, CD27, CD28, CD40, CD55, CD73, CD122, CD137, CD160, CGEN-15049, CHK1, CHK2, CTLA-3, CEACAM (e.g., CEACAM-1 and/or CEACAM-5), GAL9, GITR, HVEM, ICOS, IDO, KIR, LAIR1, LAG-3, OX40, TIGIT, TIM-3, TGFR-beta, VISTA and/or 2B4. In certain embodiments, the agent is an antibody or an antigen-binding fragment thereof that binds to one of the above molecules. In certain embodiments, the antibody composition or antibody or antigen-binding portion thereof of the invention may be administered in combination with a CTLA-4 inhibitor (e.g., an anti-CTLA-4 antibody such as tremelimumab or ipilimumab). In one embodiment, the antibody composition or antibody or antigen-binding portion thereof of the invention may be administered in combination with ipilimumab.

In certain aspects, the antibodies and antigen-binding portions of the invention may be administered in combination with another inhibitor of the PD-1 pathway, which may target PD-1 or one or more of its ligands. Examples of such inhibitors include other anti-PD-1 antibodies, anti-PD-L1 antibodies, and anti-PD-L2 antibodies. In some embodiments, an antibody composition, antibody, and/or antigen-binding portion of the invention may be administered in combination with pembrolizumab and/or nivolumab.

It is understood that the antibody compositions and antibodies and antigen-binding portions thereof of the invention may be used in a method of treatment as described herein, may be for use in a treatment as described herein, and/or may be for use in the manufacture of a medicament for a treatment as described herein.

Dose and Route of Administration

The antibody compositions of the invention will be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen are adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

It is contemplated that a suitable dose of an antibody composition of the invention will be in the range of 0.1-100 mg/kg, such as about 0.5-50 mg/kg, e.g., about 1-20 mg/kg. The antibody composition may for example be administered in a dosage of at least 0.25 mg/kg, e.g., at least 0.5 mg/kg, such as at least 1 mg/kg, e.g., at least 1.5 mg/kg, such as at least 2 mg/kg, e.g., at least 3 mg/kg, such as at least 4 mg/kg, e.g., at least 5 mg/kg; and e.g., up to at most 50 mg/kg, such as up to at the most 30 mg/kg, e.g., up to at the most 20 mg/kg, such as up to at the most 15 mg/kg. Administration will normally be repeated at suitable intervals, e.g., once every week, once every two weeks, once every three weeks, or once every four weeks, and for as long as deemed appropriate by the responsible doctor, who may optionally increase or decrease the dosage as necessary.

An effective amount for tumor therapy may be measured by its ability to stabilize disease progression and/or ameliorate symptoms in a patient, and preferably to reverse disease progression, e.g., by reducing tumor size. The ability of an antibody or composition of the invention to inhibit cancer may be evaluated by in vitro assays, e.g., as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

Diagnostic Uses and Compositions

The antibodies of the present invention also are useful in diagnostic processes (e.g., in vitro, ex vivo). For example, the antibodies can be used to detect and/or measure the level of PD-1 in a sample from a patient (e.g., a tissue sample, or a body fluid sample such as an inflammatory exudate, blood, serum, bowel fluid, saliva, or urine). Suitable detection and measurement methods include immunological methods such as flow cytometry, enzyme-linked immunosorbent assays (ELISA), chemiluminescence assays, radioimmunoassay, and immunohistology. The invention further encompasses kits (e.g., diagnostic kits) comprising the antibodies described herein.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

In order that this invention may be better understood, the following examples are set forth. These examples are for purposes of illustration only and are not to be construed as limiting the scope of the invention in any manner.

EXAMPLES

Example 1: Cloning of Anti-PD-1 Antibodies from Chicken B Cells

Cloning of chicken-derived antibody genes from antibody-secreting B cells (ASC) was performed by means of the Symplex™ antibody discovery technology. Briefly, ASC were isolated from lymphoid organs of chickens that had been immunized with PD-1 antigen, as soluble protein antigen and/or in its native cell membrane-bound form displayed on eukaryotic cells. Staining of the ASC with fluorescently labelled antibodies allowed discrimination of ASC from other cells (e.g., T cells, naïve B cells, monocytes, etc.) prior to sorting into PCR vessels. Single ASC sorting was performed by flow cytometry. Subsequently, the Symplex™ procedure was conducted to generate PCR products containing cognate $V_H$ and $V_L$ pairs for each sorted B cell as described hereafter.

Linkage of $V_H$ and $V_L$ coding sequences was performed on the sorted ASC, facilitating cognate pairing of the sequences. The process utilized a two-step PCR procedure based on a one-step multiplex overlap-extension RT-PCR followed by nested PCR. The principle for linkage of cognate $V_H$ and $V_L$ sequences using the Symplex™ technology is described in detail in WO 2005/042774; WO 2008/104184; WO 2010/022738, and Meijer et al., *J Mol Biol* 358(3):764-72 (2006). Briefly, cognate $V_H$ and $V_L$ amplified fragments are joined by overlap-extension PCR in a so-called nested PCR step. In the subsequent process, PCR products are pooled prior to cloning into a plasmid vector. This is done in such a way that the cloned DNA fragments encoding the variable domains of the chicken antibody can be expressed as a full chimeric antibody from a single plasmid expression construct in transfected mammalian cells. Consequently, it is possible to screen cell supernatants for chimeric antibodies exhibiting specific binding to the PD-1 antigen.

Materials and Methods

The Symplex™ technology as described in the publications listed above was modified to amplify $V_L$ and $V_H$ from sorted chicken B-cells. Cloning of a functional expression construct was done in two steps, as described below.

Step 1. The amplified PCR products containing the paired $V_H$ and $V_L$ fragments were amplified in a nested PCR reaction. This allowed for addition of flanking restriction enzyme recognition sites for ApaI and AvrII at each end. Since the cognate $V_H$ and $V_L$ sequences were paired in a single PCR product from each sorted ASC, cloning of the PCR products was performed after pooling all the PCR fragments. The plasmid pML392 was constructed to receive the Symplex™ PCR products by digestion of the corresponding restriction sites ApaI and AvrII. The resulting ligation of pooled PCR products and pML392 is shown in FIG. 1. Here the insertion of the PCR product placed the $V_H$ and $V_L$ sequences in front of human $C_H1$-$C_H2$-$C_H3$ and lambda constant cDNA regions, respectively, so that full length heavy and light chain reading frames were obtained.

Figure 2:
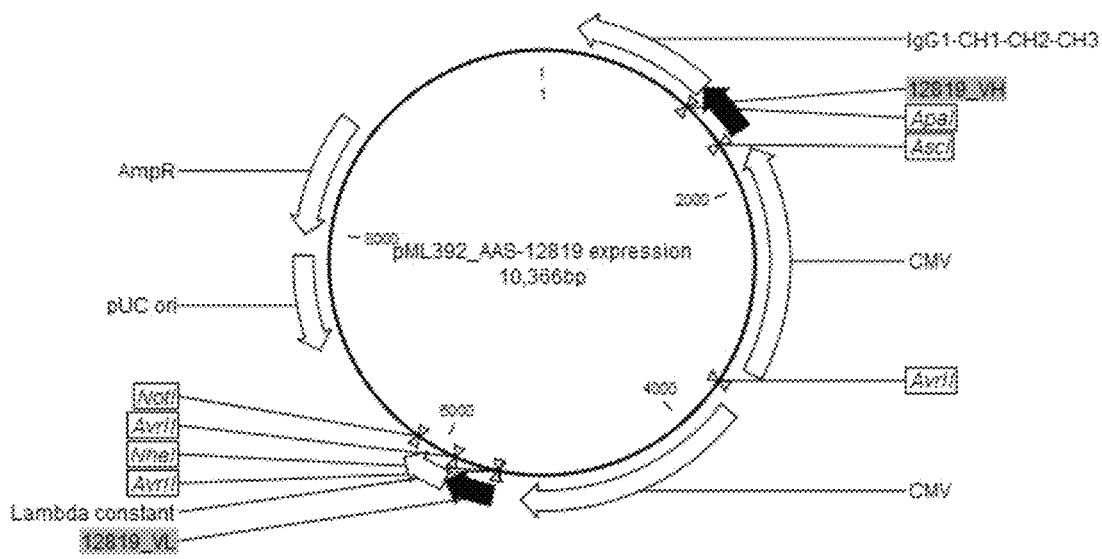
FIG. 2 shows an expression construct with a double CMV promoter inserted between 5'-ends of $V_H$ and $V_L$ using AscI and NheI restriction sites. $V_H$ and $V_L$ sequences are depicted in black, other annotated genetic elements are depicted in white.

Step 2. In the initial constructs, the two reading frames encoding heavy and light chain sequences were placed head-to-head and separated by a DNA sequence that contained restriction enzyme recognition sites for AscI and NheI. By insertion of a corresponding AscI/NheI-digested double CMV promoter DNA fragment including 5"-UTRs and signal peptides between the two 5"-ends of the heavy and light chain genes, a complete expression construct was obtained as depicted in FIG. 2.

Example 2: Cloning of Anti-PD-1 Reference Antibody Analogues

This example briefly explains how reference analogues of the anti-PD-1 antibodies nivolumab and pembrolizumab were generated.

Amino acid sequences encoding the variable heavy and light chain domains of antibody analogues of nivolumab and pembrolizumab were obtained from the IMGT® website imgt.org/mAb-DB/; see Table 3 below. The protein sequences were reverse translated to DNA sequences with human codon usage. The corresponding DNA sequences were then gene synthesized and cloned into expression vectors containing constant human $IgG_4$ heavy chain or kappa light chain domains, resulting in expression of full-length antibodies. To prevent Fab arm exchange, the serine residue at position 228 was substituted with proline (Angel et al., *Mol. Immunol.* 30:105-108 (1993)). CHO cells were transfected with the corresponding expression plasmids using a standard protein expression system. The corresponding antibody supernatants were purified using standard protein A purification column chromatography.

TABLE 3

Gene-synthesized antibody analogues

| Antibody | Research code | Antibody format | Reference Website |
|---|---|---|---|
| Pembrolizumab/ KEYTRUDA ® | MK-3475 | Recombinant IgG4, S228P | imgt.org/mAb-DB/mAbcard?Abld = 472 |
| Nivolumab/ OPDIVO ® | BMS-936558, MDX-1106, ONO-4538 | Recombinant IgG4, S228P | imgt.org/mAb-DB/mAbcard?Abld = 424 |

Example 3: Screening of Antibody Repertoires for Binding to Cell Surface-Expressed PD-1

Cloned antibodies of the anti-PD-1 repertoire were individually transfected and expressed in HEK293 cells using 293fectin™ Transfection reagent (Invitrogen, Cat. No. 12347-019) in 384-well format, and antibody-containing supernatants were collected on day 6 after transfection.

For cell-based antibody screening, CHO-S cells were transfected in 384-well format to express full-length human PD-1 using the FreeStyle™ MAX reagent (Invitrogen, Cat. No. 16447-100), and non-transfected cells were used as negative control. In order to allow a multiplexed screening setup, non-transfected cells were labeled using CFSE and mixed with non-labeled PD-1-transfected cells at a ratio of 1 to 1, and a density of 1E6 cells per ml, each. In 384-well plates, 40 µl of this cell mix was mixed with 10 µl of antibody-containing supernatant, and cell-bound antibody was revealed by addition of goat anti-human IgG (H+L) AF647 secondary antibody (Molecular Probes, Cat. No. A21445) in a non-wash setup. Samples were acquired using high throughput flow cytometry (iQue® Screener, Intellicyt) and data was analyzed using ForeCyt® software by plotting CFSE vs. human IgG binding (AF647). PD-1-specific primary hits were identified as antibody clones binding only to human PD-1-transfected cells (CSFE negative), but not to control cells (CFSE positive), and plate numbers and plate coordinates were collected for hit picking and subsequent sequence analysis.

Figure 3A:
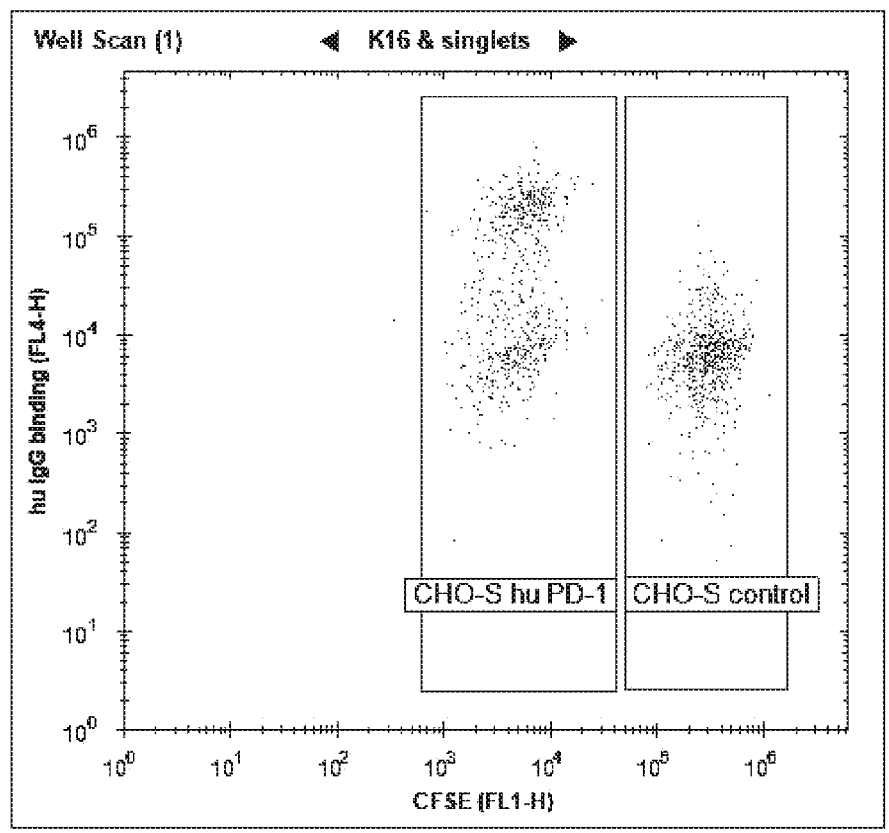
FIGS. 3A-3C show representative flow cytometry dot plots for (A) an antibody clone that specifically binds to human PD-1-transfected cells, (B) a clone that non-specifically binds to CHO-S cells, and (C) a clone that does not bind either of the cell populations used in the screening.
Figure 3B:
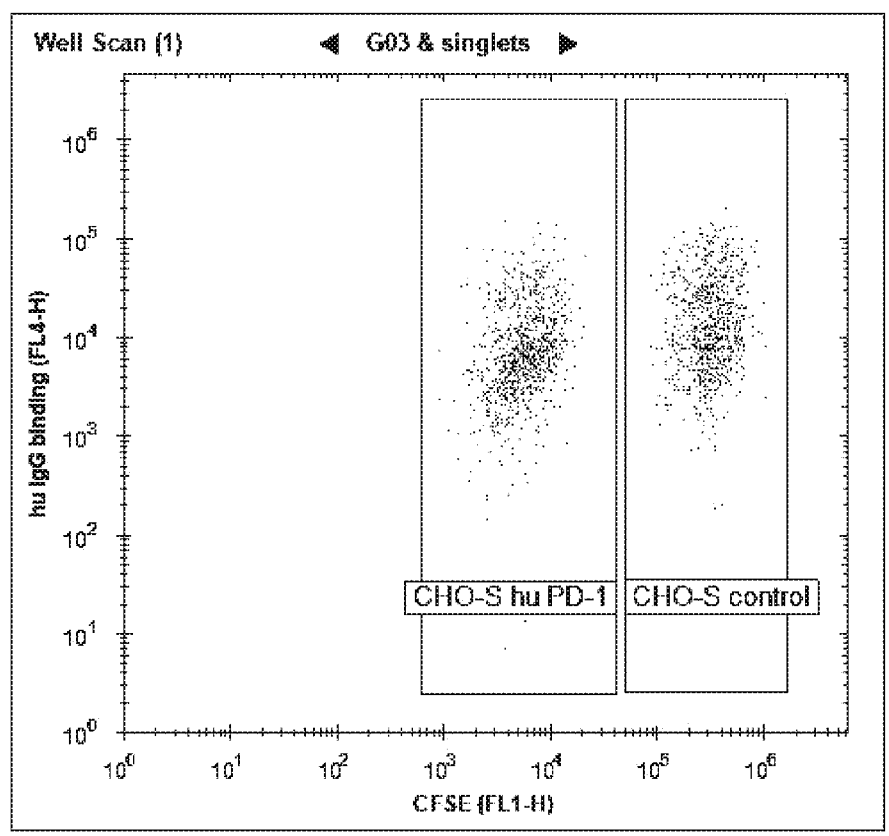
Figure 3C:
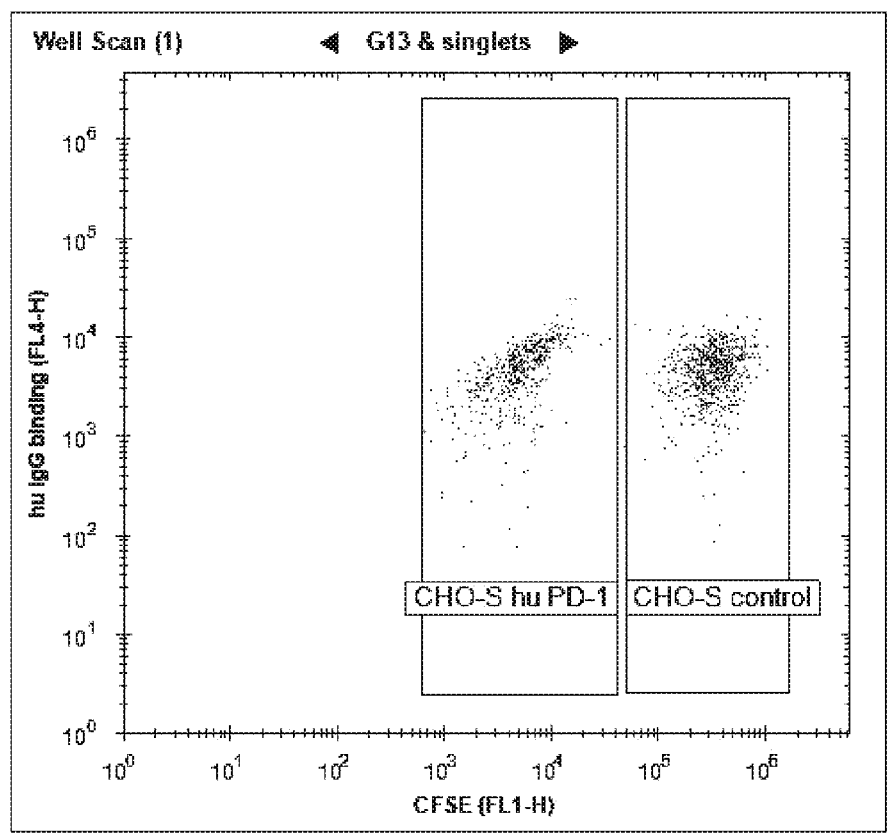

FIGS. 3A-3C show representative flow cytometry dot plots for (A) an antibody clone that specifically binds to human PD-1-transfected cells, (B) a clone that non-specifically binds to CHO-S cells, and (C) a clone that does not bind either of the cell populations used in the screening.

Example 4: Humanization of Anti-PD-1 Antibodies

Humanization of the framework regions of the chicken anti-PD-1 antibodies was performed in order to produce antibody molecules having minimal immunogenicity when administered to humans, while substantially retaining the specificity and affinity of the parental chicken antibodies.

Materials and Methods

Humanization of the chicken-derived antibodies was performed using the "CDR grafting" approach, a method originally described by Jones et al., Nature 321:522-525 (1986). First, the variable heavy ($V_H$) and variable light ($V_L$) domains of the antibodies were blasted against human IgG databases in order to find the closest human germline genes. This identified the human IGHV3-23*01 (M99660) and IGLV3-19*01 (X56178) genes as being closest to the chicken $V_H$ and $V_L$ genes, respectively. Similarly, the selected human amino acid sequences for J-gene region humanization were derived from IGHJ1*01 (J00256) and IGLJ6*01 (M18338) for $V_H$ and $V_L$, respectively. Furthermore, the antibody $V_H$ and $V_L$ genes were aligned against chicken immunoglobulin germline genes to identify somatic mutations in the framework regions that may play a role in antibody function and/or structure. Such residues may be included in the final humanized antibody genes as so-called "back mutation" residues. Finally, some amino acid positions, so-called "Vernier residues" (Foote and Winter, J Mol Biol. 224(2):487-99 (1992)), that are known to play an important role in antibody structure, stability and function, were considered to generate alternative humanized antibody variants including either human or chicken residues from the corresponding germlines.

The CDR sequences herein were determined according to the IMGT® definitions for CDR1 and CDR2. For heavy and light chain CDR3, the definitions herein include one extra amino acid residue upstream of the IMGT-CDR3 (Cys) and one extra amino acid residue downstream (Trp for $V_H$ CDR3, Phe for $V_L$ CDR3).

Assembly of the chicken CDR and human framework regions was performed by overlap extension PCR. The resulting humanized $V_H$ and $V_L$ PCR products were cloned into expression vectors (plasmids) harboring human heavy and light chain constant regions. To increase correct cleavage of the signal peptide upstream of the lambda chain, the second amino acid (Ser) of the lambda gene IGLV3.19 was replaced by another amino acid (Tyr) which is present in other human germlines, for example IGLV3.25. The heavy chain sequence contains the two "LALA" mutations (L234A/L235A) known to reduce effector function of the Fc region of IgG1 antibodies (Armour et al., Eur J Immunol. 29(8):2613-24 (1999); and Armour et al., Mol Immunol. 40(9):585-93 (2003)). The expression vector also contained the necessary regulatory sequences, allowing simultaneous expression of light and heavy chains that are assembled into full-length antibodies after transfection of mammalian cells.

Results

The final humanized antibody sequences are shown below in Table 4, and the CDR sequences are shown separately in Table 5. The CDR sequences are defined in the Tables in accordance with the IMGT® numbering scheme.

TABLE 4

$V_H$ and $V_L$ sequences of humanized anti-PD-1 antibodies*

| Humanized Antibody | $V_H$ Amino Acid Sequence | $V_L$ Amino Acid Sequence |
|---|---|---|
| [12819.15384] | EVQLLESGGGLVQPGGSLRLSCAASG FTFTRYDMVWVRQAPGKGLEWVAG IGDSNKMTRYAPAVKGRATISRDNSK NTLYLQMNSLRAEDTAVYYCAKGSCI ACWDEAGRIDAWGQGTLVTVSS (SEQ ID NO: 2) | SYELTQDPAVSVALGQTVRITCSGGGSYD GSSYYGWYQQKPGQAPVTVIYNNNNRP SDIPDRFSGSSSGNTASLTITGAQAEDEAD YYCGSYDRPETNSDYVGMFGSGTKVTVL (SEQ ID NO: 3) |

TABLE 4-continued

V_H and V_L sequences of humanized anti-PD-1 antibodies*

| Humanized Antibody | V_H Amino Acid Sequence | V_L Amino Acid Sequence |
|---|---|---|
| [12748.15381] | EVQLLESGGGLVQPGGSLRLSCAAS*GFTFSDYA*MNWVRQAPGKGLEWVA*GIGNDGSYT*NYGAAVKGRATISRDNSKNTLYLQMNSLRAEDTAVYYY*CASDIRSRNDCSYFLGGCSSGFIDVW*GQGTLVTVSS<br>(SEQ ID NO: 4) | SYELTQDPAVSVALGQTVRITCSGG*SSYS*YGWFQQKPGQAPVTVIY*ESN*NRPSDIPDRFSGSSSGNTASLTITGAQAEDEADYY*CGNADSSSGIF*GSGTKVTVL<br>(SEQ ID NO: 5) |
| [12865.15377] | EVQLLESGGGLVQPGGSLRLSCAAS*GFDFSDHG*MQWVRQAPGKGLEYVG*VIDTTGRYT*YYAPAVKGRATISRDNSKNTLYLQMNSLRAEDTAVYY*CAKTTCVGGYLCNTVGSIDAW*GQGTLVTVSS<br>(SEQ ID NO: 6) | SYELTQDPAVSVALGQTVRITCSGG*GSSSYY*GWYQQKPGQAPVTVIY*DDT*NRPSGIPDRFSGSSSGNTASLTITGAQAEDEADYY*CGGYEGSSHAGIF*GSGTKVTVL<br>(SEQ ID NO: 7) |
| [12892.15378] | EVQLLESGGGLVQPGGSLRLSCAAS*GFDFSSYT*MQWVRQAPGKGLEWVG*VISSTGGST*GYGPAVKGRATISRDNSKNTLYLQMNSLRAEDTAVYY*CVKSISGDAWSVDGLDAW*GQGTLVTVSS<br>(SEQ ID NO: 8) | SYELTQDPAVSVALGQTVRITCSGG*GSAY*GWYQQKPGQAPVTVIY*YNN*QRPSGIPDRFSGSSSGNTASLTITGAQAEDEADYY*CGSYDSSAVGIF*GSGTKVTVL<br>(SEQ ID NO: 9) |
| [12796.15376] | EVQLLESGGGLVQPGGSLRLSCAAS*GFDFSSYT*MQWVRQAPGKGLEWVG*VISSTGGST*GYGPAVKGRATISRDNSKNTLYLQMNSLRAEDTAVYY*CVKSVSGDAWSVDGLDAW*GQGTLVTVSS<br>(SEQ ID NO: 10) | SYELTQDPAVSVALGQTVRITCSGG*GSAY*GWYQQKPGQAPVTVIY*YNN*QRPSDIPDRFSGSSSGNTASLTITGAQAEDEADYY*CGSYDSSAVGIF*GSGTKVTVL<br>(SEQ ID NO: 11) |
| [12777.15382] | EVQLLESGGGLVQPGGSLRLSCAAS*GFDFSSYG*MQWVRQAPGKGLEWVG*VISGSGITTL*YAPAVKGRATISRDNSKNTVYLQMNSLRAEDTAVYY*CTRSPSITDGWTYGGAWIDAW*GQGTLVTVSS<br>(SEQ ID NO: 12) | SYELTQDPAVSVALGQTVRITCSGG*DGSY*GWFQQKPGQAPVTVIY*DND*NRPSDIPDRFSGSSSGNTASLTITGAQAEDEADYY*CGNADLSGGIF*GSGTKVTVL<br>(SEQ ID NO: 13) |
| [12760.15375] | EVQLLESGGGLVQPGGSLRLSCAAS*GFTFSTFN*MVWVRQAPGKGLEYVAEI*SSDGSFT*WYATAVKGRATISRDNSKNTVYLQMNSLRAEDTAVYY*CAKSDCSSSYYGYSCIGIIDAW*GQGTLVTVSS<br>(SEQ ID NO: 14) | SYELTQDPAVSVALGQTVRITCSGG*ISDDGSYY*YGWFQQKPGQAPVTVIY*IND*RRPSNIPDRFSGSSSGNTASLTITGAQAEDEADYY*CGSYDSSAGVGIF*GSGTKVTVL<br>(SEQ ID NO: 15) |
| [13112.15380] | EVQLLESGGGLVQPGGSLRLSCAAS*GFTFSSYN*MFWVRQAPGKGLEFVAEI*SGSNTGSRT*WYAPAVKGRATISRDNSKNTLYLQMNSLRAEDTAVYY*CAKSIYGGYCAGGYSCGVGLIDAW*GQGTLVTVSS<br>(SEQ ID NO: 16) | SYELTQDPAVSVALGQTVRITCSGG*SSDY*YGWFQQKPGQAPVTVIY*YNN*KRPSDIPDRFSGSSSGNTASLTITGAQAEDEADYY*CGNADSSVGVF*GSGTKVTVL<br>(SEQ ID NO: 17) |

*CDR regions are italicized, underlined, and in boldface.

TABLE 5

H- and L-CDR sequences of humanized anti-PD-1 antibodies

| Humanized antibody | HCDR1 | HCDR2 | HCDR3 | LCDR1 | LCDR2 | LCDR3 |
|---|---|---|---|---|---|---|
| [12819.15384] | GFTFTRYD | IGDSNKMT | CAKGSCIACWDEAGRIDAW | GSYDGSSY | NNN | CGSYDRPETNSDYVGMF |
| SEQ ID NO: | 18 | 19 | 20 | 21 | 22 | 23 |
| [12748.15381] | GFTFSDYA | IGNDGSYT | CASDIRSRNDCSYFLGGCSSGFIDVW | SSYS | ESN | CGNADSSSGIF |
| SEQ ID NO: | 24 | 25 | 26 | 27 | 28 | 29 |

TABLE 5-continued

H- and L-CDR sequences of humanized anti-PD-1 antibodies

| Humanized antibody | HCDR1 | HCDR2 | HCDR3 | LCDR1 | LCDR2 | LCDR3 |
|---|---|---|---|---|---|---|
| [12865.15377] | GFDFSDHG | IDTTGRYT | CAKTTCVGGYLCNTVGSIDAW | GSSSY | DDT | CGGYEGSSHAGIF |
| SEQ ID NO: | 30 | 31 | 32 | 33 | 34 | 35 |
| [12892.15378] | GFDFSSYT | ISSTGGST | CVKSISGDAWSVDGLDAW | GSA | YNN | CGSYDSSAVGIF |
| SEQ ID NO: | 36 | 37 | 38 | 39 | 40 | 41 |
| [12796.15376] | GFDFSSYT | ISSTGGST | CVKSVSGDAWSVDGLDAW | GSA | YNN | CGSYDSSAVGIF |
| SEQ ID NO: | 42 | 43 | 44 | 45 | 46 | 47 |
| [12777.15382] | GFDFSSYG | ISGSGITT | CTRSPSITDGWTYGGAWIDAW | DGS | DND | CGNADLSGGIF |
| SEQ ID NO: | 48 | 49 | 50 | 51 | 52 | 53 |
| [12760.15375] | GFTFSTFN | ISSDGSFT | CAKSDCSSSYYGYSCIGIIDAW | ISDDGSYY | IND | CGSYDSSAGVGIF |
| SEQ ID NO: | 54 | 55 | 56 | 57 | 58 | 59 |
| [13112.15380] | GFTFSSYN | ISGSNTGSRT | CAKSIYGGYCAGGYSCGVGLIDAW | SSDY | YNN | CGNADSSVGVF |
| SEQ ID NO: | 60 | 61 | 62 | 63 | 64 | 65 |

All of the humanized antibodies comprised the IgG1 "LALA" variant heavy chain constant region and light chain constant region amino acid sequences shown below.

Heavy chain constant region (SEQ ID NO: 67):
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Light chain constant region (SEQ ID NO: 68):
GQPKANPTVTLFPPSSEELQANKATLVCLISDFYPGAVTVAWKADGSPVK

AGVETTKPSKQSNNKYAASSYLSLTPEQWKSHRSYSCQVTHEGSTVEKTV

APTECS

Example 5: Screening of Anti-PD-1 Antibody Candidates

PD-1 is mainly expressed on the surface of activated T-lymphocytes, where it negatively regulates T-cell activity. In order to select the most functional anti-PD-1 antibody candidates, two different in vitro screening systems were established, a *Staphylococcus* Enterotoxin B (SEB) whole blood assay and a one-way mixed lymphocyte reaction assay.
Materials and Methods A repertoire of 69 unique humanized mAbs in the IgG1-LALA scaffold format, i.e., having the "LALA" mutations described in Example 4, and cloned and humanized as described above, were initially screened for functional activity in the SEB whole blood assay. SEB is a super-antigen that binds to MHC class II molecules and specific V6 regions of T cell receptors (TCR) and drives non-specific stimulation of T-cells. This results in polyclonal T cell activation/proliferation and release of cytokines including IL-2 and IFN-γ.

In order to investigate the relevance of the SEB assay for screening of anti-PD-1 activity, the expression level of PD-1 was investigated for different donors before and after SEB stimulation. PBMCs from six different donors were tested for PD-1 expression by flow cytometry at day 0 and day 3 after SEB stimulation. A relevant lymphocyte gate was set for further analysis.

Based on screening in the SEB whole blood assays, using blood from at least three different donors, the top 10 anti-PD-1 antibody lead candidates were identified. The anti-PD-1 antibody lead candidates were then further titrated to obtain dose-response curves for each individual antibody in comparison with the positive controls, reference analogues of the anti-PD-1 antibodies pembrolizumab (Merck) and nivolumab (Bristol-Myers Squibb); see Example 2.

The functionality of the top 10 selected anti-PD-1 antibodies was validated in an alternative in vitro assay, the one-way mixed lymphocyte reaction (MLR) assay. In this assay, dendritic cells (DCs) from one donor were co-cultured with CD4+ T-cells from another donor to obtain alloantigen specific stimulation, induced in 10-15% of all T-cells, leading to T-cell activation/proliferation and cytokine secretion.

Figure 4:
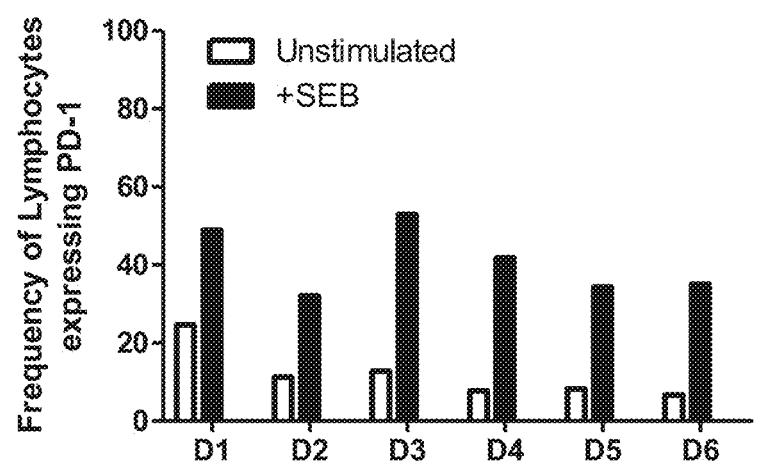
FIG. 4 shows the frequency of lymphocytes expressing PD-1 in six donors (D1-D6) before and after stimulation with SEB (*Staphylococcus* Enterotoxin B).

Due to a protein stability issue for one of the candidates (12748.15381), alternative germline sequences for this specific antibody were used. One of the resulting antibodies, 12748.16124, is referred to below. This variant has a different $V_L$ sequence, but the same $V_H$ sequence as 12748.15381 (Table 1, supra).
Results The data in FIG. 4 clearly shows that the frequency of lymphocytes expressing PD-1 is increased in all tested donors after SEB stimulation. These observations confirm the relevance of this assay for anti-PD-1 antibody screening.

Figure 5A:
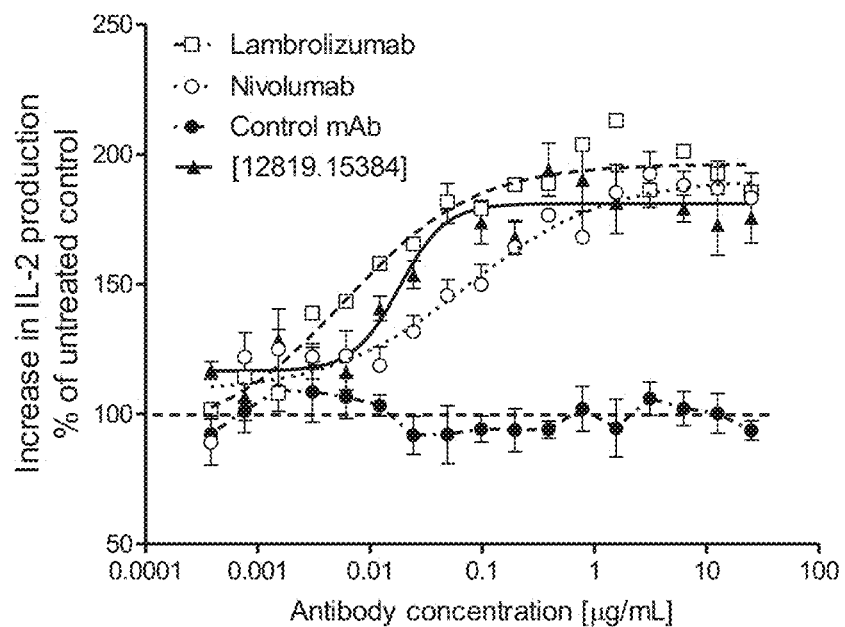
FIGS. 5A-I show titration of candidate anti-PD-1 antibodies in an SEB assay.
Figure 5B:
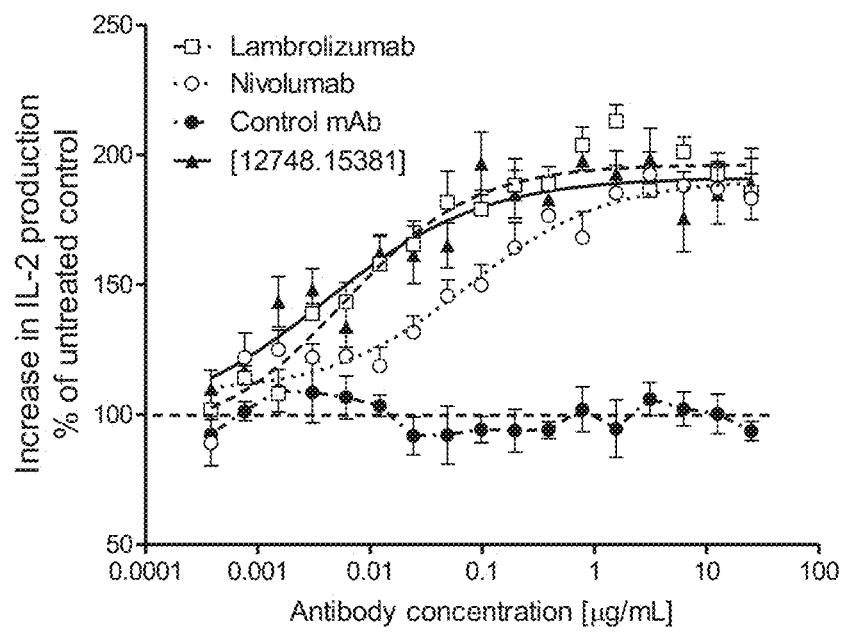
Figure 5C:
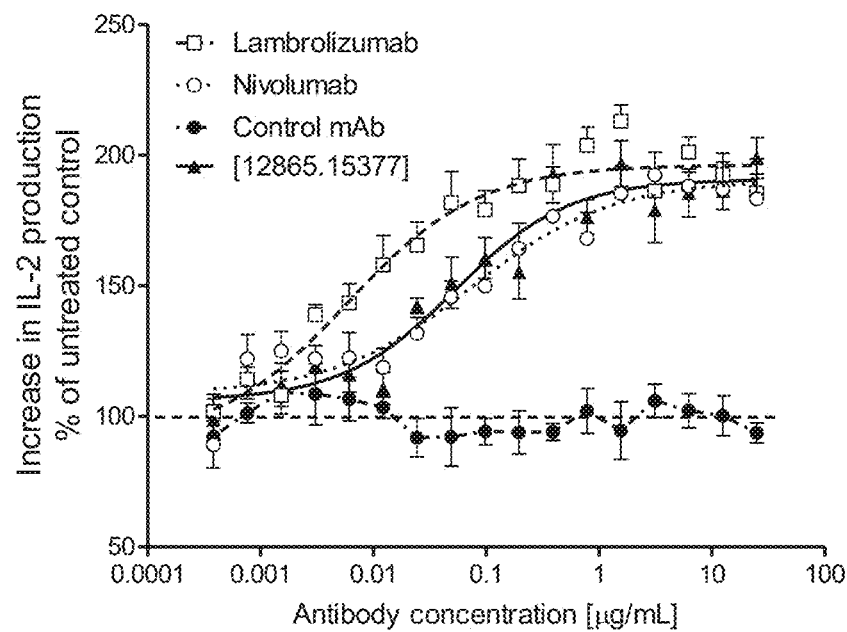
Figure 5D:
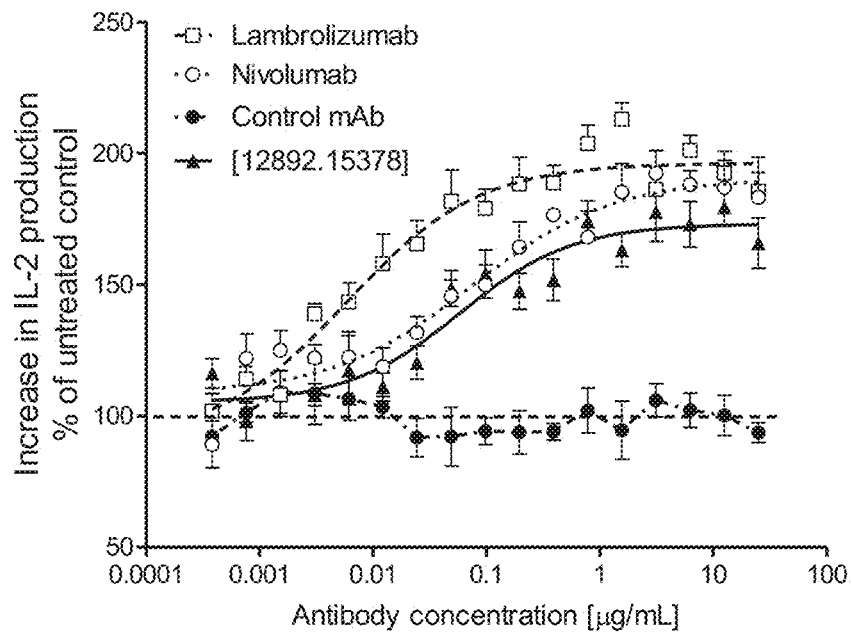
Figure 5E:
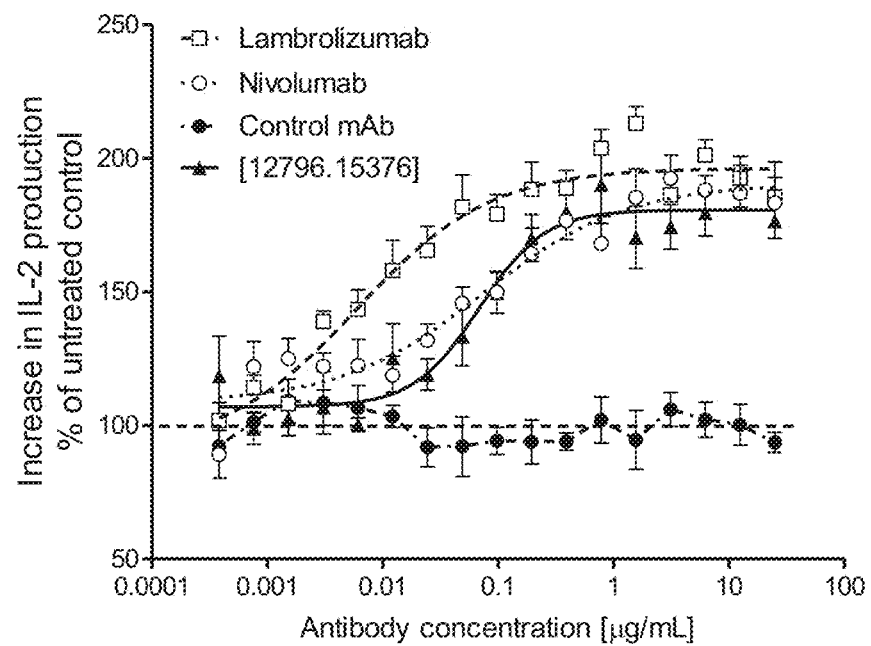
Figure 5F:
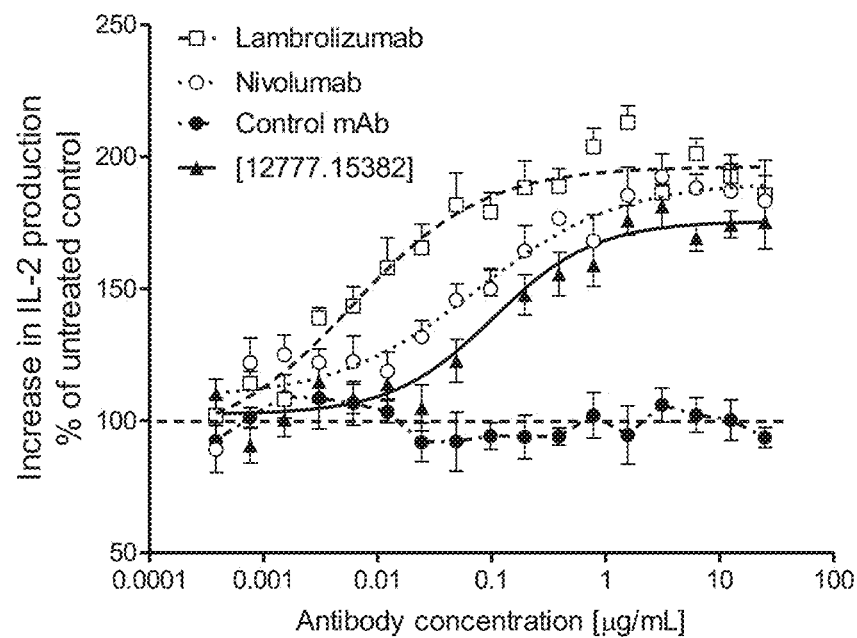
Figure 5G:
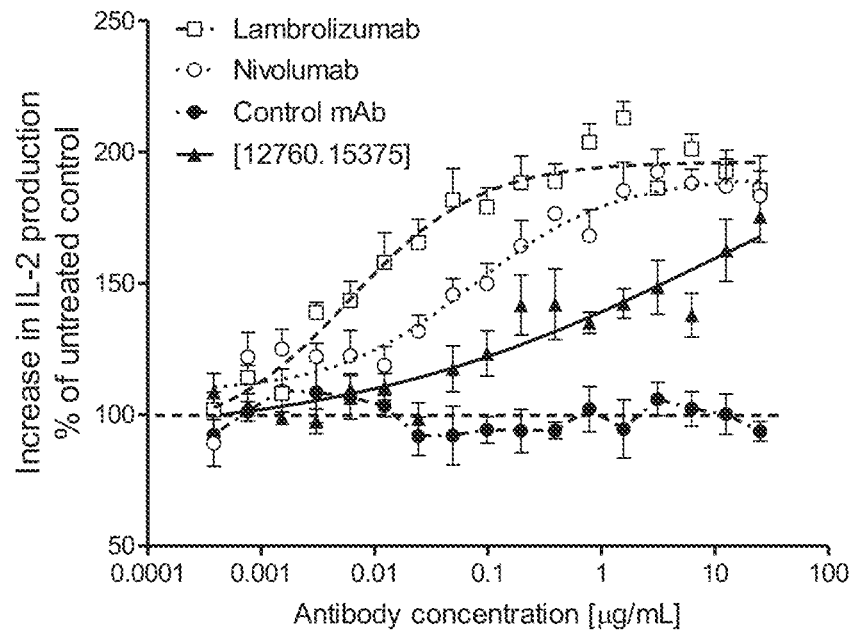
Figure 5H:
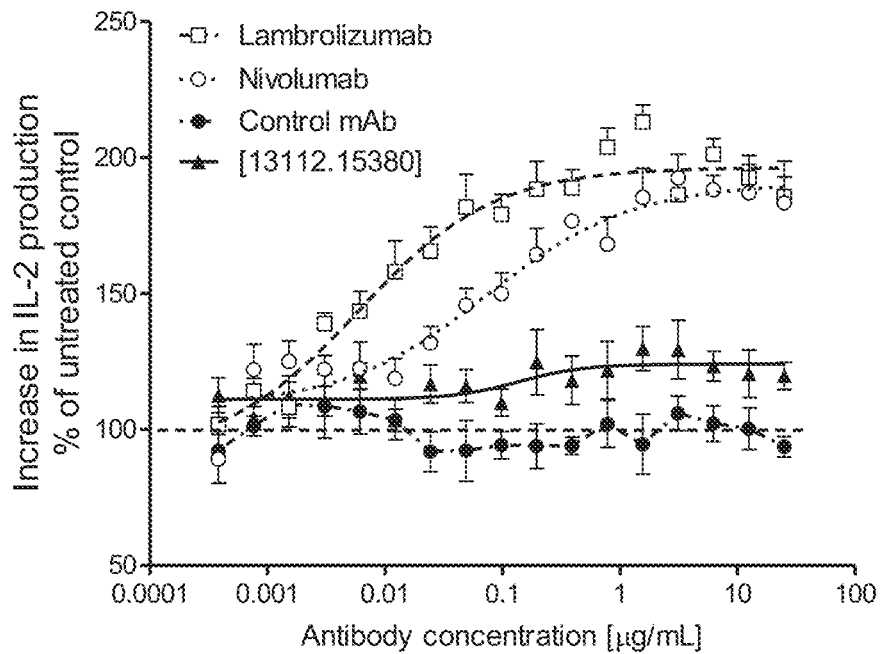

Titration of the most functional anti-PD-1 antibodies in the SEB assay, shown in FIGS. 5A-1, identified anti-PD-1 lead candidates with functionality similar or superior to the positive control antibody analogues pembrolizumab and nivolumab. In this assay, whole blood was stimulated with SEB for 48 h in the presence of the indicated antibodies, and IL-2 secretion after 48 hours was measured by ELISA. Each data point represents an average of six replicates, with the bars indicating the SEM.

Figure 5I:
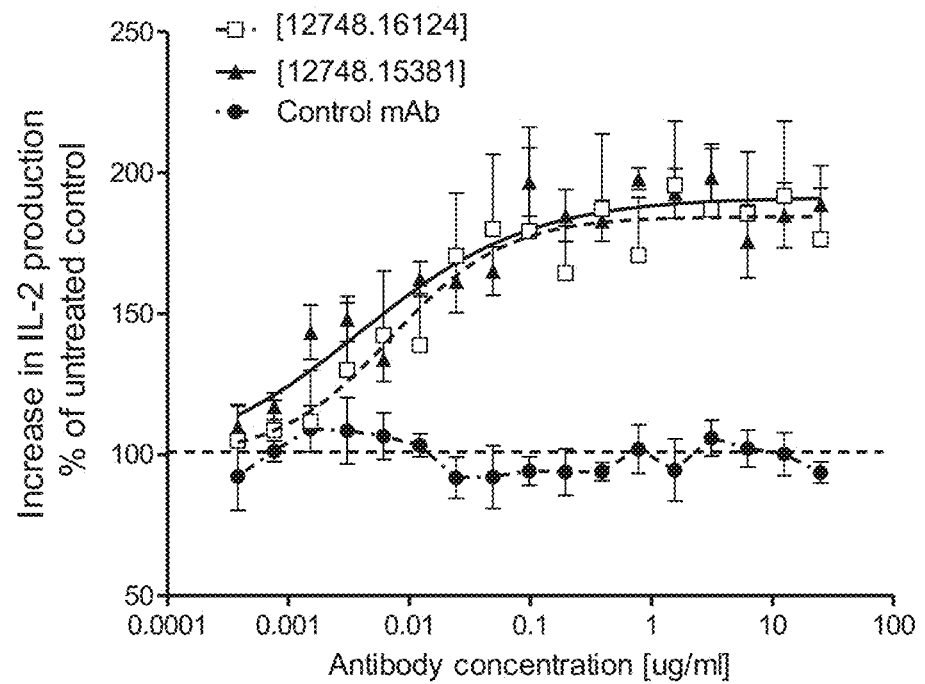
Figure 6A:
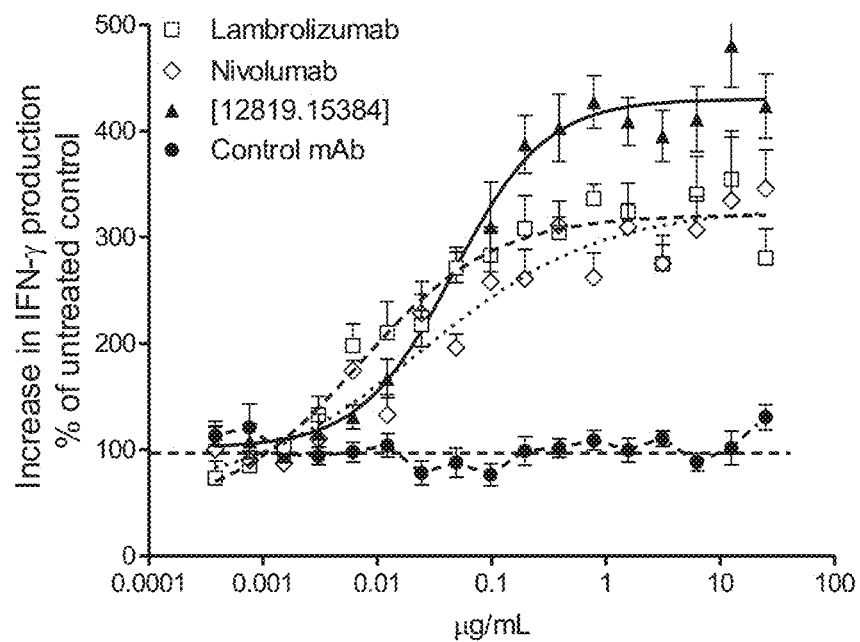
FIGS. 6A-H shows titration of candidate anti-PD-1 antibodies in a one-way MLR assay.
Figure 6B:
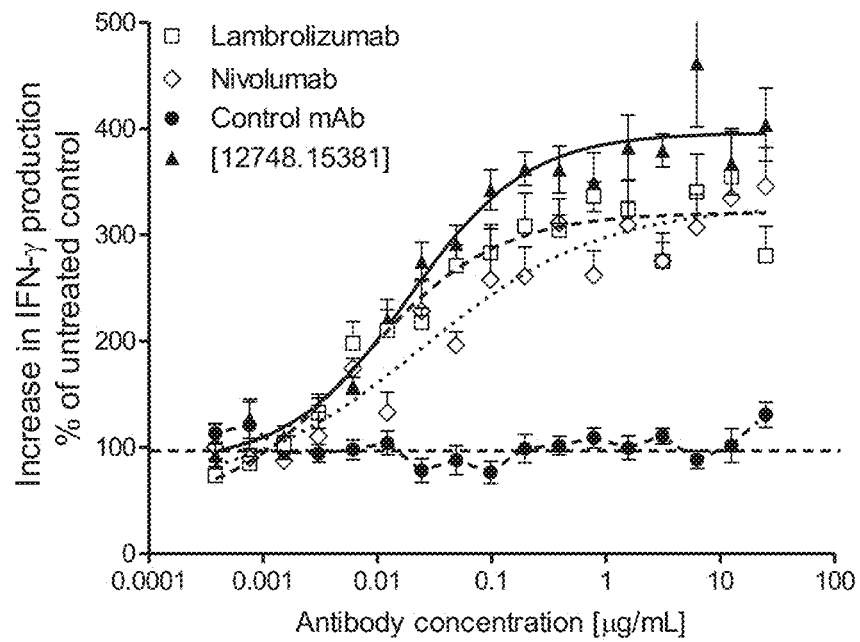
Figure 6C:
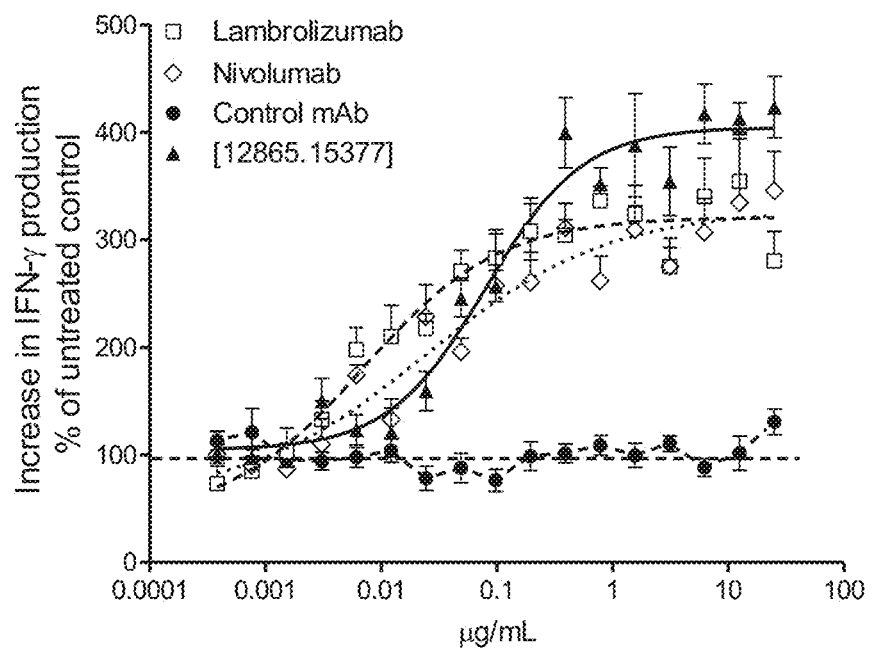
Figure 6D:
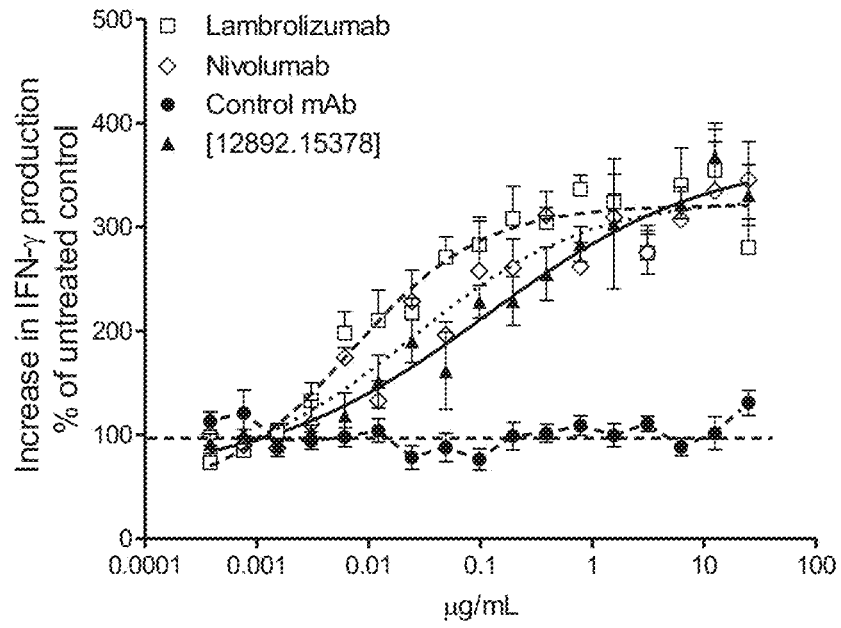
Figure 6E:
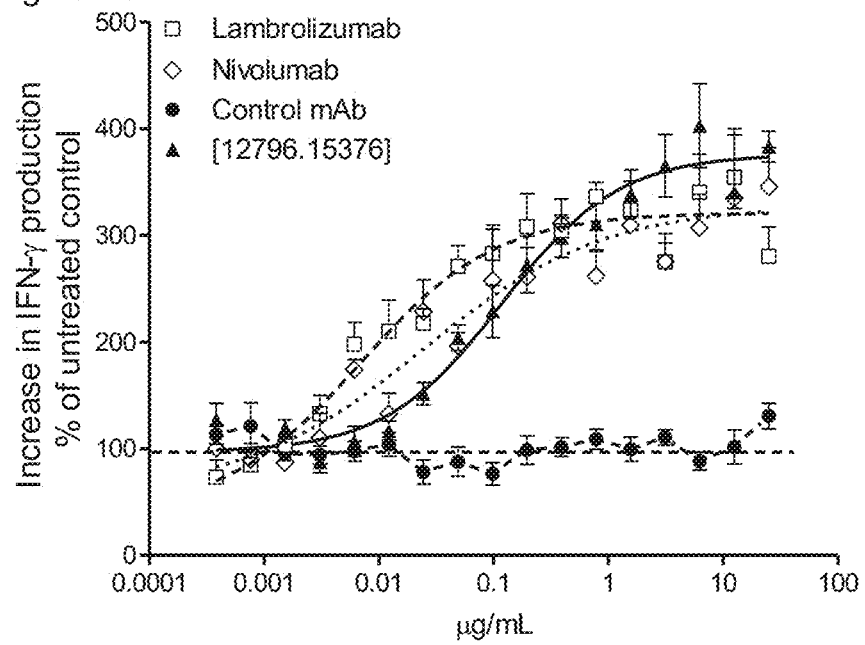
Figure 6F:
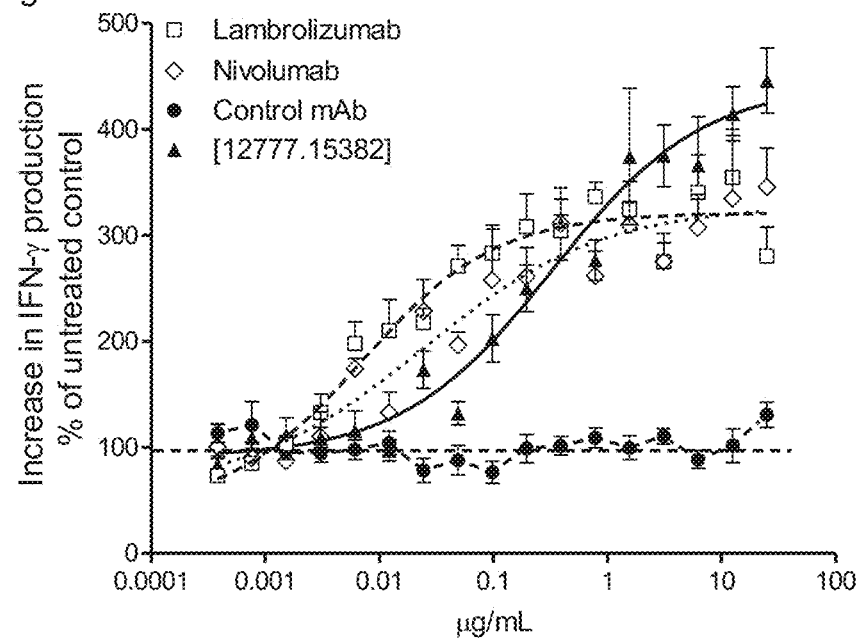
Figure 6G:
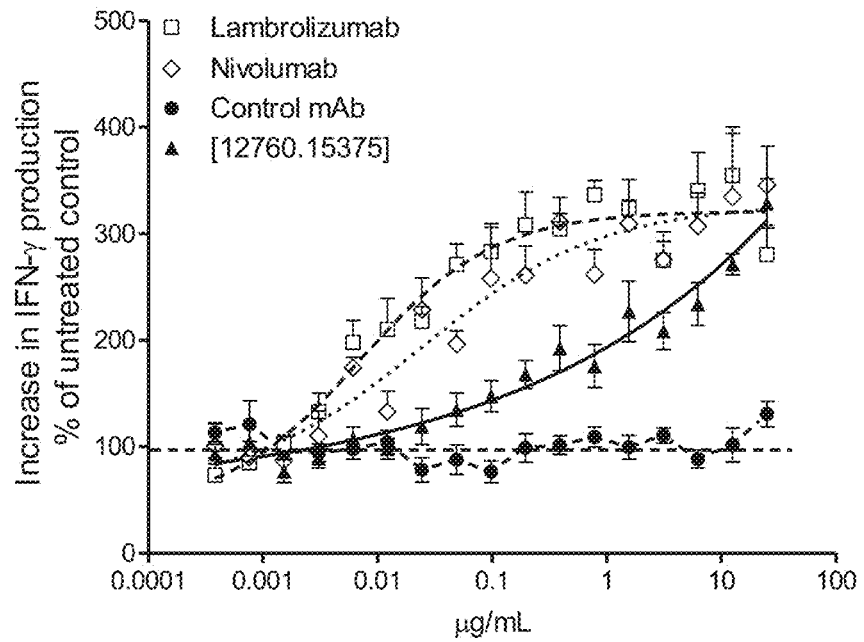
Figure 6H:
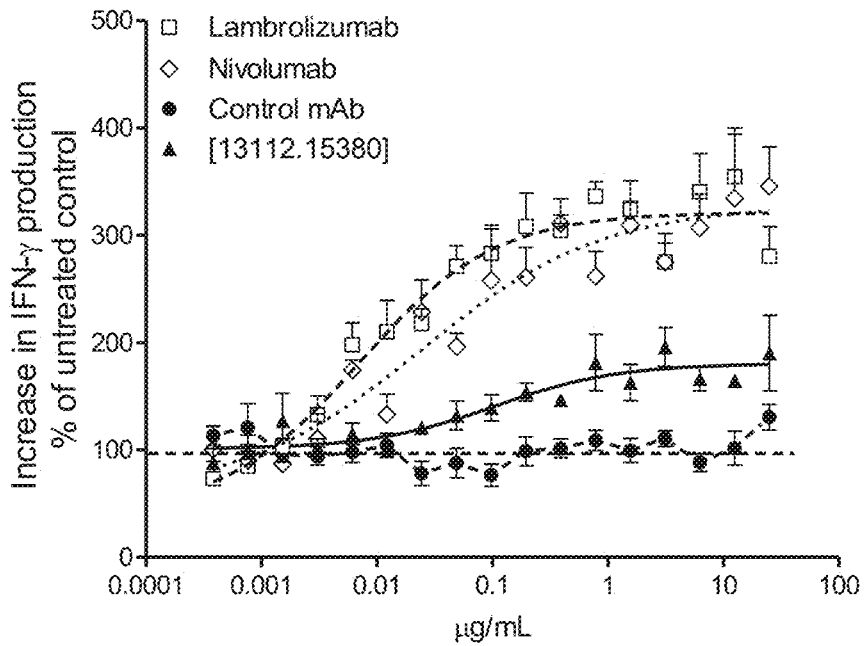

FIGS. 5A-H shows the results obtained with the humanized anti-PD-1 antibodies. Due to aggregation above 5% for one of the antibodies [12748.15381], an alternative framework for this antibody was tested. Data in FIG. 5I shows similar functionality of the original humanized antibody [12748.15381] and its germline (framework) variant [12748.16124].

The functionality of the anti-PD-1 antibodies was validated in a one-way MLR assay. In this assay, dendritic cells and CD4$^+$ T cells (ratio 1:10) from two different donors were co-cultured, and IFN-γ secretion was measured by MesoScale after 5 days. Each data point represents an average of six replicates, with the bars indicating the SEM. The data obtained from the one-way MLR assay and illustrated in FIGS. 6A-H show the same functionality and ranking of the anti-PD-1 antibodies as the data obtained from the SEB assay. This consistency in data between different assays provides further confirmation that the selected antibodies are functional.

The selected antibodies originate from two different main epitope bins, indicating that they bind to two different non-overlapping epitopes. All of the anti-PD-1 antibodies shown belong to Bin 1, except for 12760 and 13112 antibodies, which belong to Bin 2. It was found that the anti-PD-1 antibodies from Bin 1 show the highest functionality in these in vitro assays.

Example 6: Flow Cytometric Analysis of Anti-PD-1 Antibodies for PD-L1 Ligand Blocking Activity This example illustrates how the panel of anti-PD-1 antibodies was tested for PD-L1 ligand blocking activity by performing a flow cytometric competition assay using cell surface-expressed PD-1 and fluorochrome-labeled soluble PD-L1.

Materials and Methods

PD-L1 ligand blocking activity was investigated in a multiplex cellular assay, in which human and cynomolgus PD-1 were recombinantly expressed on CHO-S cells and binding of R-PE (R-phycoerythrin) labeled human PD-L1-Fc chimera protein was analyzed by flow cytometry. Commercially available recombinant PD-L1-Fc chimera protein (R&D Systems, USA) was conjugated to R-PE using the Lightning-Link® R-Phycoerythrin Conjugation Kit (Innova Biosciences, UK). CHO-S cells transiently transfected to express human PD-1 were mixed with CFSE-stained CHO-S cells transiently expressing cynomolgus PD-1. This cell mixture was then incubated with 50 µl anti-PD-1 antibody at 20 µg/ml on ice, followed by addition of 50 µl R-PE-labeled PD-L1-Fc at approx. 3.4 µg/ml (16.4 nM final concentration) and further incubation for an additional 20 min (final anti-PD-1 antibody concentration: 10 µg/ml). Bound antibody was detected using APC (allophycocyanin) conjugated anti-human IgG light chain antibody. Binding of PD-L1 and anti-PD-1 antibody was quantified by flow cytometry detecting R-PE and APC fluorescence, respectively.

Results

Figure 7A:
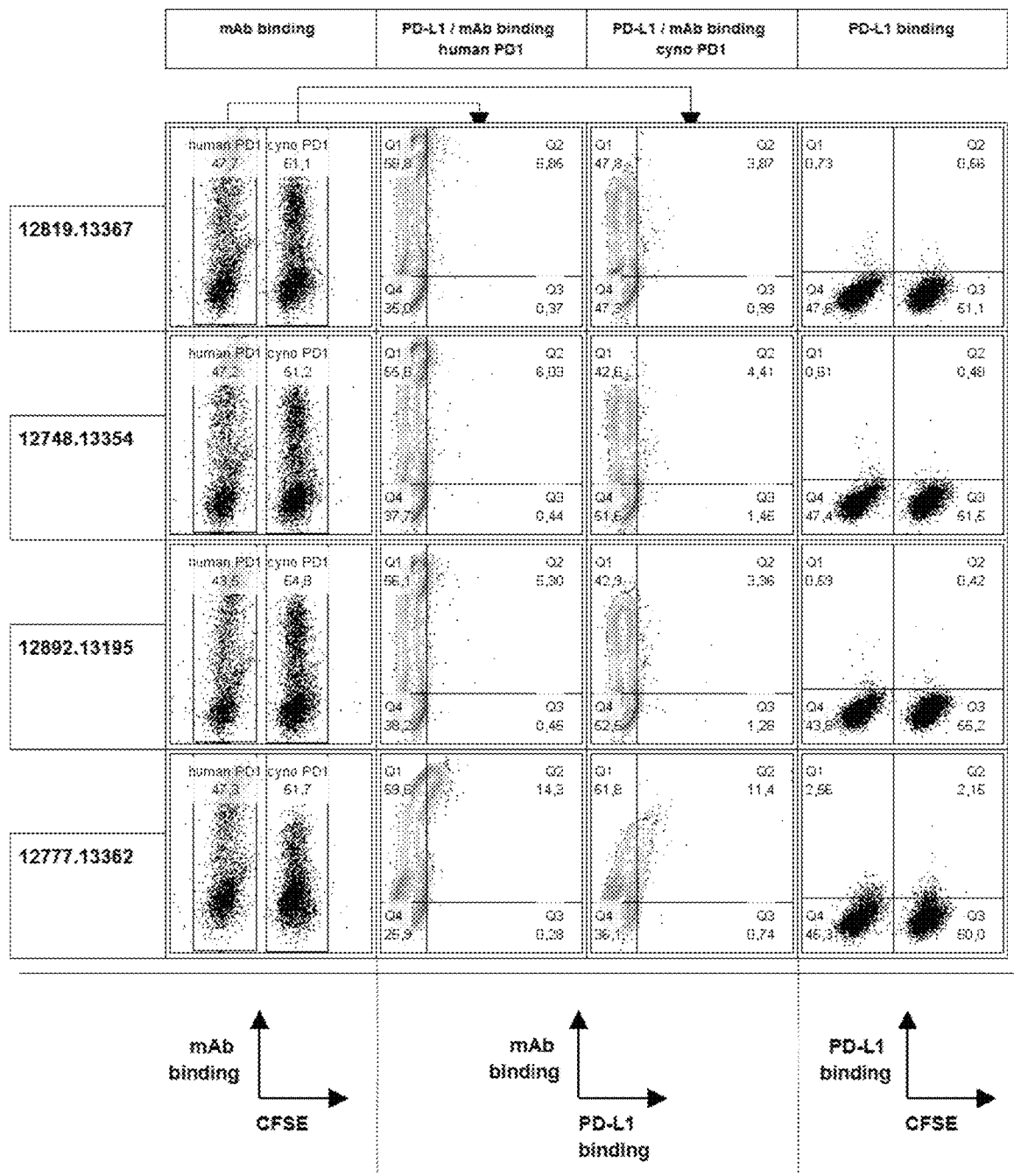
FIGS. 7A-B show PD-L1 binding to PD-1-expressing cells in the presence of anti-PD-1 antibodies.
Figure 7B:
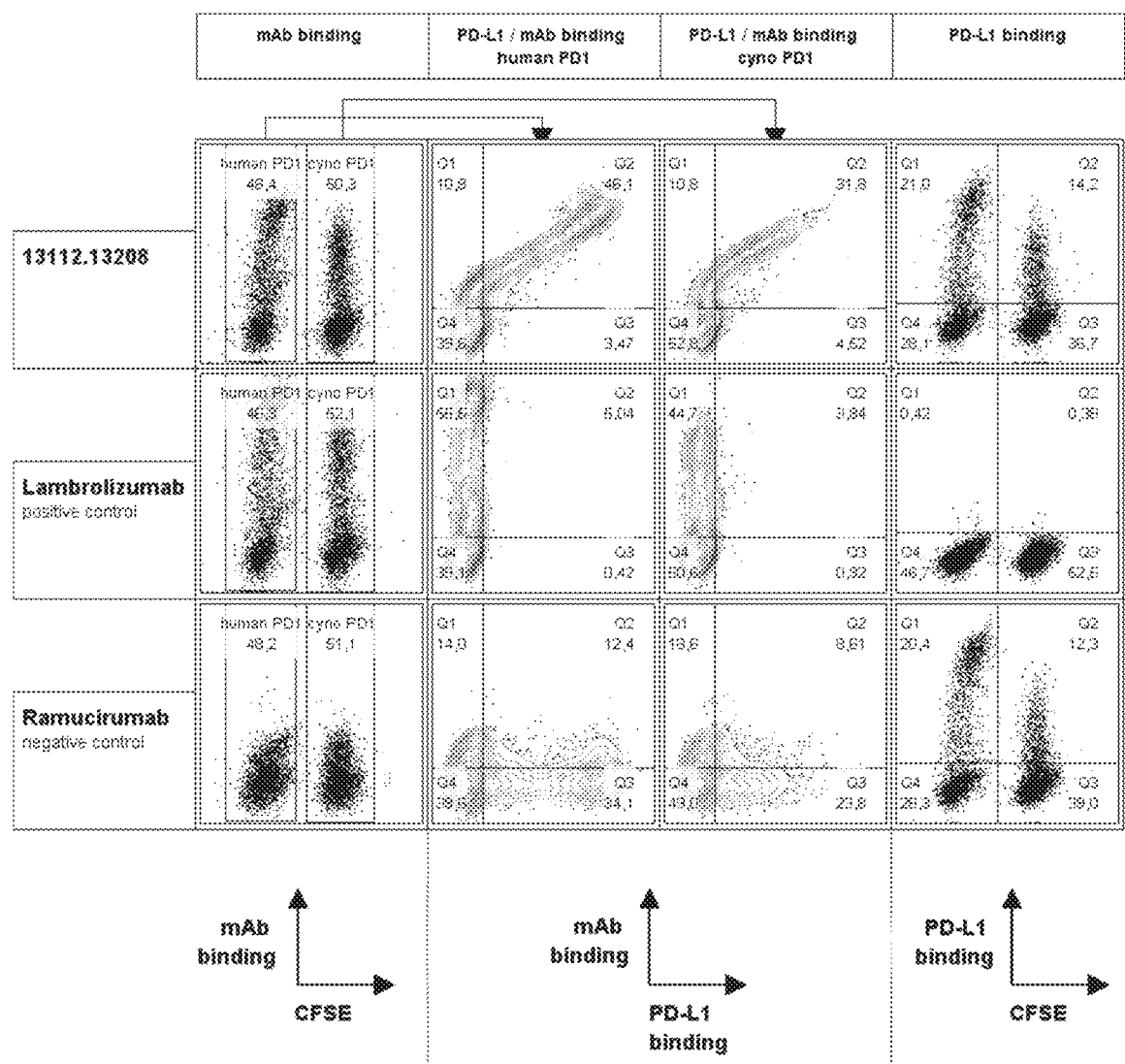

The results of the competition experiment are presented in FIGS. 7A-B and are summarized in Table 6 below. All anti-PD-1 antibodies were tested at a final antibody concentration of 10 µg/ml (see above). Three of the tested antibodies were able to inhibit PD-L1 binding by 83% or more, similar to the anti-PD-1 reference antibody lambrolizumab (Merck), which is the same as pembrolizumab and was included as a positive control. One antibody (12777.13362) only partially inhibited binding by 69%. One antibody (13112.13208) did not block PD-1 binding. Binding of PD-L1 to PD-1-expressing cells in the presence of the negative control anti-VEGFR2 antibody ramucirumab (Genentech) was set to 0%.

TABLE 6

| PD-L1 binding inhibition in the presence of anti-PD-1 antibodies | |
|---|---|
| Antibody | % PD-L1 binding inhibition |
| 12819.13367 | 87% |
| 12748.13354 | 86% |
| 12892.13195 | 88% |
| 12777.13362 | 69% |
| 13112.13208 | 5% |
| Lambrolizumab (pos. control) | 88% |
| Ramucirumab (neg. control) | set to 0% |

The humanized variants shown in Table 6 have the same amino acid sequences as those in Table 1 sharing the first 5 digits in their names, except that the variants in Table 1 have amino acid residues "SY" at the N-terminus of the light chain. In some embodiments, the SY dipeptide improves signal peptide processing during expression of the antibody light chain. The variants in Tables 1 and 6 are expected to have identical functional properties.

Example 7: Measurement of PD-1 Antibody Affinities Against Human and Cynomolgus PD-1 ECD Antigen This example demonstrates that the majority of anti-PD-1 antibodies show high picomolar (pM) affinity and good cross reactivity against both human and cynomolgus PD-1 extracellular domains (ECDs).

Materials and Methods

Kinetic binding analysis of the purified anti-PD-1 antibody repertoire was performed on an XPR-36 surface plasmon resonance (SPR) biosensor (Bio-Rad, USA). His-tagged human or cynomolgus PD-1 ECD antigens were purchased from Acro Biosystems, UK. Binding kinetics were measured under monovalent antigen conditions by immobilizing anti-PD-1 antibodies and keeping the monovalent PD-1 antigen in solution as described previously (Canziani et al., Anal Biochem 325(2):301-307 (2004)). The lowest possible anti-PD-1 antibody density was applied to prevent non-specific binding and mass transport limitation. For measuring antibody kinetics, anti-PD-1 antibodies were adjusted to a concentration of 1.0 µg/ml and captured on anti-human IgG Fc surfaces generated by immobilizing approximately 1000 RU of a monoclonal anti-human Fc antibody (Biacore, Denmark). Anti-PD-1 antibodies were tested for binding to human or cynomolgus PD-1 ECD in a 3-fold concentration range from 25 nM to 0.31 nM followed by regeneration of the surfaces with 3 M MgCl2 regeneration buffer (Biacore, Denmark). A high flow rate of 20 µl/min, an association time of 3.33 min and a dissociation time between 1.5 hours and 2.75 hours was employed. The recorded binding responses were fitted to a simple Langmuir 1:1 binding model for calculation of the on-rate ($k_{on}$ or ka), off-rate ($k_{off}$ or kd) and affinity (K D) constants using double referencing.

Results

The binding kinetics are tabulated in Table 7 below, which illustrates that the panel of anti-PD-1 antibodies binds PD-1 with very high affinities in the pM range. All antibodies recognized human PD-1 with higher affinity than the nivolumab and pembrolizumab analogues. The highest affinity antibody [12819.15384] binds human PD-1 with a $K_D$ of 20 pM.

China) was diluted in HBS-EP running buffer and injected at 50 nM concentration and captured by the conjugated array of anti-PD-1 antibodies. Next, individual injections of each of the ten PD-1 antibodies diluted to 100 nM in HBS-EP running buffer were performed to establish antibody competition patterns. After each competition cycle, the sensor surface was regenerated with 10 mM Glycine HCl buffer, pH 2.0.

Results

Figure 8:
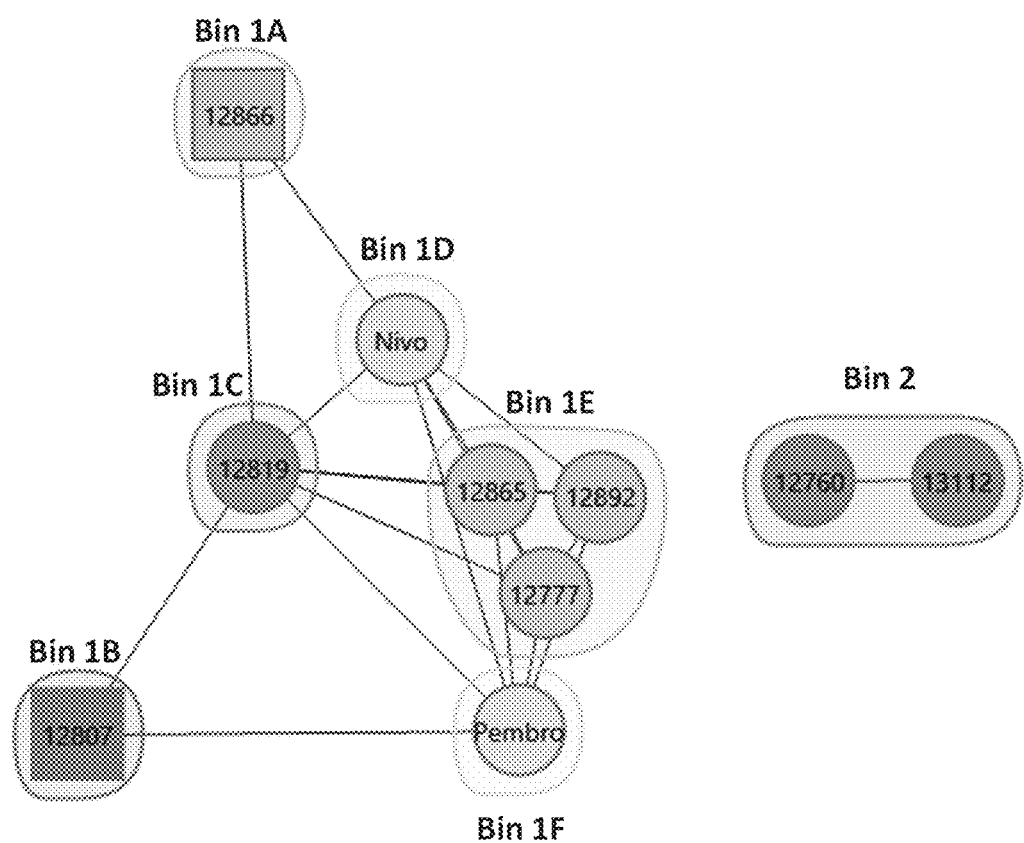
FIG. 8 shows an overview of the identified epitope groups (epitope bins) for tested anti-PD-1 antibodies 12866.13188, 12807.13177, 12819.17149, 12865.17150, 12892.13195, 12777.15382, 12760.13169, 13112.15380, and nivolumab and pembrolizumab analogues. Antibodies connected by black lines indicate cross blocking activity. Antibodies are grouped according to competition patterns with other anti-PD-1 antibodies. Nivo: nivolumab analogue; Pembro: pembrolizumab analogue.

The competition pattern of ten anti-PD-1 antibodies is presented in FIGS. 8. 12866 and 12807 were not found to have functional activity in cell-based assays, but were

TABLE 7

Binding kinetics of anti-PD-1 antibodies to human or cynomolgus PD-1 ECD as measured by Surface Plasmon Resonance (SPR)

| Antibody | PD-1 ECD | $k_{on}$ (M-1 s-1) | | $k_{on}$ Error | $k_{off}$ (s-1) | | $k_{off}$ Error | $K_D$ (pM) |
|---|---|---|---|---|---|---|---|---|
| [12819.15384] | Human | 1.1E+06 | ± | 1.7E+03 | 2.3E−05 | ± | 1.3E−07 | 20 |
| [12819.15384] | Cynomolgus | 9.7E+05 | ± | 1.6E+03 | 4.5E−06 | ± | 1.5E−07 | 5 |
| [12748.15381] | Human | 3.2E+06 | ± | 1.0E+04 | 1.7E−04 | ± | 7.1E−07 | 54 |
| [12748.15381] | Cynomolgus | 4.6E+06 | ± | 1.6E+04 | 4.7E−04 | ± | 9.1E−07 | 101 |
| [12748.16124] | Human | 3.4E+06 | ± | 8.2E+03 | 1.6E−04 | ± | 5.9E−07 | 47 |
| [12748.16124] | Cynomolgus | 4.8E+06 | ± | 1.8E+04 | 3.9E−04 | ± | 9.8E−07 | 81 |
| [12865.15377] | Human | 4.2E+05 | ± | 2.2E+03 | 2.3E−04 | ± | 5.5E−07 | 558 |
| [12865.15377] | Cynomolgus | 5.1E+05 | ± | 2.2E+03 | 3.8E−04 | ± | 7.3E−07 | 738 |
| [12892.15378] | Human | 4.6E+05 | ± | 2.3E+03 | 3.4E−04 | ± | 7.1E−07 | 737 |
| [12892.15378] | Cynomolgus | 2.9E+05 | ± | 1.0E+10 | 6.9E−04 | ± | 8.5E−01 | 2340 |
| [12796.15376] | Human | 7.1E+05 | ± | 3.9E+03 | 3.8E−04 | ± | 1.1E−06 | 542 |
| [12796.15376] | Cynomolgus | 3.2E+05 | ± | 3.5E+03 | 7.0E−04 | ± | 2.5E−06 | 2220 |
| [12777.15382] | Human | 2.4E+05 | ± | 1.7E+03 | 8.0E−05 | ± | 4.0E−06 | 337 |
| [12777.15382] | Cynomolgus | 2.5E+05 | ± | 7.3E+03 | 1.7E−04 | ± | 3.5E−06 | 681 |
| [12760.15375] | Human | 1.2E+06 | ±1 | 3.4E+03 | 1.4E−04 | ± | 6.5E−07 | 112 |
| [12760.15375] | Cynomolgus | 1.0E+06 | ± | 1.7E+04 | 7.2E−03 | ± | 5.8E−05 | 6940 |
| [13112.15380] | Human | 1.2E+06 | ± | 4.8E+03 | 6.9E−05 | ± | 7.4E−07 | 60 |
| [13112.15380] | Cynomolgus | 2.5E+06 | ± | 1.5E+04 | 1.1E−03 | ± | 3.9E−06 | 452 |
| nivolumab analogue | Human | 1.4E+06 | ± | 9.2E+03 | 1.1E−03 | ± | 4.1E−06 | 758 |
| nivolumab analogue | Cynomolgus | 1.4E+06 | ± | 8.5E+03 | 7.7E−04 | ± | 2.9E−06 | 542 |
| pembrolizumab analogue | Human | 2.4E+06 | ± | 2.7E+04 | 2.1E−03 | ± | 1.1E−05 | 852 |
| pembrolizumab analogue | Cynomolgus | 1.7E+06 | ± | 1.0E+04 | 3.3E−04 | ± | 9.5E−07 | 190 |

Example 8: Epitope Binning of Anti-PD-1 Antibodies

This example illustrates how the PD-1 antibodies were grouped into epitope bins based on paired competition patterns. Antibodies belonging to different epitope bins recognize different epitopes on PD-1 ECD.

Methods

Investigation of paired antibody competition was performed by Surface Plasmon Resonance (SPR) analysis using a Continuous Flow Microspotter (CFM) (Wasatch Microfluidics, US) combined with an IBIS MX96 SPR instrument (IBIS Technologies, The Netherlands). Surface Plasmon Resonance imaging analysis was performed on E2S SensEye® SPR sensors (Ssens BV, The Netherlands). A total of ten anti-PD-1 antibodies (human, IgG1) were diluted to 10 µg/ml in 50 mM sodium acetate buffer, pH 4.5. Antibodies were spotted onto an E2S SensEye® and conjugated for 15 minutes using a Continuous Flow Microspotter. After spotting, the SensEye® was positioned in the IBIS MX96 biosensor and deactivated with 1 M ethanolamine, pH 8.5 for 10 minutes. After sensor preparation, antibody competition analysis was performed using a classical sandwich assay. Monovalent PD-1 ECD antigen (Sino Biological, included because they recognize distinct epitopes. The tested functional anti-PD-1 antibodies were found to bind two non-overlapping epitope bins. Functional antibodies belonging to epitope Bin 1 all cross blocked each other and included nivolumab analogue ("Nivo"), pembrolizumab analogue ("Pembro"), 12819, 12892, 12865, and 12777. These antibodies were found to significantly block PD-L1 and PD-L2 binding. 12760 and 13112 were found to bind a separate epitope Bin 2 because they cross blocked each other, but did not block the binding of any of the antibodies from epitope Bin 1. Consequently 12760 and 13112 likely bind to a different site on PD-1 that does not overlap with the PD-L1 and PD-L2 ligand binding site.

The cross blocking functional antibodies 12819, 12865, 12892, 12777, nivolumab and pembrolizumab belonging to epitope Bin 1 could be further subdivided into four sub-bins based on competition with 12866 and 12807 (FIG. 8). 12819 (Bin 1C) was the only antibody that blocked the binding of both 12866 and 12807, while nivolumab (Bin 1D) only blocked 12866 and pembrolizumab (Bin 1F) only blocked 12807. The group of antibodies belonging to Bin 1E (12865, 12892 and 12777) was unique in that they did not block the binding of either 12866 or 12807.

Finally, 12866 (Bin 1A) and 12807 (Bin 1B) bound unique epitope bins. 12866 was blocked by 12819 and nivolumab but not by other anti-PD-1 antibodies, and 12807 was blocked by 12819 and pembrolizumab but not by other anti-PD-1 antibodies.

Example 9: Measurement of PD-1 Antibody Cross Reactivity to Mouse and Rat PD-1 ECD Antigen This example demonstrates that anti-PD-1 antibody 12819.15384 strongly cross-reacts with mouse PD-1 but does not bind to rat PD-1.
Materials and Methods His-tagged mouse and rat PD-1 ECD were purchased from Sino Biologicals. Kinetic binding analysis was conducted as described in Example 7.
Results The binding kinetics are tabulated in Table 8 below. The anti-PD-1 antibody 12819.15384 binds mouse PD-1 with a $K_D$ of 809 pM but does not recognized rat PD-1. The affinity to human PD-1 ECD was similar to that measured in Example 7. Antibody 12865.17150 did not bind mouse or rat PD-1. Neither of nivolumab and pembrolizumab reference analogues cross-reacted with mouse or rat PD-1 (data not shown).

TABLE 8

Binding kinetics of PD-1 antibody 12819.15384 to human, mouse or rat PD-1 ECD as measured by Surface Plasmon Resonance (SPR)

| Antibody | PD-1 ECD | $k_{on}$ (M-1 s-1) | ± | $k_{on}$ Error | $k_{off}$ (s-1) | ± | $k_{off}$ Error | $K_D$ (pM) |
|---|---|---|---|---|---|---|---|---|
| [12819.15384] | human | 3.26E+05 | ± | 3E+02 | 8.85E−06 | ± | 5E−08 | 28 |
| [12819.15384] | mouse | 3.71E+04 | ± | 5E+01 | 3.04E−05 | ± | 7E−09 | 809 |
| [12819.15384] | rat | N.B.* | ± | | N.B. | ± | | N.B. |

*N.B: Not binding.

Example 10: Analysis of PD-L1 and PD-L2 Ligand Blocking Activity of PD-1 mAbs

This example illustrates how the panel of anti-PD-1 antibodies was analyzed for PD-L1 or PD-L2 ligand blocking activity by performing a competition assay using Bio-Layer Interferometry analysis.
Materials and Methods Investigation of PD-L1 or PD-L2 ligand blocking activity was performed by Bio-Layer lnterferometry (BLI) analysis using an Octet QK384 instrument (Fortebio, USA). Commercially available human PD-1 Fc fusion protein (Sino Biological) at 5 μg/ml concentration was captured on anti-human Fc sensor chips (Fortebio, USA) and residual anti-Fc sites blocked with Herceptin® negative control antibody. Next the antigen coated surface was saturated with anti-PD-1 antibody at a concentration of 10 μg/ml. After PD-1 saturation with anti-PD-1 antibody, ligand blocking activity of PD-L1 or PD-L2 was assessed by incubation with human PD-L1 or PD-L2 Fc fusion proteins (Sino Biological) tested at 5 μg/ml.
Results The result of the competition analysis is presented in Table 9 below. All antibodies fully blocked both PD-L1 or PD-L2 ligand binding except for antibody 12760.13169, which showed no significant blocking of PD-L1 or PD-L2 (26% and 36%, respectively), and 13112.13208, which showed no blocking of PD-L1 and weak blocking of PD-L2 (27% and 53%, respectively). The results were in good agreement with the epitope binning analysis (Example 8) and epitope mapping analysis (Example 11), which showed that all antibodies except 12760 and 13112 bind to overlapping epitopes that map to the PD-L1 and PD-L2 binding site on PD-1, while 12760 and 13112 antibodies bind to a separate PD-1 site and do not significantly cross compete with PD-L1 and PD-L2.

TABLE 9

PD-L1 and PD-L2 inhibition after anti-PD-1 antibody saturation

| mAb | Ligand | % Blocking |
|---|---|---|
| 12748.13354 | PD-L1-Fc | 97 |
| 12748.13354 | PD-L2-Fc | 96 |
| 12760.13169 | PD-L1-Fc | 44 |
| 12760.13169 | PD-L2-Fc | 26 |
| 12777.13362 | PD-L1-Fc | 93 |
| 12777.13362 | PD-L2-Fc | 90 |
| 12796.13173 | PD-L1-Fc | 99 |
| 12796.13173 | PD-L2-Fc | 92 |
| 12819.13367 | PD-L1-Fc | 94 |
| 12819.13367 | PD-L2-Fc | 94 |
| 12865.13185 | PD-L1-Fc | 98 |
| 12865.13185 | PD-L2-Fc | 94 |
| 12892.13195 | PD-L1-Fc | 88 |

TABLE 9-continued

PD-L1 and PD-L2 inhibition after anti-PD-1 antibody saturation

| mAb | Ligand | % Blocking |
|---|---|---|
| 12892.13195 | PD-L2-Fc | 77 |
| 13112.13208 | PD-L1-Fc | 53 |
| 13112.13208 | PD-L2-Fc | 27 |
| nivolumab analogue | PD-L1-Fc | 100 |
| nivolumab analogue | PD-L2-Fc | 98 |
| pembrolizumab analogue | PD-L1-Fc | 100 |
| pembrolizumab analogue | PD-L2-Fc | 99 |

No significant ligand blocking
50-70 Intermediate ligand blocking
70-90 Intermediate ligand blocking
90-100 Full ligand blocking Example 11: Epitope Mapping of Anti-PD-1 Antibodies by PD-1 Mutagenesis Antibody epitopes can generally be characterized as linear epitopes (also termed continuous epitopes) or conformational epitopes (also termed discontinuous epitopes). While linear epitopes are defined based on a single continuous amino acid sequence, conformational epitopes may consist of many smaller discontinuous linear sequences or single contact residues. A collection of contact residues that cluster at the intermolecular protein interface between the antibody and the antigen is also termed a hot spot or core epitope (Moreira et al., Proteins 68(4):803-12 (2007)). It is now widely acknowledged that most B-cell epitopes are discontinuous in nature (Sivalingam and Shepherd, *Mol Immunol.*

51(3-4):304-92012 (2012), Kringelum et al., *Mol Immunol.* 53(1-2):24-34 (2013)) with the average epitope spanning 15-22 amino acid residues of which 2-5 amino acids contribute with most of the binding energy (Sivalingam and Shepherd, supra).

By ranking binding affinity to 111 different PD-1 mutants, this example illustrates how the binding epitopes of 12819 and 12865 antibodies can be divided into linear epitopes and hotspots that are distinct from the epitopes recognized by nivolumab and pembrolizumab.

Methods

Figure 9:
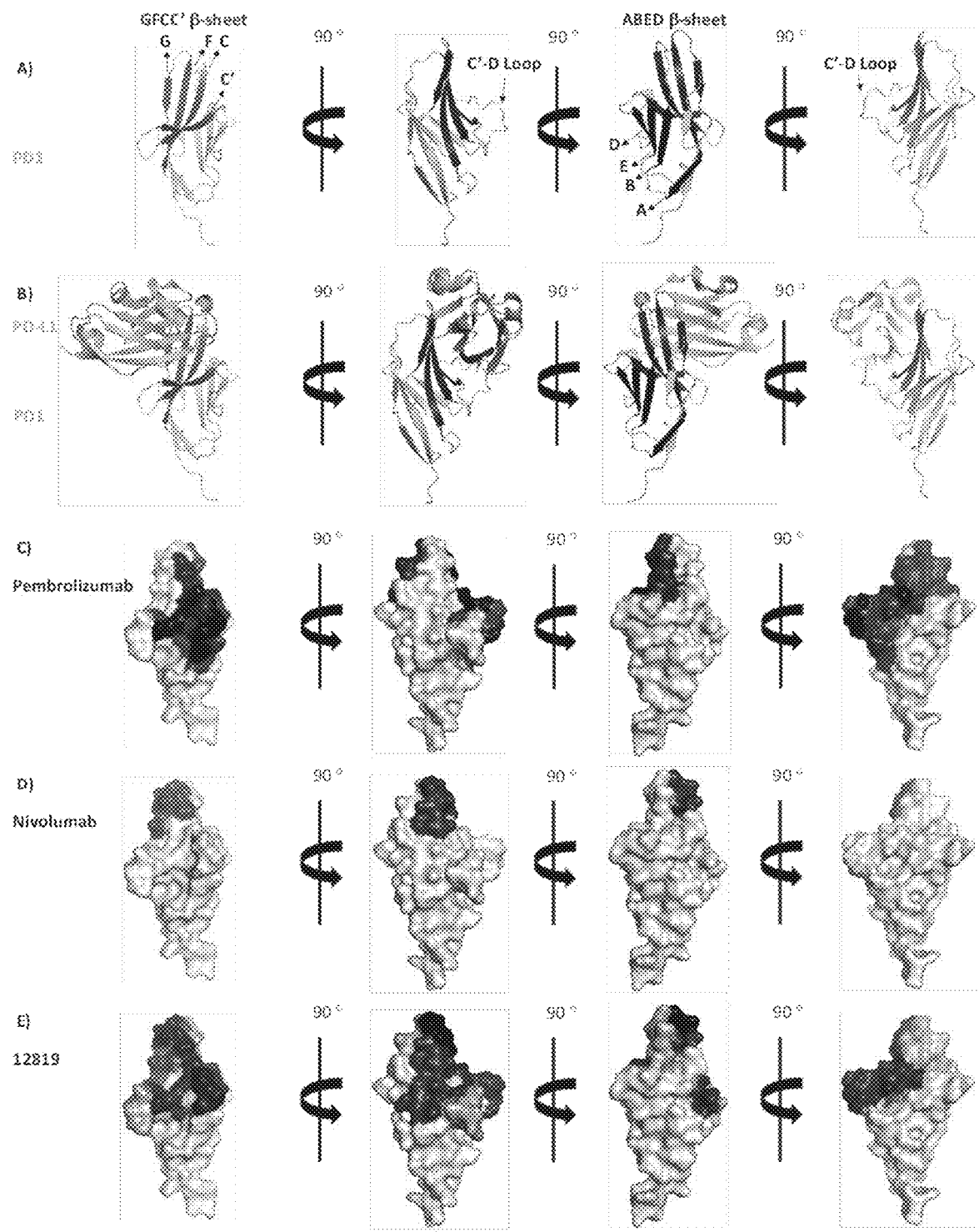
FIG. 9 (panels A-G) show the location of antibody epitopes on the structure of human PD-1 (PDB 4ZQK and 2M2D). A) Cartoon of human PD-1 extracellular domain (ECD) (residues 33-150). The location of the GFCC' and the ABED β-sheet and the C'-D loop are illustrated. B) Cartoon of the human PD-1:human PD-L1 complex at same viewing angles as in (A). C) Molecular model of the pembrolizumab epitope shown as a density map with darker areas representing regions mediating stronger binding. Black areas represent contact residues found by alanine scanning. D) Molecular model of the nivolumab epitope represented as in (C). E) Molecular model of the 12819 antibody epitope represented as in (C). F) Molecular model of the 12865 antibody epitope represented as in (C). G) Molecular model of the non-ligand blocking 13112 antibody epitope represented as in (C).
Figure 9:
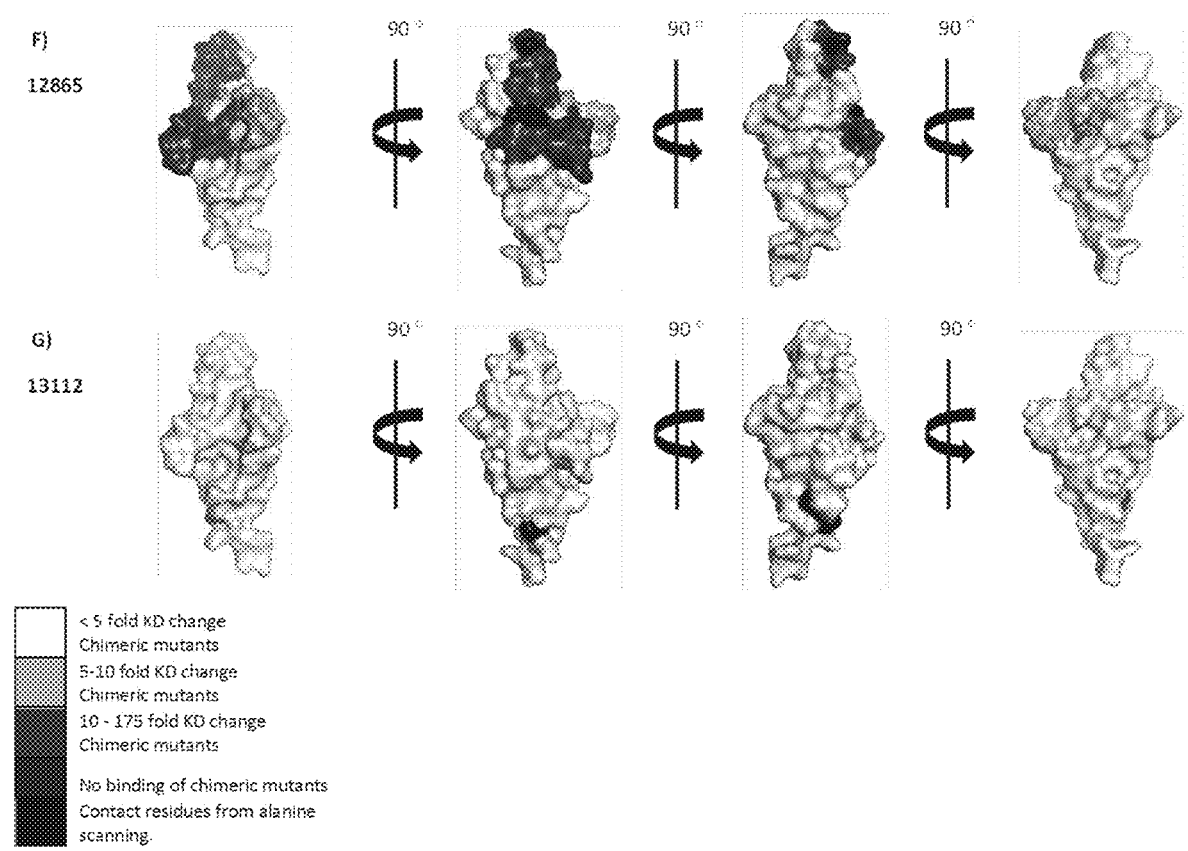

The human PD-1 receptor consists of an extracellular domain of 268 amino acids (residues 21-288). The extracellular domain spans amino acids 21-170 followed by a transmembrane domain (residues 171-191) and a cytoplasmic domain (residues 192-288). PD-1 belongs to the immunoglobulin superfamily and is composed of a two layer β-sandwich made from interactions of 8 anti-parallel β-strands arranged into two β-sheets with GFCC' β-strands on one side and ABED β-strands on the opposing side. The two β-sheets are stabilized by a disulphide bond between residues C54-C123. A crystal structure is available for the human PD-1:human PD-L1 complex (PDB 4ZQK), but the C'D loop between the C' and D β-strands was unstructured and is missing as well as some of the C-terminal sequence after residue 146 (PDB 4ZQK, Zak et al., *Structure* 23(12): 2341-2348 (2015)). Recently a crystal structure of the human PD-1:pembrolizumab complex was published (PDB 5JXE, Na et al., *Cell Res.* 2016 [Epub ahead of print], PMID: 27325296). In this structure the C'D loop is much more ordered and the contact residues important for pembrolizumab binding were shown to cluster to a core epitope on this loop. No crystal structure of the human PD-1:human PD-L2 complex is available. A NMR structure of human PD-1 in solution shows high structural similarity to the crystal structure PDB 4ZQK (PDB 2M2D, Cheng et al., *J Biol Chem* 288(17):11771-85 (2013)). Human PD-1 binds human PD-L1 or PD-L2 ligands in a 1:1 stoichiometry and binding mainly occurs at overlapping binding sites mediated by the GFCC' β-sheet (Cheng et al., *J Biol Chem* 288(17): 11771-11785 (2013)) (FIG. 9, panels A and B). Human PD-L1 binds human PD-1 through contact residues V64, N66, Y68 situated in the C β-strand and G124, I126, L128, A132, I134 and E136 located in the F and G β-strands (Zak et. al., *Structure* 23(12):2341-8 (2015)). Human PD-L1 and PD-L2 bind human PD-1 with Kos of 8 μM and 2 μM, respectively (Cheng et. al., supra).

The protein sequence of human PD-1 was downloaded from Uniprot (Accession No. Q15116; the amino acid sequence is represented in SEQ ID NO: 1). The full-length *Macaca fascicularis* protein sequence was downloaded from Uniprot (Accession No. B0LAJ3_MACFA (SEQ ID NO: 89)). The full-length protein sequences of *Gallus galus*, *Mus musculus* and *Rattus norvegicus* PD-1 were downloaded from NCBI (XP_422723. (SEQ ID NO: 90), NP_032824.1 (SEQ ID NO: 91) and XP_006245633.1 (SEQ ID NO: 92), respectively). The sequence identities of the different PD-1 extracellular amino acid sequences as compared to human PD-1 are shown in Table 10 below.

TABLE 10

PD-1 ECD sequence comparison among species

| | Amino Acid Differences | % Sequence Identity |
|---|---|---|
| *Macaca fascicularis* PD-1 ECD | 6 | 96.0 |
| *Rattus norvegicus* PD-1 ECD | 50 | 66.7 |

TABLE 10-continued

PD-1 ECD sequence comparison among species

| | Amino Acid Differences | % Sequence Identity |
|---|---|---|
| *Mus musculus* PD-1 ECD | 57 | 62.0 |
| *Gallus gallus* PD-1 ECD | 73 | 51.3 |

A molecular model of human PD-1 was built by combining structural information from the crystal structure of human PD-1:Human PD-L1 complex determined at 2.45 Å resolution (PDB 4ZQK) and a NMR structure of APO human PD-1 (PDB 2M2D). The structure PDB 4ZQK was used as the basis for the model with the missing C'D loop and c-terminal part of PD-1 provided from the NMR structure. Next, surface exposed amino acid residues were highlighted and 83 individual alanine substitutions were designed on surface exposed residues on human PD-1 ECD (alanine scanning) and 5 exposed residue positions that differed between human, mouse and rat PD-1 were back-mutated to rat PD-1 residues.

To map linear antibody epitopes in the context of the native human PD-1 structure, 23 chimeric proteins were generated where 10 amino acids in the human PD-1 ECD sequence were sequentially exchanged to chicken sequence in segments that overlapped by 5 amino acids. Sequence exchanges were performed in the extracellular domain of human PD-1 spanning amino acids 31-146, since the *Gallus gallus* protein sequence outside this segment did not align well with human PD-1 and was omitted.

The PD-1 cDNA coding for the extracellular domain of human PD-1 was synthesized and cloned into a vector containing CMV promoter and human $IgG_1$ Fc sequence (residues P101-K330) resulting in fusion of $IgG_1$ Fc C-terminally to the cloned PD-1 ECD. The mutated human PD-1 Fc fusion constructs were generated by standard PCR and engineering techniques and protein was expressed transiently in 2 ml culture using an ExpiCHO™ expression system. The human PD-1 Fc fusion constructs were harvested after 9 days and supernatants were tested for binding affinity to anti-PD-1 Fabs by Surface Plasmon Resonance (SPR). Culture supernatants containing PD-1 fusion proteins were immobilized onto an G-a-hu-IgG Fc SensEye® (Ssens BV, The Netherlands) for 15 minutes using a Continuous Flow Microspotter (CFM, Wasatch Microfluidics, Salt Lake City, US). After spotting, the SensEye® was positioned in an IBIS MX96 biosensor and captured proteins were fixed to the surface using FixIT kit (Ssens BV, The Netherlands). Kinetic analysis was performed by applying a so called kinetic titration series (Karlsson R. 2006), where monomeric Fab fragments of the antibodies of the invention were injected in increasing concentrations from 1 nM to 50 nM without application of surface regeneration steps after each antigen injection. Fab association was performed for 15 minutes and antigen dissociation was performed for 30 minutes. The recorded binding responses were fitted to a simple Langmuir 1:1 binding model with Scrubber 2 software for calculation of the on-rate ($k_{on}$ or ka), off-rate ($k_{off}$ or k d) and affinity ($K_D$) constants.

Results

The binding affinities of anti-PD-1 Fabs 12819.17149 and 12865.17150 and reference analogs nivolumab and pembrolizumab were evaluated. 12819.17149 and 12865.17150 are identical in $V_H$ and $V_L$ amino acid sequence to 12819.15384 and 12865.15377, respectively, but are identified by different 10-digit numbers because the heavy and light chain sequences of each of the former two variants were co-expressed on the same plasmid rather than on separate plasmids in the host cells. The non-PD-L1 and PD-L2 ligand blocking Fab 13112.15380 and Herceptin® were included as controls.

All 111 tested PD-1 mutants expressed well. Only three chimeric constructs did not bind any of the tested antibodies, suggesting that the mutations introduced into these three constructs presumably resulted in major conformational perturbations that affected the binding of all of the tested PD-1 antibodies. The change in binding affinity of Fab antibodies binding to the mutated PD-1 constructs compared to wild-type were expressed as the ratio of $K_D$ mutant/$K_D$ wild-type (normalized binding affinity). An overview of the linear epitope scanning performed by inserting 10 amino acid *Gallus gallus* sequences into human PD-1 ECD is shown in Table 11 below. At least a 5 fold affinity reduction was employed as a cut-off criteria for detecting reduced binding affinity to mutated PD-1 constructs. In some instances, no binding could be detected to specific antibodies. These constructs were listed as N.B. (not binding).

Single contact residues were also mapped by performing 83 alanine substitutions or 5 rat back-mutations (Table 12 below).

An overview of the linear epitopes or contact residues identified for tested antibodies is presented in Table 13. An illustration of the mapped binding epitopes shown as density plots on the structure of human PD-1 ECD is shown in FIG. 9.

The analysis showed that binding epitopes of 12819 and 12865 anti-PD-1 antibodies were clearly distinct compared to the reference antibodies nivolumab and pembrolizumab (Tables 11-13, FIG. 9). The core epitope of pembrolizumab (FIG. 9, panel C) was located on the C' β-strand and on the C'-D loop. Contact residues/linear epitopes were also found on the C and F β-strand where contact residues for PD-L1 also are present. The core epitope of nivolumab (FIG. 9, panel D) was present on the end of the F β-strand and on the whole G β-strand covering some of the reported PD-1 contact residues utilized by human PD-L1. The core epitopes of 12819 and 12865 (FIG. 9, panels E and F) were located on the F and G β-strands covering more area than nivolumab and overlapping with all reported contact residues for human PD-L1 in this region. 12865 was also very sensitive for mutations at residues 69-75. 12819 also shared one contact residue with pembrolizumab (V64) on the C β-strand that has also been reported to be a contact residue for human PD-L1. Both 12819 and 12865 shared linear epitopes that mapped to the C and C' β-strands and some of the C'D Loop. Apart from residue V64, no other contact residues were shared between tested antibodies. The non-ligand blocking antibody 13112 was shown by alanine scanning to map to a region distant from the PD-L1 and PD-L2 ligand blocking site (FIG. 9, panel G).

In summary, this example illustrates that although 12819, 12865, nivolumab and pembrolizumab bind to overlapping epitopes on human PD-1 that can block the binding of PD-L1 and PD-L2 ligands, each antibody has a distinct binding epitope as evidenced from competition binding analysis (epitope binning, Example 8) and shown at a molecular level by mapping individual linear epitopes and contact residues with a panel of 111 PD-1 mutants as summarized in Table 13. 12819 is also the only antibody in the investigated anti-PD-1 panel that cross-reacts with mouse PD-1 ECD ($K_D$ of 809 pM, Example 9), highlighting that the binding epitope of this antibody is unique compared to the other tested PD-1 antibodies.

TABLE 11

Binding affinity analysis for Fab antibodies binding chimeric PD-1 ECD constructs with inserted Gallus gallus sequence segments*

| Chimeric construct # | Scanned Region hu PD-1 | Mutated Region hu PD-1 | Introduced Gallus gallus mutations | 12819.17149 | 12865.17150 | nivolumab | pembrolizumab | 13112.15380 |
|---|---|---|---|---|---|---|---|---|
| 1 | 31-40 | AA 37-38 | F37L; S38F | 1.2 | 0.6 | 0.4 | 0.9 | 0.4 |
| 2 | 36-45 | AA 37-45 | F37L; S38F; L41T; V43T; V44R; T45P | 2.3 | 0.7 | 0.9 | 0.5 | 1.0 |
| 3 | 41-50 | AA 41-49 | L41T; V43T; V44R; T45P; E46A; D48S; N49S | 1.3 | 0.6 | 0.5 | 0.6 | 0.7 |
| 4 | 46-55 | AA 46-55 | E46A; D48S; N49S; T53I; S55N | 0.3 | 0.6 | 0.5 | 0.6 | 0.6 |
| 5 | 51-60 | AA 53-59 | T53I; S55N; S56I; T59S | 1.2 | 0.9 | 0.8 | 0.9 | 2.5 |
| 6 | 56-65 | AA 56-64 | F56I; T59S; E61L; S62E; V64N | 7.1 | 0.2 | 0.9 | 12.0 | 0.8 |
| 8 | 66-75 | AA 69-75 | R69Q; M70K; S71T; P72N; S73N; N74S; Q75N | 6.4 | N.B. | 1.2 | 0.9 | 1.6 |
| 10 | 76-85 | AA 76-85 | T76P; D77Q; L79I; A81G; F82I; P83IE84R; D85N | 33.7 | 13.8 | 0.8 | N.B. | 1.0 |
| 11 | 81-90 | AA 81-90 | A81G; F82I; P83IE84R; D85N; R86I; S87P; P89K; G90K | 17.7 | 5.4 | 2.0 | N.B. | 0.8 |
| 12 | 86-95 | AA 86-95 | R86I; S87P; P89K; G90K; Q91M; D92E; R94K; F95Y | 2.2 | 0.6 | 0.5 | N.B. | 0.6 |
| 15 | 101-110 | AA 103-110 | G103T; R104P; D105V; H107K; S109E; V110I | 1.3 | 0.8 | 0.9 | 0.6 | 0.9 |
| 16 | 106-115 | AA 107-115 | H107K; S109E; V110I; V111L; R112N; A113L; R114H R115Q | 3.6 | 0.4 | 0.6 | 0.7 | 0.7 |
| 17 | 111-120 | AA 111-120 | V111L; R112N; A113L; R114H R115Q; T120F | 0.2 | 0.5 | 0.4 | 0.7 | 0.7 |
| 18 | 116-125 | AA 120-125 | T120F; L122Y; A125L | 3.8 | 4.6 | 2.7 | 8.8 | 1.5 |
| 19 | 121-130 | AA 122-130 | L122Y; A125L; S127T; L128F; A129S; P130R | 175.0 | N.B. | 0.8 | 2.3 | 0.8 |

TABLE 11-continued Binding affinity analysis for Fab antibodies binding chimeric PD-1 ECD constructs with inserted Gallus gallus sequence segments*

| Chimeric construct # | Scanned Region hu PD-1 | Mutated Region hu PD-1 | Introduced Gallus gallus mutations | 12819.17149 | 12865.17150 | nivolumab | pembrolizumab | 13112.15380 |
|---|---|---|---|---|---|---|---|---|
| 20 | 126-135 | AA 127-135 | S127T; L128F; A129S; P130R; K131S; A132D; Q133K; I134VK135V | N.B. | N.B. | N.B. | 3.7 | 0.6 |
| 21 | 131-140 | AA 131-140 | K131S; A132D; Q133K; I134VK135V; L138S; R139H; A140S | N.B. | N.B. | 1.0 | 3.1 | 0.5 |
| 22 | 136-145 | AA 138-143 | L138S; R139H; A140S; E141Q; R143V | 1.9 | 1.0 | 0.5 | 0.8 | 1.0 |
| 23 | 141-146 | AA 141-143 | E141Q; R143V | 1.7 | 1.0 | 0.5 | 1.1 | 1.5 |
| | | | KD Hu PD-1 ECD wild-type (nM) | 2.68E-11 | 3.38E-09 | 5.67E-09 | 6.08E-09 | 1.24E-09 |

*Normalized binding expressed as $K_D$ mutant/$K_D$ wild-type is listed.
<5 fold $K_D$ change Chimeric mutants
5-10 fold $K_D$ change Chimeric mutants
10-50 fold $K_D$ change Chimeric mutants
50-1000 fold $K_D$ change Chimeric mutants
N.B. No binding of Chimeric mutants

TABLE 12

Fab antibody binding affinity to alanine-scanned human PD-1 ECD residues*

| Mutation | 12819.17149 | 12865.17150 | nivolumab | pembrolizumab | 13112.15380 |
|---|---|---|---|---|---|
| P21A | 2.1 | 1.0 | 0.5 | 0.6 | 1.1 |
| G22A | 1.0 | 0.9 | 0.6 | 0.8 | 1.0 |
| D26A | 1.1 | 0.8 | 1.7 | 0.7 | 1.2 |
| S27A | 0.8 | 0.8 | 2.7 | 0.8 | 1.1 |
| D29A | 1.0 | 0.9 | 1.7 | 0.7 | 1.0 |
| R30A | 1.2 | 1.2 | 1.9 | 1.3 | 1.0 |
| P31A | 1.1 | 1.0 | 2.6 | 1.0 | 1.1 |
| N33A | 1.0 | 1.1 | 0.8 | 0.8 | 1.0 |
| T36A | 1.0 | 1.0 | 0.9 | 0.9 | 0.9 |
| L42A | 1.3 | 0.5 | 0.3 | 0.2 | 2.2 |
| V44A | 1.4 | 0.8 | 0.5 | 0.3 | 9.9 |
| G47A | 1.6 | 0.5 | 0.2 | 0.2 | 0.6 |
| D48A | 1.0 | 0.6 | 0.6 | 0.4 | 2.4 |
| N49A | 1.1 | 0.7 | 0.5 | 0.5 | 1.0 |
| A50G | 1.4 | 0.6 | 0.5 | 0.4 | 1.7 |
| F56A | 1.5 | 0.5 | 1.7 | 0.6 | 0.8 |
| S57A | 1.2 | 1.0 | 0.9 | 0.9 | 1.1 |
| N58A | 1.3 | 0.7 | 1.9 | 0.7 | 1.0 |
| T59A | 0.9 | 1.0 | 1.3 | 0.3 | 0.9 |
| S60A | 1.8 | 0.6 | 1.5 | 0.7 | 1.0 |
| E61A | 1.2 | 1.1 | 0.5 | 0.3 | 1.0 |
| N66A | 2.2 | 2.1 | 0.8 | 201.3 | 1.0 |
| Y68A | 2.2 | 1.4 | 0.2 | 0.2 | 0.8 |
| S71A | 0.9 | 0.9 | 0.6 | 0.6 | 0.9 |
| P72A | 1.1 | 1.8 | 0.9 | 0.8 | 1.0 |
| S73A | 0.9 | 0.5 | 0.9 | 0.7 | 0.9 |
| Q75A | 1.0 | 0.5 | 1.0 | 0.8 | 0.9 |
| T76A | 1.4 | 0.3 | 1.2 | 0.9 | 1.2 |
| D77A | 2.8 | 0.3 | 1.0 | 134.2 | 1.0 |
| K78A | 2.6 | 0.7 | 1.0 | 268.5 | 1.1 |
| A80G | 1.2 | 0.4 | 1.1 | 0.8 | 1.0 |
| P83A | 1.5 | 0.8 | 0.9 | N.B. | 0.9 |
| E84A | 1.3 | 1.0 | 0.8 | 1.3 | 1.0 |
| D85A | 2.5 | 1.6 | 0.6 | N.B. | 0.9 |
| R86A | 1.1 | 0.7 | 0.4 | 0.3 | 0.9 |
| S87A | 1.3 | 0.9 | 0.8 | 107.4 | 1.0 |
| Q88A | 1.4 | 1.4 | 0.8 | 0.2 | 0.9 |
| P89A | 1.1 | 0.9 | 1.1 | N.B. | 0.9 |
| G90A | 1.0 | 0.8 | 1.0 | 671.1 | 1.0 |
| Q91A | 0.8 | 1.0 | 1.0 | 0.7 | 1.0 |
| D92A | 1.2 | 0.8 | 1.0 | 335.6 | 0.9 |
| C93A | 1.2 | 0.9 | 1.1 | 1.2 | 1.1 |
| R96A | 1.0 | 0.8 | 0.9 | 0.5 | 1.0 |
| T98A | 1.1 | 0.9 | 0.8 | 0.6 | 1.0 |
| P101A | 1.1 | 1.0 | 0.6 | 0.5 | 0.9 |
| N102A | 1.5 | 0.6 | 0.2 | 0.3 | 0.7 |
| G103A | 1.1 | 0.8 | 0.5 | 0.5 | 0.9 |
| R104A | 1.0 | 0.8 | 0.6 | 0.4 | 0.7 |
| R112A | 0.7 | 0.9 | 0.8 | 0.6 | 0.9 |
| R114A | 0.8 | 0.8 | 0.7 | 0.6 | 0.9 |
| N116A | 1.4 | 0.8 | 0.6 | 0.6 | 0.9 |
| G119A | 1.0 | 0.4 | 0.5 | 0.5 | 1.0 |
| G124A | 0.5 | 4.0 | 0.3 | 0.6 | 1.0 |
| L128A | 17.1 | 2.1 | 1.5 | 335.6 | 0.9 |
| P130A | 105.1 | 0.5 | 2.6 | 0.6 | 0.9 |
| K131A | N.B. | N.B. | 1.0 | 1.6 | 0.9 |
| A132G | 53.4 | 1.4 | 0.9 | 0.5 | 1.0 |
| Q133A | 0.7 | 1.4 | 1.2 | 0.6 | 0.9 |
| K135A | 4.2 | 1.1 | 0.7 | 1.4 | 1.2 |
| E136A | 0.8 | N.B. | 0.9 | 0.9 | 1.0 |
| L138A | 1.0 | 1.1 | 1.0 | 1.0 | 1.2 |
| R143A | 0.9 | 0.7 | 0.7 | 0.5 | 1.0 |
| T145A | 1.1 | 0.7 | 0.9 | 0.5 | 82.4 |
| E146A | 1.2 | 1.0 | 1.0 | 0.9 | 1.0 |
| R147A | 0.7 | 1.0 | 0.8 | 0.7 | 0.7 |
| R148A | 0.3 | 1.0 | 0.8 | 0.8 | 1.1 |
| A149G | 0.8 | 1.0 | 0.8 | 0.8 | 1.0 |
| E150A | 1.0 | 1.0 | 0.7 | 0.7 | 1.0 |
| P152A | 1.4 | 0.9 | 0.6 | 0.6 | 1.0 |
| T153A | 0.9 | 1.0 | 0.9 | 0.9 | 1.0 |
| A154G | 0.8 | 1.0 | 1.0 | 1.0 | 1.0 |
| H155A | 1.1 | 1.0 | 1.3 | 1.2 | 1.0 |
| P156A | 1.0 | 1.1 | 2.2 | 1.2 | 1.5 |
| S157A | 0.9 | 1.0 | 2.2 | 1.8 | 1.0 |
| P158A | 1.2 | 0.9 | 0.9 | 0.9 | 1.0 |
| S159A | 1.1 | 0.8 | 0.7 | 0.7 | 0.9 |
| P160A | 1.0 | 0.8 | 0.9 | 0.7 | 1.0 |
| R161A | 0.9 | 1.1 | 1.0 | 1.1 | 1.1 |
| P162A | 1.3 | 1.1 | 1.0 | 1.0 | 1.1 |
| A163G | 1.0 | 1.1 | 0.8 | 0.8 | 1.1 |
| G164A | 1.1 | 0.9 | 0.5 | 0.6 | 1.0 |
| Q165A | 1.1 | 1.1 | 0.9 | 1.0 | 1.1 |
| Rat mutation Q167A | 0.8 | 1.0 | 1.0 | 0.7 | 0.9 |
| Rat mutation P28L | 1.9 | 0.5 | 0.8 | 0.7 | 0.7 |
| Rat mutation R30K | 2.9 | 0.5 | 0.5 | 1.1 | 0.7 |

TABLE 12-continued

Fab antibody binding affinity to alanine-scanned human PD-1 ECD residues*

| Mutation | 12819.17149 | 12865.17150 | nivolumab | pembro-lizumab | 13112.15380 |
|---|---|---|---|---|---|
| Rat mutation A40T | 2.0 | 1.0 | 0.8 | 0.8 | 0.6 |
| Rat mutation V64K | 35.7 | 1.3 | 0.7 | N.B. | 1.0 |
| Rat mutation S157R | 1.6 | 0.9 | 0.9 | 0.8 | 1.0 |
| $K_D$ hu PD-1 ECD (nM) | 2.68E−11 | 3.38E−09 | 5.67E−09 | 6.08E−09 | 1.24E−09 |

*Normalized binding expressed as $K_D$ mutant/$K_D$ wild-type is listed.
<5 fold $K_D$ change
Alanine mutants
5-10 fold $K_D$ change Alanine mutants
10-50 fold $K_D$ change Alanine mutants
50-1000 fold Kp change Alanine mutants
N.B. No binding of alanine mutants

TABLE 13

Anti-PD-1 antibody binding epitopes identified by using mutated PD-1 Fc fusion constructs

| Antibody | Significant PD-L1/L2 blocking | Epitope Bin | Linear epitope | Contact Residues |
|---|---|---|---|---|
| 12819.17149 | Yes | 1C | 56-64, 69-90, 122-140 | V64, L128, P130, K131, A132 |
| 12865.17150 | Yes | 1E | 69-90, 122-140 | K131, E136 |
| nivolumab | Yes | 1D | 127-135 | |
| pembrolizumab | Yes | 1F | 56-64, 76-95, 120-125 | V64, N66, D77, K78, P83, D85, S87, P89, G90, D92, L128 |
| 13112.15380 | No | 2 | | V44, T145 |

Example 12: In Vivo Efficacy of a 12819 Antibody in Four Syngeneic Murine Tumor Models This example demonstrates the in vivo efficacy of a 12819 antibody in four syngeneic murine tumor models.

Methods $2 \times 10^5$ Sa1N (fibrosarcoma), $1 \times 10^6$ CT26 (colon carcinoma), $5 \times 10^6$ ASB-XIV (lung carcinoma), or $8 \times 10^6$ MC38 (colon carcinoma) cells were inoculated subcutaneously into the flank of 6-8 week old female A/J (Sal N), BALB/cAnNRj (CT26 and ASB-XIV), or C57BL/6 (MC38) mice. Tumors were measured three times weekly by caliper in two dimensions and tumor volume in mm 3 was calculated according to the formula: (width) 2×length×0.5. At an average tumor size of 30-50 mm³, the mice were randomized into two groups of ten animals and treatment was initiated. The mice were treated three times weekly with a total of six treatments by intraperitoneal injection of vehicle buffer or the monoclonal antibody 12819.17149 followed by an observation period. The antibody treatments were dosed at 10 mg/kg. Two-way ANOVA with Bonferroni's multiple comparisons test was applied to compare tumor volumes at each time-point between treatment groups. Statistical analyses were performed using GraphPad Prism version 5.0 (GraphPad Software, Inc.).

Results

Figure 10:
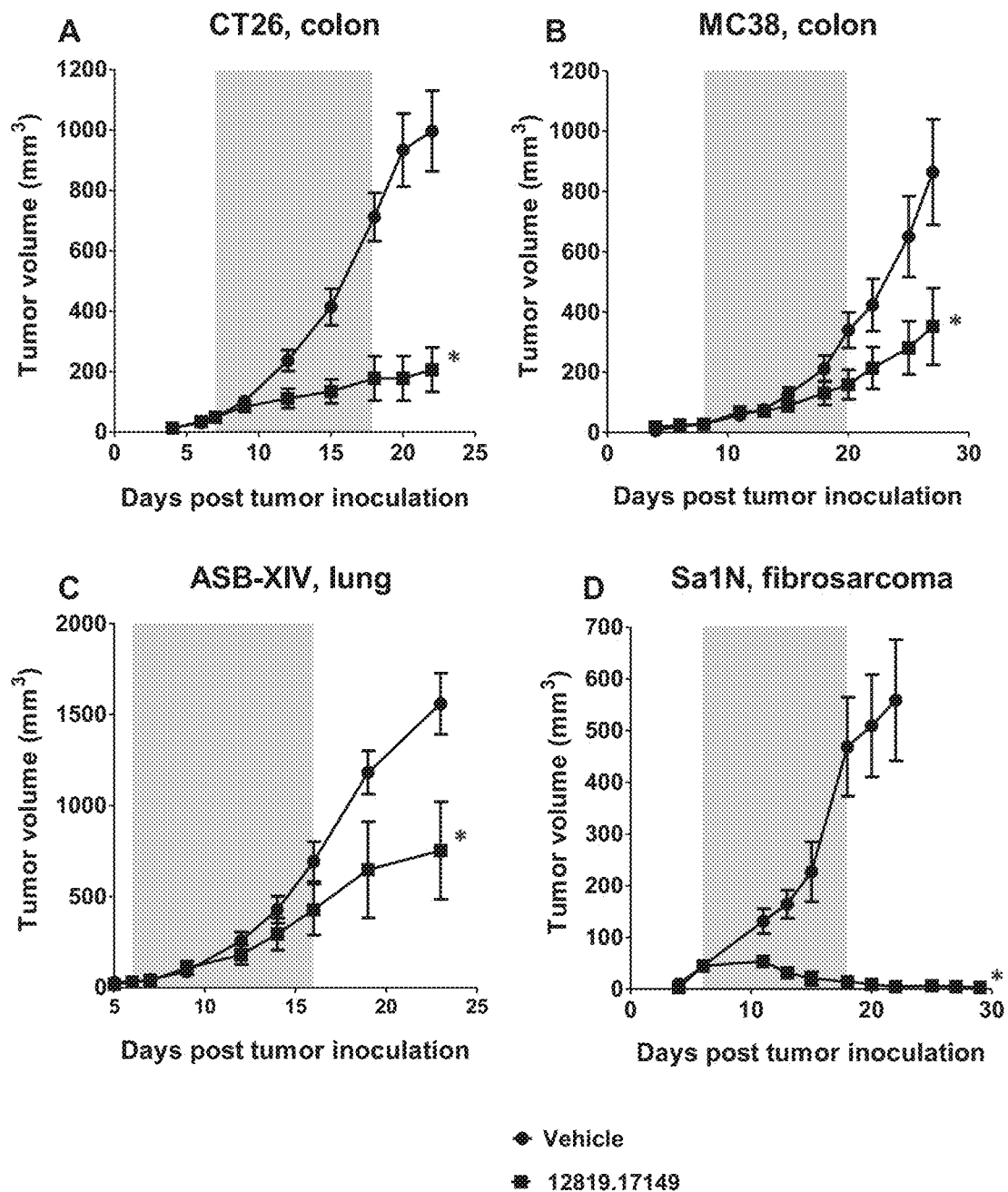
FIG. 10 (panels A-D) shows the effect of treatment with anti-PD-1 antibody 12819, 17149 or a vehicle on tumor growth in four syngeneic tumor models. A) CT26 (colon cancer). B) C38 (colon cancer). C) ASB-XIV (lung cancer). D) Sal N (fibrosarcoma). The grey area denotes the treatment period. Data are presented as means±SEM. *P<0.001.

The results show a profound tumor inhibitory effect of antibody 12819.17149 in all tested syngeneic tumor models (P<0.001 vs. vehicle) (FIG. 10). Antibody 12819.17149 induced tumor growth regression in the Sal N tumor model and resulted in tumor growth delay in the CT26, MC38 and ASB-XIV tumor models.

Example 13: In Vivo Efficacy of a 12819 Antibody in a Semi-Humanized Xenograft Tumor Model with a Mixture of CD8⁺/CD4⁺ T Cells and A375 Melanoma Cells This example demonstrates the in vivo efficacy of a 12819 antibody in a semi-humanized xenograft tumor model, where the human melanoma cell line A375 was mixed with purified human $CD8^+$ and $CD4^+$ T cells.

Methods $4.5 \times 10^5$ $CD8^+$ and $CD4^+$ T cells were isolated from a human PBMC donor and mixed with $2.05 \times 10^6$ A375 (human melanoma) cancer cells prior to subcutaneous inoculation into the flank of 6-8 week old female NODscid mice. Treatment was initiated on the day of tumor inoculation and the mice were treated three times weekly for a total of six treatments by intraperitoneal injection of vehicle buffer, Keytruda® (pembrolizumab) (10 mg/kg), or the monoclonal antibody 12819.17149 (10 mg/kg) followed by an observation period. Tumors were measured three times weekly by caliper in two dimensions and tumor volume in mm 3 was calculated according to the formula: (width) 2×length×0.5. Two-way ANOVA with Bonferroni's multiple comparisons test was applied to compare tumor volumes at each time-point between treatment groups. Statistical analyses were performed using GraphPad Prism version 5.0 (GraphPad Software, Inc.).

Results

Figure 11:
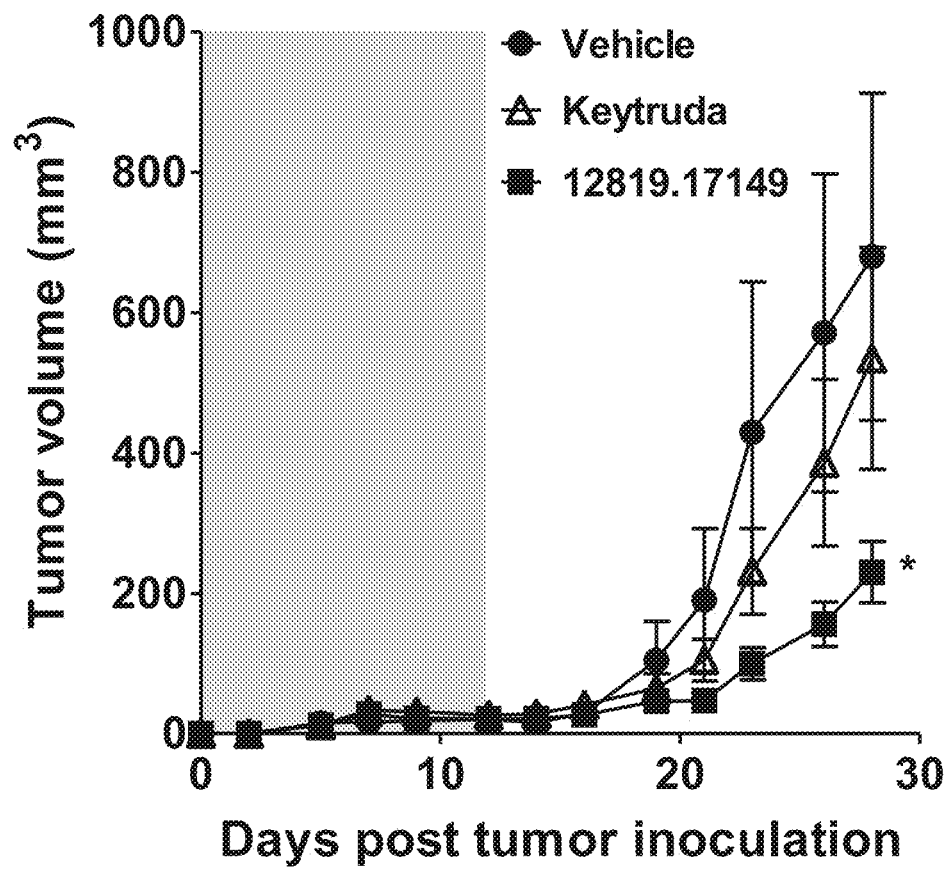
FIG. 11 shows the effect of treatment with anti-PD-1 antibody 12819.17149, pembrolizumab (Keytruda®), or vehicle on tumor growth of a semi-humanized xenograft tumor model, where the human melanoma cell line A375 was mixed with purified human CD8+ and CD4+ T cells prior to inoculation. The grey area denotes the treatment period. Data are presented as means±SEM. *P<0.001.

In the semi-humanized tumor model, treatment with antibody 12819.17149 resulted in significant tumor growth delay (P<0.001 vs. vehicle), whereas Keytruda® showed limited effect on tumor growth compared to the vehicle treated group (FIG. 11).

TABLE 14

List of SEQ ID NOS

| SEQ ID NO | Sequence |
|---|---|
| 1 | Human PD-1 amino acid sequence |
| 2 | Humanized [12819.15384] $V_H$ amino acid sequence |
| 3 | Humanized [12819.15384] $V_L$ amino acid sequence |
| 4 | Humanized [12748.15381] $V_H$ amino acid sequence |
| 5 | Humanized [12748.15381] $V_L$ amino acid sequence |
| 6 | Humanized [12865.15377] $V_H$ amino acid sequence |
| 7 | Humanized [12865.15377] $V_L$ amino acid sequence |

TABLE 14-continued

List of SEQ ID NOS

| SEQ ID NO | Sequence |
|---|---|
| 8 | Humanized [12892.15378] V$_H$ amino acid sequence |
| 9 | Humanized [12892.15378] V$_L$ amino acid sequence |
| 10 | Humanized [12796.15376] V$_H$ amino acid sequence |
| 11 | Humanized [12796.15376] V$_L$ amino acid sequence |
| 12 | Humanized [12777.15382] V$_H$ amino acid sequence |
| 13 | Humanized [12777.15382] V$_L$ amino acid sequence |
| 14 | Humanized [12760.15375] V$_H$ amino acid sequence |
| 15 | Humanized [12760.15375] V$_L$ amino acid sequence |
| 16 | Humanized [13112.15380] V$_H$ amino acid sequence |
| 17 | Humanized [13112.15380] V$_L$ amino acid sequence |
| 18-65 | CDR sequences; see SEQ ID NOs in Table 2 and sequences in Table 5, as well as the List of Sequences below |
| 66 | Humanized [12748.16124] V$_L$ amino acid sequence (alternative germline) |
| 67 | Heavy chain IgG1 constant region amino acid sequence (LALA variant) |
| 68 | Light chain constant region amino acid sequence |
| 69 | Humanized [12819.15384] V$_H$ DNA sequence |
| 70 | Humanized [12819.15384] V$_L$ DNA sequence |
| 71 | Humanized [12748.15381] V$_H$ DNA sequence |
| 72 | Humanized [12748.15381] V$_L$ DNA sequence |
| 73 | Humanized [12865.15377] V$_H$ DNA sequence |
| 74 | Humanized [12865.15377] V$_L$ DNA sequence |
| 75 | Humanized [12892.15378] V$_H$ DNA sequence |
| 76 | Humanized [12892.15378] V$_L$ DNA sequence |
| 77 | Humanized [12796.15376] V$_H$ DNA sequence |
| 78 | Humanized [12796.15376] V$_L$ DNA sequence |
| 79 | Humanized [12777.15382] V$_H$ DNA sequence |
| 80 | Humanized [12777.15382] V$_L$ DNA sequence |
| 81 | Humanized [12760.15375] V$_H$ DNA sequence |
| 82 | Humanized [12760.15375] V$_L$ DNA sequence |
| 83 | Humanized [13112.15380] V$_H$ DNA sequence |
| 84 | Humanized [13112.15380] V$_L$ DNA sequence |
| 85 | Humanized [12748.16124] V$_L$ DNA sequence (alternative germline) |
| 86 | Heavy chain constant region genomic DNA sequence with introns included |
| 87 | Heavy chain constant region cDNA sequence |
| 88 | Light chain Lambda constant region DNA sequence |
| 89 | Macaca fascicularis PD-1 polypeptide, NCBI Accession B0LAJ3_MACFA |
| 90 | Gallus Gallus PD-1 polypeptide, NCBI Accession No. XP_422723.3 |
| 91 | Mus musculus PD-1 polypeptide, NCBI Accession No. NP_032824.1 |
| 92 | Rattus norvegicus PD-1 polypeptide, NCBI Accession No. XP_006245633.1 |

The invention claimed is:

1. Isolated nucleic acid molecule(s) comprising a nucleotide sequence that encodes the heavy chain sequence, and a nucleotide sequence that encodes the light chain sequence, of an anti-PD-1 antibody or an antigen-binding portion thereof that comprises the H-CDR1-3 and L-CDR1-3 amino acid sequences of:
   a) SEQ ID NOs: 18, 19, 20, 21, 22, and 23, respectively;
   b) SEQ ID NOs: 24, 25, 26, 27, 28, and 29, respectively;
   c) SEQ ID NOs: 30, 31, 32, 33, 34, and 35, respectively;
   d) SEQ ID NOs: 36, 37, 38, 39, 40, and 41, respectively;
   e) SEQ ID NOs: 42, 43, 44, 45, 46, and 47, respectively;
   f) SEQ ID NOs: 48, 49, 50, 51, 52, and 53, respectively;
   g) SEQ ID NOs: 54, 55, 56, 57, 58, and 59, respectively; or
   h) SEQ ID NOs: 60, 61, 62, 63, 64, and 65, respectively.

2. Vector(s) comprising the isolated nucleic acid molecule(s) of claim 1, wherein said vector(s) further comprise an expression control sequence.

3. A host cell comprising the isolated nucleic acid molecule(s) of claim 1.

4. A method for producing an anti-PD-1 antibody or an antigen-binding portion thereof, comprising providing a host cell of claim 3, cultivating said host cell under conditions suitable for expression of the antibody or portion, and isolating the resulting antibody or portion.

5. The isolated nucleic acid molecule(s) of claim 1, wherein said anti-PD-1 antibody comprises a heavy chain variable domain and a light chain variable domain with amino acid sequences at least 90% identical to the amino acid sequences of:
   a) SEQ ID NOs: 2 and 3, respectively;
   b) SEQ ID NOs: 4 and 5, respectively;
   c) SEQ ID NOs: 4 and 66, respectively;
   d) SEQ ID NOs: 6 and 7, respectively;
   e) SEQ ID NOs: 8 and 9, respectively;
   f) SEQ ID NOs: 10 and 11, respectively;
   g) SEQ ID NOs: 12 and 13, respectively;
   h) SEQ ID NOs: 14 and 15, respectively; or
   i) SEQ ID NOs: 16 and 17, respectively.

6. The isolated nucleic acid molecule(s) of claim 1, wherein said anti-PD-1 antibody comprises a heavy chain variable domain and a light chain variable domain having the amino acid sequences of:
   a) SEQ ID NOs: 2 and 3, respectively;
   b) SEQ ID NOs: 4 and 5, respectively;
   c) SEQ ID NOs: 4 and 66, respectively;
   d) SEQ ID NOs: 6 and 7, respectively;
   e) SEQ ID NOs: 8 and 9, respectively;
   f) SEQ ID NOs: 10 and 11, respectively;
   g) SEQ ID NOs: 12 and 13, respectively;
   h) SEQ ID NOs: 14 and 15, respectively; or
   i) SEQ ID NOs: 16 and 17, respectively.

7. The isolated nucleic acid molecule(s) of claim 1, wherein said anti-PD-1 antibody is of isotype IgG.

8. The isolated nucleic acid molecule(s) of claim 7, wherein:
   a) the anti-PD-1 antibody is of isotype subtype IgG1 and one or both of the amino acid residues at positions 234 and 235 are mutated to Ala; or
   b) the anti-PD-1 antibody is of isotype subtype IgG4 and the amino acid residue at position 228 is mutated to Pro.

9. The isolated nucleic acid molecule(s) of claim 1, wherein the anti-PD-1 antibody or portion has at least one of the following properties:
   a) binds to human PD-1 with a $K_D$ of 750 pM or less;
   b) binds to cynomolgus PD-1 with a $K_D$ of 7 nM or less;
   c) binds to mouse PD-1 with a $K_D$ of 1 nM or less;
   d) does not bind to rat PD-1;
   e) increases IL-2 secretion in an SEB whole blood assay;
   f) increases IFN-γ secretion in a one-way mixed lymphocyte reaction assay;
   g) inhibits the interaction of PD-1 with PD-L1 by at least 60% at a concentration of 10 μg/mL in a flow cytometric competition assay;
   h) blocks binding of PD-L1 and PD-L2 to PD-1 by at least 90% at a concentration of 10 μg/mL as determined by Bio-Layer Interferometry analysis; and
   i) inhibits tumor growth in vivo.

10. The isolated nucleic acid molecule(s) of claim 1, wherein the anti-PD-1 antibody comprises:
    a) a heavy chain (HC) comprising the amino acid sequences of SEQ ID NOs: 2 and 67 and a light chain (LC) comprising the amino acid sequences of SEQ ID NOs: 3 and 68;
    b) an HC comprising the amino acid sequences of SEQ ID NOs: 4 and 67 and an LC comprising the amino acid sequences of SEQ ID NOs: 5 and 68;
    c) an HC comprising the amino acid sequences of SEQ ID NOs: 4 and 67 and an LC comprising the amino acid sequences of SEQ ID NOs: 66 and 68;
    d) an HC comprising the amino acid sequences of SEQ ID NOs: 6 and 67 and an LC comprising the amino acid sequences of SEQ ID NOs: 7 and 68;
    e) an HC comprising the amino acid sequences of SEQ ID NOs: 8 and 67 and an LC comprising the amino acid sequences of SEQ ID NOs: 9 and 68;
    f) an HC comprising the amino acid sequences of SEQ ID NOs: 10 and 67 and an LC comprising the amino acid sequences of SEQ ID NOs: 11 and 68;
    g) an HC comprising the amino acid sequences of SEQ ID NOs: 12 and 67 and an LC comprising the amino acid sequences of SEQ ID NOs: 13 and 68;
    h) an HC comprising the amino acid sequences of SEQ ID NOs: 14 and 67 and an LC comprising the amino acid sequences of SEQ ID NOs: 15 and 68; or
    i) an HC comprising the amino acid sequences of SEQ ID NOs: 16 and 67 and an LC comprising the amino acid sequences of SEQ ID NOs: 17 and 68.

11. Isolated nucleic acid molecule(s) comprising a nucleotide sequence that encodes the heavy chain sequence, and a nucleotide sequence that encodes the light chain sequence, of an anti-PD-1 antibody or an antigen-binding portion thereof that comprises the H-CDR1-3 and L-CDR1-3 amino acid sequences of SEQ ID NOs: 18, 19, 20, 21, 22, and 23, respectively.

12. Vector(s) comprising the isolated nucleic acid molecule(s) of claim 11, wherein said vector(s) further comprise an expression control sequence.

13. A host cell comprising the isolated nucleic acid molecule(s) of claim 11.

14. A method for producing an anti-PD-1 antibody or an antigen-binding portion thereof, comprising providing a host cell of claim 13, cultivating said host cell under conditions suitable for expression of the antibody or portion, and isolating the resulting antibody or portion.

15. Isolated nucleic acid molecule(s) comprising a nucleotide sequence that encodes the heavy chain sequence, and a nucleotide sequence that encodes the light chain sequence, of an anti-PD-1 antibody that comprises a heavy chain (HC) comprising the amino acid sequences of SEQ ID NOs: 2 and 67 and a light chain (LC) comprising the amino acid sequences of SEQ ID NOs: 3 and 68.

16. Vector(s) comprising the isolated nucleic acid molecule(s) of claim 15, wherein said vector(s) further comprise an expression control sequence.

17. A host cell comprising the isolated nucleic acid molecule(s) of claim 15.

18. A method for producing an anti-PD-1 antibody, comprising providing a host cell of claim 17, cultivating said host cell under conditions suitable for expression of the antibody, and isolating the resulting antibody.

* * * * *

SEQUENCE LISTING

<160> NUMBER OF SEQ ID NOS: 92

<210> SEQ ID NO 1
<211> LENGTH: 288
<212> TYPE: PRT
<213> ORGANISM: Homo sapiens

<400> SEQUENCE: 1

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95
```

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 2
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Asp Met Val Trp Val Arg Gln Ala Pro Gly Lys Gly Leu Glu Trp Val
        35                  40                  45

Ala Gly Ile Gly Asp Ser Asn Lys Met Thr Arg Tyr Ala Pro Ala Val
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Cys Ile Ala Cys Trp Asp Glu Ala Gly Arg Ile Asp
            100                 105                 110

Ala Trp Gly Gln Gly Thr Leu Val Thr Val Ser Ser
        115                 120

<210> SEQ ID NO 3
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 3

```
Ser Tyr Glu Leu Thr Gln Asp Pro Ala Val Ser Val Ala Leu Gly Gln
1               5                   10                  15

Thr Val Arg Ile Thr Cys Ser Gly Gly Ser Tyr Asp Gly Ser Ser
            20                  25                  30

Tyr Tyr Gly Trp Tyr Gln Gln Lys Pro Gly Gln Ala Pro Val Thr Val
        35                  40                  45

Ile Tyr Asn Asn Asn Arg Pro Ser Asp Ile Pro Asp Arg Phe Ser
50                  55                  60

Gly Ser Ser Ser Gly Asn Thr Ala Ser Leu Thr Ile Thr Gly Ala Gln
65                  70                  75                  80

Ala Glu Asp Glu Ala Asp Tyr Tyr Cys Gly Ser Tyr Arg Pro Glu
                85                  90                  95

Thr Asn Ser Asp Tyr Val Gly Met Phe Gly Ser Gly Thr Lys Val Thr
            100                 105                 110

Val Leu
```

<210> SEQ ID NO 4
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Asn Trp Val Arg Gln Ala Pro Gly Lys Gly Leu Glu Trp Val
        35                  40                  45

Ala Gly Ile Gly Asn Asp Gly Ser Tyr Thr Asn Tyr Gly Ala Ala Val
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Ile Arg Ser Arg Asn Asp Cys Ser Tyr Phe Leu Gly Gly
            100                 105                 110

Cys Ser Ser Gly Phe Ile Asp Val Trp Gly Gln Gly Thr Leu Val Thr
        115                 120                 125

Val Ser Ser
    130
```

<210> SEQ ID NO 5
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 5

```
Ser Tyr Glu Leu Thr Gln Asp Pro Ala Val Ser Val Ala Leu Gly Gln
1               5                   10                  15

Thr Val Arg Ile Thr Cys Ser Gly Gly Ser Ser Tyr Tyr Gly Trp
            20                  25                  30

Phe Gln Gln Lys Pro Gly Gln Ala Pro Val Thr Val Ile Tyr Glu Ser
            35                  40                  45

Asn Asn Arg Pro Ser Asp Ile Pro Asp Arg Phe Ser Gly Ser Ser Ser
        50                  55                  60

Gly Asn Thr Ala Ser Leu Thr Ile Thr Gly Ala Gln Ala Glu Asp Glu
65                  70                  75                  80

Ala Asp Tyr Tyr Cys Gly Asn Ala Asp Ser Ser Gly Ile Phe Gly
                85                  90                  95

Ser Gly Thr Lys Val Thr Val Leu
            100
```

<210> SEQ ID NO 6
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Asp His
            20                  25                  30

Gly Met Gln Trp Val Arg Gln Ala Pro Gly Lys Gly Leu Glu Tyr Val
            35                  40                  45

Gly Val Ile Asp Thr Thr Gly Arg Tyr Thr Tyr Tyr Ala Pro Ala Val
        50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Thr Cys Val Gly Gly Tyr Leu Cys Asn Thr Val Gly Ser
            100                 105                 110

Ile Asp Ala Trp Gly Gln Gly Thr Leu Val Thr Val Ser Ser
            115                 120                 125
```

<210> SEQ ID NO 7
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

```
Ser Tyr Glu Leu Thr Gln Asp Pro Ala Val Ser Val Ala Leu Gly Gln
1               5                   10                  15

Thr Val Arg Ile Thr Cys Ser Gly Gly Gly Ser Ser Tyr Tyr Gly
            20                  25                  30

Trp Tyr Gln Gln Lys Pro Gly Gln Ala Pro Val Thr Val Ile Tyr Asp
            35                  40                  45

Asp Thr Asn Arg Pro Ser Gly Ile Pro Asp Arg Phe Ser Gly Ser Ser
```

```
                    50                  55                  60
Ser Gly Asn Thr Ala Ser Leu Thr Ile Thr Gly Ala Gln Ala Glu Asp
 65                  70                  75                  80

Glu Ala Asp Tyr Tyr Cys Gly Gly Tyr Glu Gly Ser Ser His Ala Gly
                 85                  90                  95

Ile Phe Gly Ser Gly Thr Lys Val Thr Val Leu
            100                 105
```

<210> SEQ ID NO 8
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Asp Phe Ser Ser Tyr
                 20                  25                  30

Thr Met Gln Trp Val Arg Gln Ala Pro Gly Lys Gly Leu Glu Trp Val
             35                  40                  45

Gly Val Ile Ser Ser Thr Gly Ser Thr Gly Tyr Gly Pro Ala Val
         50                  55                  60

Lys Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Lys Ser Ile Ser Gly Asp Ala Trp Ser Val Asp Gly Leu Asp Ala
                100                 105                 110

Trp Gly Gln Gly Thr Leu Val Thr Val Ser Ser
            115                 120
```

<210> SEQ ID NO 9
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Ser Tyr Glu Leu Thr Gln Asp Pro Ala Val Ser Val Ala Leu Gly Gln
  1               5                  10                  15

Thr Val Arg Ile Thr Cys Ser Gly Gly Gly Ser Ala Tyr Gly Trp Tyr
                 20                  25                  30

Gln Gln Lys Pro Gly Gln Ala Pro Val Thr Val Ile Tyr Tyr Asn Asn
             35                  40                  45

Gln Arg Pro Ser Gly Ile Pro Asp Arg Phe Ser Gly Ser Ser Ser Gly
         50                  55                  60

Asn Thr Ala Ser Leu Thr Ile Thr Gly Ala Gln Ala Glu Asp Glu Ala
 65                  70                  75                  80

Asp Tyr Tyr Cys Gly Ser Tyr Asp Ser Ser Ala Val Gly Ile Phe Gly
                 85                  90                  95

Ser Gly Thr Lys Val Thr Val Leu
            100
```

<210> SEQ ID NO 10
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
            20                  25                  30

Thr Met Gln Trp Val Arg Gln Ala Pro Gly Lys Gly Leu Glu Trp Val
        35                  40                  45

Gly Val Ile Ser Ser Thr Gly Ser Thr Gly Tyr Gly Pro Ala Val
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Ser Val Ser Gly Asp Ala Trp Ser Val Asp Gly Leu Asp Ala
            100                 105                 110

Trp Gly Gln Gly Thr Leu Val Thr Val Ser Ser
        115                 120

<210> SEQ ID NO 11
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 11

Ser Tyr Glu Leu Thr Gln Asp Pro Ala Val Ser Val Ala Leu Gly Gln
1               5                   10                  15

Thr Val Arg Ile Thr Cys Ser Gly Gly Gly Ser Ala Tyr Gly Trp Tyr
            20                  25                  30

Gln Gln Lys Pro Gly Gln Ala Pro Val Thr Val Ile Tyr Tyr Asn Asn
        35                  40                  45

Gln Arg Pro Ser Asp Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ser Tyr Asp Ser Ser Ala Val Gly Ile Phe Gly
                85                  90                  95

Ser Gly Thr Lys Val Thr Val Leu
            100

<210> SEQ ID NO 12
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
            20                  25                  30

Gly Met Gln Trp Val Arg Gln Ala Pro Gly Lys Gly Leu Glu Trp Val
        35                  40                  45

Gly Val Ile Ser Gly Ser Gly Ile Thr Thr Leu Tyr Ala Pro Ala Val
    50                  55                  60

Lys Gly Arg Ala Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Thr Arg Ser Pro Ser Ile Thr Asp Gly Trp Thr Tyr Gly Gly Ala Trp
            100                 105                 110

Ile Asp Ala Trp Gly Gln Gly Thr Leu Val Thr Val Ser Ser
        115                 120                 125

<210> SEQ ID NO 13
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ser Tyr Glu Leu Thr Gln Asp Pro Ala Val Ser Val Ala Leu Gly Gln
1               5                   10                  15

Thr Val Arg Ile Thr Cys Ser Gly Gly Asp Gly Ser Tyr Gly Trp Phe
            20                  25                  30

Gln Gln Lys Pro Gly Gln Ala Pro Val Thr Val Ile Tyr Asp Asn Asp
        35                  40                  45

Asn Arg Pro Ser Asp Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Asn Ala Asp Leu Ser Gly Ile Phe Gly Ser
                85                  90                  95

Gly Thr Lys Val Thr Val Leu
            100

<210> SEQ ID NO 14
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Asn Met Val Trp Val Arg Gln Ala Pro Gly Lys Gly Leu Glu Tyr Val

```
                    35                  40                  45

Ala Glu Ile Ser Ser Asp Gly Ser Phe Thr Trp Tyr Ala Thr Ala Val
    50                  55                  60

Lys Gly Arg Ala Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Ser Asp Cys Ser Ser Ser Tyr Tyr Gly Tyr Ser Cys Ile Gly
            100                 105                 110

Ile Ile Asp Ala Trp Gly Gln Gly Thr Leu Val Thr Val Ser Ser
            115                 120                 125

<210> SEQ ID NO 15
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ser Tyr Glu Leu Thr Gln Asp Pro Ala Val Ser Val Ala Leu Gly Gln
1               5                   10                  15

Thr Val Arg Ile Thr Cys Ser Gly Gly Ile Ser Asp Asp Gly Ser Tyr
            20                  25                  30

Tyr Tyr Gly Trp Phe Gln Gln Lys Pro Gly Gln Ala Pro Val Thr Val
        35                  40                  45

Ile Tyr Ile Asn Asp Arg Arg Pro Ser Asn Ile Pro Asp Arg Phe Ser
    50                  55                  60

Gly Ser Ser Ser Gly Asn Thr Ala Ser Leu Thr Ile Thr Gly Ala Gln
65                  70                  75                  80

Ala Glu Asp Glu Ala Asp Tyr Tyr Cys Gly Ser Tyr Asp Ser Ser Ala
                85                  90                  95

Gly Val Gly Ile Phe Gly Ser Gly Thr Lys Val Thr Val Leu
            100                 105                 110

<210> SEQ ID NO 16
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asn Met Phe Trp Val Arg Gln Ala Pro Gly Lys Gly Leu Glu Phe Val
        35                  40                  45

Ala Glu Ile Ser Gly Ser Asn Thr Gly Ser Arg Thr Trp Tyr Ala Pro
    50                  55                  60

Ala Val Lys Gly Arg Ala Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Ala Lys Ser Ile Tyr Gly Gly Tyr Cys Ala Gly Gly Tyr Ser
            100                 105                 110

Cys Gly Val Gly Leu Ile Asp Ala Trp Gly Gln Gly Thr Leu Val Thr
        115                 120                 125

Val Ser Ser
    130

<210> SEQ ID NO 17
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Ser Tyr Glu Leu Thr Gln Asp Pro Ala Val Ser Val Ala Leu Gly Gln
1               5                   10                  15

Thr Val Arg Ile Thr Cys Ser Gly Gly Ser Ser Asp Tyr Tyr Gly Trp
            20                  25                  30

Phe Gln Gln Lys Pro Gly Gln Ala Pro Val Thr Val Ile Tyr Tyr Asn
        35                  40                  45

Asn Lys Arg Pro Ser Asp Ile Pro Asp Arg Phe Ser Gly Ser Ser Ser
    50                  55                  60

Gly Asn Thr Ala Ser Leu Thr Ile Thr Gly Ala Gln Ala Glu Asp Glu
65                  70                  75                  80

Ala Asp Tyr Tyr Cys Gly Asn Ala Asp Ser Ser Val Gly Val Phe Gly
                85                  90                  95

Ser Gly Thr Lys Val Thr Val Leu
            100

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Phe Thr Phe Thr Arg Tyr Asp
1               5

<210> SEQ ID NO 19
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ile Gly Asp Ser Asn Lys Met Thr
1               5

<210> SEQ ID NO 20
<211> LENGTH: 19
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 20

Cys Ala Lys Gly Ser Cys Ile Ala Cys Trp Asp Glu Ala Gly Arg Ile
1               5                   10                  15

Asp Ala Trp

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gly Ser Tyr Asp Gly Ser Ser Tyr
1               5

<210> SEQ ID NO 22
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Asn Asn Asn
1

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Cys Gly Ser Tyr Asp Arg Pro Glu Thr Asn Ser Asp Tyr Val Gly Met
1               5                   10                  15

Phe

<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Phe Thr Phe Ser Asp Tyr Ala
1               5

<210> SEQ ID NO 25
<211> LENGTH: 8
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 25

Ile Gly Asn Asp Gly Ser Tyr Thr
1               5

<210> SEQ ID NO 26
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Cys Ala Ser Asp Ile Arg Ser Arg Asn Asp Cys Ser Tyr Phe Leu Gly
1               5                   10                  15

Gly Cys Ser Ser Gly Phe Ile Asp Val Trp
            20                  25

<210> SEQ ID NO 27
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ser Ser Tyr Ser
1

<210> SEQ ID NO 28
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Glu Ser Asn
1

<210> SEQ ID NO 29
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Cys Gly Asn Ala Asp Ser Ser Ser Gly Ile Phe
1               5                   10

<210> SEQ ID NO 30
<211> LENGTH: 8
<212> TYPE: PRT
<213> ORGANISM: Artificial Sequence
<220> FEATURE:
<221> NAME/KEY: source
```

-continued

<223> OTHER INFORMATION: /note="Description of Artificial Sequence:
      Synthetic peptide"

<400> SEQUENCE: 30

Gly Phe Asp Phe Ser Asp His Gly
1               5

<210> SEQ ID NO 31
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ile Asp Thr Thr Gly Arg Tyr Thr
1               5

<210> SEQ ID NO 32
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Cys Ala Lys Thr Thr Cys Val Gly Gly Tyr Leu Cys Asn Thr Val Gly
1               5                   10                  15

Ser Ile Asp Ala Trp
            20

<210> SEQ ID NO 33
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gly Ser Ser Ser Tyr
1               5

<210> SEQ ID NO 34
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Asp Asp Thr
1

<210> SEQ ID NO 35
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:

```
              Synthetic peptide"

<400> SEQUENCE: 35

Cys Gly Gly Tyr Glu Gly Ser Ser His Ala Gly Ile Phe
1               5                   10

<210> SEQ ID NO 36
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gly Phe Asp Phe Ser Ser Tyr Thr
1               5

<210> SEQ ID NO 37
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ile Ser Ser Thr Gly Gly Ser Thr
1               5

<210> SEQ ID NO 38
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Cys Val Lys Ser Ile Ser Gly Asp Ala Trp Ser Val Asp Gly Leu Asp
1               5                   10                  15

Ala Trp

<210> SEQ ID NO 39
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gly Ser Ala
1

<210> SEQ ID NO 40
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 40

Tyr Asn Asn
1

<210> SEQ ID NO 41
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Cys Gly Ser Tyr Asp Ser Ser Ala Val Gly Ile Phe
1               5                   10

<210> SEQ ID NO 42
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Phe Asp Phe Ser Ser Tyr Thr
1               5

<210> SEQ ID NO 43
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ile Ser Ser Thr Gly Gly Ser Thr
1               5

<210> SEQ ID NO 44
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Cys Val Lys Ser Val Ser Gly Asp Ala Trp Ser Val Asp Gly Leu Asp
1               5                   10                  15

Ala Trp

<210> SEQ ID NO 45
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45
```

Gly Ser Ala
1

<210> SEQ ID NO 46
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Tyr Asn Asn
1

<210> SEQ ID NO 47
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Cys Gly Ser Tyr Asp Ser Ser Ala Val Gly Ile Phe
1               5                   10

<210> SEQ ID NO 48
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Phe Asp Phe Ser Ser Tyr Gly
1               5

<210> SEQ ID NO 49
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ile Ser Gly Ser Gly Ile Thr Thr
1               5

<210> SEQ ID NO 50
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Cys Thr Arg Ser Pro Ser Ile Thr Asp Gly Trp Thr Tyr Gly Gly Ala
1               5                   10                  15

Trp Ile Asp Ala Trp

```
<210> SEQ ID NO 51
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Asp Gly Ser
1

<210> SEQ ID NO 52
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Asp Asn Asp
1

<210> SEQ ID NO 53
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Cys Gly Asn Ala Asp Leu Ser Gly Gly Ile Phe
1               5                   10

<210> SEQ ID NO 54
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gly Phe Thr Phe Ser Thr Phe Asn
1               5

<210> SEQ ID NO 55
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ile Ser Ser Asp Gly Ser Phe Thr
1               5

<210> SEQ ID NO 56
```

```
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Cys Ala Lys Ser Asp Cys Ser Ser Ser Tyr Tyr Gly Tyr Ser Cys Ile
1               5                   10                  15

Gly Ile Ile Asp Ala Trp
            20

<210> SEQ ID NO 57
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ile Ser Asp Asp Gly Ser Tyr Tyr
1               5

<210> SEQ ID NO 58
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Ile Asn Asp
1

<210> SEQ ID NO 59
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Cys Gly Ser Tyr Asp Ser Ser Ala Gly Val Gly Ile Phe
1               5                   10

<210> SEQ ID NO 60
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Phe Thr Phe Ser Ser Tyr Asn
1               5

<210> SEQ ID NO 61
<211> LENGTH: 10
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ile Ser Gly Ser Asn Thr Gly Ser Arg Thr
1               5                   10

<210> SEQ ID NO 62
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Cys Ala Lys Ser Ile Tyr Gly Gly Tyr Cys Ala Gly Gly Tyr Ser Cys
1               5                   10                  15

Gly Val Gly Leu Ile Asp Ala Trp
            20

<210> SEQ ID NO 63
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ser Ser Asp Tyr
1

<210> SEQ ID NO 64
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Tyr Asn Asn
1

<210> SEQ ID NO 65
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Cys Gly Asn Ala Asp Ser Ser Val Gly Val Phe
1               5                   10

<210> SEQ ID NO 66
<211> LENGTH: 104
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

```
Ser Tyr Glu Leu Thr Gln Pro Pro Ser Val Ser Val Ser Pro Gly Gln
1               5                   10                  15

Thr Ala Arg Ile Thr Cys Ser Gly Gly Ser Ser Tyr Tyr Gly Trp
            20                  25                  30

Phe Gln Gln Lys Pro Gly Gln Ala Pro Val Thr Val Ile Tyr Glu Ser
            35                  40                  45

Asn Asn Arg Pro Ser Asp Ile Pro Glu Arg Phe Ser Gly Ser Ser Ser
50                  55                  60

Gly Thr Thr Val Thr Leu Thr Ile Ser Gly Val Gln Ala Glu Asp Glu
65                  70                  75                  80

Ala Asp Tyr Tyr Cys Gly Asn Ala Asp Ser Ser Ser Gly Ile Phe Gly
                85                  90                  95

Ser Gly Thr Lys Val Thr Val Leu
            100
```

<210> SEQ ID NO 67
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 67

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 68
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 69
<211> LENGTH: 379
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69
ggcgcgccga ggtgcagctg ctggaatctg gaggaggact ggtccagcca ggtggatccc    60
tgcgactgag ctgcgccgct tctggattca cctttacaag atacgacatg gtgtgggtcc   120
gccaggcacc aggaaaggga ctggagtggg tggctggtat cggcgatagt aacaagatga   180
cccgctacgc acctgccgtc aaagggaggg caacaattag tcgggacaac tcaagaata    240 ctctgtatct gcagatgaat tccctgcgag ctgaggatac agcagtgtac tattgtgcca   300

```
aaggtagctg catcgcctgt tgggacgaag ctggccgtat tgatgcatgg ggacagggga      360
ctctggtgac cgtctcgag                                                  379

<210> SEQ ID NO 70
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70
gctagcctct tacgagctga ctcaggaccc tgcagtgagt gtcgccctgg ccagacagt       60 gagaatcact tgctccggcg agggagcta cgatggttcc agctactatg ctggtatca      120 gcagaagcca ggacaggcac ctgtgaccgt catctataac aataacaata ggccatctga    180
cattcccgat cggttcagtg gatctagttc agggaacaca gcttctctga ccattacagg    240
agcccaggct gaggacgaag cagattacta ttgtgggtca tacgacaggc cagaaacaaa    300
ttccgattat gtgggaatgt ttggtagcgg cactaaagtc accgtcctag g             351

<210> SEQ ID NO 71
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
ggcgcgccga ggtgcagctg ctggaaagcg gaggaggact ggtccagcca ggtggatctc     60
tgcgactgag ttgcgccgct tcaggcttca cattttctga ctacgccatg aactgggtga    120
ggcaggctcc tggcaaggga ctggagtggg tcgcaggaat cgggaacgat ggaagttaca    180
ctaattatgg agcagccgtg aagggggagag ctactatttc ccgcgacaac agcaaaaata   240
ccctgtacct gcagatgaac tcactgagag ctgaagatac cgcagtgtac tattgtgcct    300
ctgacatcag gagtcggaat gattgctcct atttcctggg agggtgttcc agcggcttta    360
ttgacgtgtg gggtcagggc accctggtca cagtctcgag                          400

<210> SEQ ID NO 72
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72
gctagcctct tacgagctga cccaggaccc agcagtgtcc gtcgccctgg ccagacagt       60 gagaatcact tgctccggcg gatccagcta cagctatggg tggttccagc agaagcccgg    120
tcaggcccct gtgaccgtca tctatgaaag taacaatagg ccatcagaca ttcccgatcg    180
gttttctggc tctagttcag gaaacacagc tagtctgacc atcacagggg cccaggctga    240
ggacgaagct gattactatt gtggcaatgc agattccagc tctggaattt tcgggtccgg    300
tactaaagtc accgtcctag g                                              321
```

<210> SEQ ID NO 73
<211> LENGTH: 385
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 73

```
ggcgcgccga ggtgcagctg ctggaatccg gaggaggact ggtccagcca ggtggatccc      60
tgcgactgag ctgcgccgct tctggattcg actttagcga tcacgggatg cagtgggtga     120
gacaggcacc aggcaaggga ctggagtacg tgggtgtcat cgacaccaca ggccgctata     180
catactatgc acctgccgtc aagggcaggg ctaccattag tcgggacaac tcaaaaaata     240
cactgtacct gcagatgaac tctctgaggg ctgaagatac tgcagtgtac tattgcgcca     300
aaactacctg cgtgggaggg tacctgtgca ataccgtcgg aagtatcgat gcttggggac     360
aggggacact ggtgactgtc tcgag                                           385
```

<210> SEQ ID NO 74
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 74

```
gctagcctcc tacgagctga ctcaggaccc agcagtgagc gtcgccctgg ccagacagt      60
gagaatcact tgctctggcg gagggtccag ctcttactat ggttggtacc agcagaagcc     120
cggccaggct cctgtgaccg tcatctatga cgatacaaac aggccaagtg gaattcccga     180
tcggttctca ggtagttcat ccggcaatac agcttctctg accatcacag gggcccaggc     240
tgaggacgaa gcagattact attgtggtgg ctatgaagga agctctcacg ccgggatttt     300
tggaagtggg actaaagtca ccgtcctagg                                      330
```

<210> SEQ ID NO 75
<211> LENGTH: 376
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75

```
ggcgcgccga ggtgcagctg ctggaaagtg gaggaggact ggtccagcca ggtggaagcc      60
tgagactgtc ttgcgccgct agtggcttcg acttttccag ctacaccatg cagtgggtga     120
ggcaggcacc aggcaaggga ctggagtggg tgggcgtcat ctctagtact ggagggtcta     180
ccggatacgg gcctgctgtg aagggaaggg caacaatttc acgggataac tccaaaaata     240
ctctgtatct gcagatgaac agcctgaggg cagaagacac agccgtgtac tattgcgtga     300
aatcaatctc cggagatgcc tggtctgtgg acgggctgga tgcttggggt cagggcaccc     360
tggtcacagt ctcgag                                                     376
```

<210> SEQ ID NO 76
<211> LENGTH: 321

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76
gctagcctca tacgagctga cccaggaccc agcagtgtcc gtcgccctgg gacagacagt      60
gagaatcact tgctccggag gaggatccgc tacggttgg tatcagcaga agcccggcca      120
ggcacctgtg accgtcatct actataacaa tcagaggcca tctggcattc cgaccggtt      180 cagtggatcc agctctggga acacagcaag tctgaccatc acaggcgccc aggctgagga      240
cgaagccgat tactattgtg aagctatga tagttcagct gtggggattt ttggttctgg      300
cactaaagtc accgtcctag g                                                321

<210> SEQ ID NO 77
<211> LENGTH: 376
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77
ggcgcgccga ggtgcagctg ctggaaagtg gaggaggact ggtccagcca ggtggaagcc      60
tgagactgtc ttgcgccgct agtggcttcg acttttccag ctacaccatg cagtgggtga      120
ggcaggcacc aggcaaggga ctggagtggg tgggcgtcat ctctagtact ggagggtcta      180
ccggatacgg gcctgctgtg aagggaaggg caacaatttc acgggataac tccaaaaata      240
ctctgtatct gcagatgaac agcctgaggg cagaagacac agccgtgtac tattgcgtga      300
aatcagtctc cggagatgcc tggtctgtgg acgggctgga tgcttggggt cagggcaccc      360
tggtcacagt ctcgag                                                      376

<210> SEQ ID NO 78
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
gctagcctca tacgagctga cccaggaccc agcagtgtcc gtcgccctgg gccagacagt      60
gagaatcact tgctccggag gaggatccgc tacggttgg tatcagcaga agcccggcca      120
ggcacctgtg accgtcatct actataacaa tcagaggcca tctgacattc ccgatcggtt      180
cagtggatcc agctctggga acacagcaag tctgaccatc acaggcgccc aggctgagga      240
cgaagccgat tactattgtg aagctatga tagttcagct gtggggattt ttggttctgg      300
cactaaagtc accgtcctag g                                                321

<210> SEQ ID NO 79
<211> LENGTH: 385
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 79

```
ggcgcgccga ggtgcagctg ctggaatccg gaggaggact ggtccagcca ggtggaagcc    60
tgcgactgtc ttgcgccgct agtggattcg acttttccag ctacgaatg cagtgggtga    120
ggcaggcacc aggcaaggga ctggagtggg tgggcgtcat ctctggaagt gggattacca    180
cactgtacgc acctgccgtc aagggaaggg ctactatctc acgggacaac tctaaaaata    240
cagtgtatct gcagatgaac tccctgagag ctgaagatac cgcagtctac tattgtacac    300
gctcacccte catcacagac ggctggactt atggaggggc ctggattgat gcttggggtc    360
agggcactct ggtgaccgtc tcgag                                         385
```

<210> SEQ ID NO 80
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80

```
gctagccagc tacgagctga cccaggaccc agcagtgtcc gtcgccctgg gccagacagt    60
gagaatcact tgcagtggcg gagatgggtc atacggttgg ttccagcaga agcccggaca    120
ggcccctgtg accgtcatct atgacaacga taataggcca tctgacattc ccgatcggtt    180
tagtggctcc agctctggaa acacagcttc tctgaccatc acaggggccc aggctgagga    240
cgaagctgat tactattgtg gcaatgcaga cctgtccggg ggtattttcg gcagcggaac    300
taaagtcacc gtcctagg                                                  318
```

<210> SEQ ID NO 81
<211> LENGTH: 388
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 81

```
ggcgcgccga ggtgcagctg ctggaatctg gaggaggact ggtccagcca ggtggatccc    60
tgagactgag ctgcgccgct tctggattca cctttagtac attcaacatg gtgtgggtca    120
ggcaggcacc tggaaaggga ctggagtacg tggctgaaat ctccagcgac ggctcttttta    180
catggtatgc aactgccgtc aagggcaggg ccaccattag tcgggataac tcaaaaaata    240
cagtgtacct gcagatgaat tccctgaggg ctgaggacac cgcagtctac tattgcgcaa    300
aatccgattg ttctagttca tactatggat atagctgtat cgggatcatt gacgcttggg    360
gtcagggcac tctggtgacc gtctcgag                                       388
```

<210> SEQ ID NO 82
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82
```

```
gctagcctcc tatgagctga cccaggaccc agcagtgagc gtcgccctgg gccagacagt    60
gagaatcact tgctccggcg gaattagcga cgatggctct tactattacg gatggttcca    120
gcagaagccc ggacaggccc ctgtgaccgt catctatatt aacgacaggc ggccaagtaa    180
tatccccgat aggttttcag ggtccagctc tggtaacaca gcttctctga ccattacagg    240
ggcccaggct gaggacgaag ctgattatta ctgtggctct tacgatagtt cagcaggggt    300
gggtatcttc ggcagtggaa ctaaagtcac cgtcctagg                           339
```

<210> SEQ ID NO 83
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83

```
ggcgcgccga ggtgcagctg ctggaaagtg gaggaggact ggtccagcca ggtggatcac    60
tgagactgtc ctgcgccgcc tccggcttca ccttttccag ctacaacatg ttctgggtgc    120
gccaggcacc aggaaaggga ctggagtttg tcgctgaaat ctctggtagt aatactggaa    180
gccgaacctg gtacgcacct gccgtgaagg gcagggctac aatttctcgg gacaacagta    240
aaaatactct gtatctgcag atgaactctc tgagggctga ggatacagca gtgtactatt    300
gtgcaaaatc aatctacgga gggtattgcg ccggtggcta ttcctgtggt gtgggcctga    360
ttgacgcatg gggacagggg accctggtca cagtctcgag                          400
```

<210> SEQ ID NO 84
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84

```
gctagcctca tacgagctga cccaggaccc agcagtgtcc gtcgccctgg gccagacagt    60
gagaatcact tgcagtggcg gatccagcga ttactatggg tggttccagc agaagcccgg    120
tcaggcccct gtgaccgtca tctactataa caacaagagg ccatctgaca ttcccgatcg    180
gtttagtggc tctagttcag gaaacacagc ctccctgacc attacagggg cccaggctga    240
ggacgaagct gattactatt gtggcaatgc agactccagc gtgggagtct cgggtctgg     300 tactaaggtg accgtcctag g                                              321
```

<210> SEQ ID NO 85
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85

```
gctagcctct tacgagctga ctcagccacc ttccgtgtcc gtgtcccag acagaccgc      60 aagaatcaca tgcagtggcg gatccagcta ctcatatggg tggttccagc agaagcctgg    120
```

| | |
|---|---|
| tcaggcccc gtgacagtca tctatgagag caacaatagg ccttctgaca ttccagaacg | 180 |
| gtttagtggc tctagttcag gaaccacagt gactctgacc atcagcgggg tccaggccga | 240 |
| ggacgaagct gattactatt gtggcaacgc tgattccagc tctggaattt tcgggtccgg | 300 |
| tacaaaagtg actgtcctag g | 321 |

<210> SEQ ID NO 86
<211> LENGTH: 1606
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86

| | |
|---|---|
| ctcgagtgcc tccaccaagg gcccatcggt cttccccctg gcaccctcct ccaagagcac | 60 |
| ctctgggggc acagcggccc tgggctgcct ggtcaaggac tacttccccg aaccggtgac | 120 |
| ggtgtcgtgg aactcaggcg ccctgaccag cggcgtgcac accttcccgg ctgtcctaca | 180 |
| gtcctcagga ctctactccc tcagcagcgt ggtgaccgtg ccctccagca gcttgggcac | 240 |
| ccagacctac atctgcaacg tgaatcacaa gcccagcaac accaaggtgg acaagagagt | 300 |
| tggtgagagg ccagcacagg gagggagggt gtctgctgga agccaggctc agcgctcctg | 360 |
| cctggacgca tcccggctat gcagtcccag tccaggcag caaggcaggc ccgtctgcc | 420 |
| tcttcacccg gaggcctctg cccgccccac tcatgctcag ggagagggtc ttctggcttt | 480 |
| ttccccaggc tctgggcagg cacaggctag gtgcccctaa cccaggccct gcacacaaag | 540 |
| gggcaggtgc tgggctcaga cctgccaaga gccatatccg ggaggaccct gcccctgacc | 600 |
| taagcccacc ccaaaggcca aactctccac tccctcagct cggacacctt ctctcctccc | 660 |
| agattccagt aactcccaat cttctctctg cagagcccaa atcttgtgac aaaactcaca | 720 |
| catgcccacc gtgcccaggt aagccagccc aggcctcgcc ctccagctca aggcgggaca | 780 |
| ggtgccctag agtagcctgc atccagggac aggccccagc cgggtgctga cacgtccacc | 840 |
| tccatctctt cctcagcacc tgaagccgcc ggggaccgt cagtcttcct cttcccccca | 900 |
| aaacccaagg acaccctcat gatctcccgg acccctgagg tcacatgcgt ggtggtggac | 960 |
| gtgagccacg aagaccctga ggtcaagttc aactggtacg tggacggcgt ggaggtgcat | 1020 |
| aatgccaaga caaagccgcg ggaggagcag tacaacagca cgtaccgtgt ggtcagcgtc | 1080 |
| ctcaccgtcc tgcaccagga ctggctgaat ggcaaggagt acaagtgcaa ggtctccaac | 1140 |
| aaagccctcc cagcccccat cgagaaaacc atctccaaag ccaaaggtgg acccgtggg | 1200 |
| gtgcgagggc cacatggaca gaggccggct cggcccaccc tctgccctga gagtgaccgc | 1260 |
| tgtaccaacc tctgtcccta cagggcagcc ccgagaacca caggtgtaca ccctgccccc | 1320 |
| atcccgggag gagatgacca gaaccaggt cagcctgacc tgcctggtca aaggcttcta | 1380 |
| tcccagcgac atcgccgtgg agtgggagag caatgggcag ccggagaaca actacaagac | 1440 |
| cacgcctccc gtgctggact ccgacggctc cttcttcctc tatagcaagc tcaccgtgga | 1500 |
| caagagcagg tggcagcagg ggaacgtctt ctcatgctcc gtgatgcatg aggctctgca | 1560 |
| caaccactac acgcagaaga gcctctccct gtccccgggt aaatga | 1606 |

<210> SEQ ID NO 87
<211> LENGTH: 1000
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 87
ctcgagtgcc tccaccaagg gcccatcggt cttccccctg caccctcct    ccaagagcac      60 ctctgggggc acagcggccc tgggctgcct ggtcaaggac tacttccccg aaccggtgac     120
ggtgtcgtgg aactcaggcg ccctgaccag cggcgtgcac accttcccgg ctgtcctaca     180
gtcctcagga ctctactccc tcagcagcgt ggtgaccgtg ccctccagca gcttgggcac     240
ccagacctac atctgcaacg tgaatcacaa gcccagcaac accaaggtgg acaagagagt     300
tgagcccaaa tcttgtgaca aaactcacac atgcccaccg tgcccagcac ctgaagccgc     360 cggggggaccg tcagtcttcc tcttccccc  aaaacccaag gacaccctca tgatctcccg     420
gacccctgag gtcacatgcg tggtggtgga cgtgagccac gaagaccctg aggtcaagtt     480
caactggtac gtggacggcg tggaggtgca taatgccaag acaaagccgc gggaggagca     540
gtacaacagc acgtaccgtg tggtcagcgt cctcaccgtc ctgcaccagg actggctgaa     600
tggcaaggag tacaagtgca aggtctccaa caaagccctc ccagccccca tcgagaaaac     660
catctccaaa gccaaagggc agccccgaga accacaggtg tacaccctgc ccccatcccg     720
ggaggagatg accaagaacc aggtcagcct gacctgcctg gtcaaaggct tctatcccag     780
cgacatcgcc gtggagtggg agagcaatgg gcagccggag aacaactaca agaccacgcc     840
tcccgtgctg gactccgacg gctccttctt cctctatagc aagctcaccg tggacaagag     900
caggtggcag caggggaacg tcttctcatg ctccgtgatg catgaggctc tgcacaacca     960
ctacacgcag aagagcctct ccctgtcccc gggtaaatga                          1000

<210> SEQ ID NO 88
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88
cctaggtcag cccaaggcca accccactgt cactctgttc ccgccctcct ctgaggagct      60
ccaagccaac aaggccacac tagtgtgtct gatcagtgac ttctacccgg gagctgtgac     120
agtggcctgg aaggcagatg gcagccccgt caaggcggga gtggagacca ccaaaccctc     180
caaacagagc aacaacaagt acgcggccag cagctacctg agcctgacgc ccgagcagtg     240
gaagtcccac agaagctaca gctgccaggt cacgcatgaa gggagcaccg tggagaagac     300
agtggcccct acagaatgtt cataa                                            325

<210> SEQ ID NO 89
<211> LENGTH: 288
<212> TYPE: PRT
<213> ORGANISM: Macaca fascicularis

<400> SEQUENCE: 89

Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30
```

Asn Ala Pro Thr Phe Ser Pro Ala Leu Leu Val Thr Glu Gly Asp
            35                  40                  45

Asn Ala Thr Phe Thr Cys Ser Phe Ser Asn Ala Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Arg Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                 165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                 245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
            275                 280                 285

<210> SEQ ID NO 90
<211> LENGTH: 304
<212> TYPE: PRT
<213> ORGANISM: Gallus gallus

<400> SEQUENCE: 90

Met Gly Lys Glu Ala Pro Ser Gly Thr Gly His Arg His Arg Ala Gln
 1                5                  10                  15

Gln Gly Thr Arg Arg Pro Ala Met Ala Leu Gly Thr Ser Arg Thr Met
             20                  25                  30

Trp Asp Ser Thr Glu Ala Ala Leu Val Val Leu Cys Val Leu Leu Leu
             35                  40                  45

Cys Cys Asn Pro Pro Leu Ala Gly Cys His Gln Val Thr Leu Phe Pro
 50                  55                  60

Ala Thr Leu Thr Arg Pro Ala Gly Ser Ser Ala Thr Phe Ile Cys Asn
 65                  70                  75                  80

Ile Ser Met Glu Asn Ser Ser Leu Glu Phe Asn Leu Asn Trp Tyr Gln
                 85                  90                  95

Lys Thr Asn Asn Ser Asn Pro Gln Lys Ile Ala Gly Ile Ile Arg Asn
            100                 105                 110

Ile Pro Gln Lys Lys Met Glu Lys Tyr Arg Leu Phe Asn Asn Thr Pro
            115                 120                 125

```
Val Phe Lys Met Glu Ile Leu Asn Leu His Gln Asn Asp Ser Gly Phe
            130                 135                 140

Tyr Tyr Cys Gly Leu Ile Thr Phe Ser Arg Ser Asp Lys Val Val Glu
145                 150                 155                 160

Ser Ser His Ser Gln Leu Val Val Thr Glu Ala Pro Glu Lys Thr Asn
                165                 170                 175

Thr Ile Asp Glu Pro Ser Glu Glu Ser Ser Pro Pro Asp His Ile
            180                 185                 190

Lys Ala Val Leu Leu Gly Thr Leu Leu Leu Ala Gly Val Ile Val Leu
                195                 200                 205

Leu Leu Phe Gly Tyr Ile Ile Ile Asn Asn Arg Arg Ala Asp Val Gln
            210                 215                 220

Lys Pro Ser Ser Gly Asn Thr Leu Ala Glu Val Lys Pro Pro Val Val
225                 230                 235                 240

Pro Val Pro Thr Val Asp Tyr Gly Val Leu Glu Phe Gln Arg Asp Pro
                245                 250                 255

His Ser Gln Val Pro Leu Glu Thr Cys Pro Ala Glu Gln Thr Glu Tyr
                260                 265                 270

Ala Thr Ile Val Phe Pro Glu Glu Lys Pro Ile Thr Pro Glu Arg Gly
                275                 280                 285

Lys Arg His Lys Asp Glu Arg Thr Trp Gln Leu Pro Ser Gln Pro Cys
            290                 295                 300

<210> SEQ ID NO 91
<211> LENGTH: 288
<212> TYPE: PRT
<213> ORGANISM: Mus musculus

<400> SEQUENCE: 91

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
                20                  25                  30

Arg Ser Leu Thr Phe Tyr Pro Ala Trp Leu Thr Val Ser Glu Gly Ala
            35                  40                  45

Asn Ala Thr Phe Thr Cys Ser Leu Ser Asn Trp Ser Glu Asp Leu Met
50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
```

```
                195                 200                 205
Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285

<210> SEQ ID NO 92
<211> LENGTH: 288
<212> TYPE: PRT
<213> ORGANISM: Rattus norvegicus

<400> SEQUENCE: 92

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285
```